United States Patent
Jeanguenat et al.

(10) Patent No.: US 10,721,933 B2
(45) Date of Patent: Jul. 28, 2020

(54) PESTICIDALLY ACTIVE SEMI-CARBAZONES AND THIOSEMICARBAZONES DERIVATIVES

(71) Applicant: Syngenta Participations AG, Basel (CH)

(72) Inventors: Andre Jeanguenat, Stein (CH); Fides Benfatti, Stein (CH); Thomas Pitterna, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/544,272

(22) PCT Filed: Jan. 19, 2016

(86) PCT No.: PCT/EP2016/051015
§ 371 (c)(1),
(2) Date: Jul. 18, 2017

(87) PCT Pub. No.: WO2016/116445
PCT Pub. Date: Jul. 28, 2016

(65) Prior Publication Data
US 2018/0007907 A1  Jan. 11, 2018

(30) Foreign Application Priority Data
Jan. 23, 2015 (EP) .................... 15152277

(51) Int. Cl.
| | | |
|---|---|---|
| *A01N 47/34* | (2006.01) |
| *C07D 277/68* | (2006.01) |
| *C07D 277/66* | (2006.01) |
| *C07D 263/57* | (2006.01) |
| *C07D 235/18* | (2006.01) |
| *C07D 231/56* | (2006.01) |
| *C07D 215/227* | (2006.01) |
| *C07D 471/04* | (2006.01) |
| *C07D 209/50* | (2006.01) |
| *C07D 209/48* | (2006.01) |
| *C07D 487/00* | (2006.01) |

(52) U.S. Cl.
CPC .......... *A01N 47/34* (2013.01); *C07D 209/48* (2013.01); *C07D 209/50* (2013.01); *C07D 215/227* (2013.01); *C07D 231/56* (2013.01); *C07D 235/18* (2013.01); *C07D 263/57* (2013.01); *C07D 277/66* (2013.01); *C07D 277/68* (2013.01); *C07D 471/04* (2013.01); *C07D 487/00* (2013.01)

(58) Field of Classification Search
None
See application file for complete search history.

(56) References Cited

U.S. PATENT DOCUMENTS

| | | | |
|---|---|---|---|
| 5,240,949 A | 8/1993 | Lesieur et al. |
| 5,530,028 A | 6/1996 | Lidert |

FOREIGN PATENT DOCUMENTS

| | | | | |
|---|---|---|---|---|
| CN | 104230845 A | 12/2014 | | |
| JP | H06199763 A | 7/1994 | | |
| JP | H09301947 A | 11/1997 | | |
| JP | 2013501749 A1 | 1/2013 | | |
| JP | 2013510137 A | 3/2013 | | |
| WO | WO-2008018645 A1 * | 2/2008 | ............ | A01N 41/10 |
| WO | WO-2009112445 A1 * | 9/2009 | ......... | A61K 31/4184 |
| WO | 2011/017504 A1 | 2/2011 | | |
| WO | 2011055320 A1 | 5/2011 | | |

OTHER PUBLICATIONS

Melha, K. S. A. "In-vitro antibacterial, antifungal activity of some transition metal complexes of thiosemicarbazone Schiff base . . . " Journal of Enzyme Inhibition and Medicinal Chemistry, 2008, 23(4) 493-503. (Year: 2008).*
Aly, M. M. et al. European Journal of Medicinal Chemistry, 45, 3365-3373 (Year: 2010).*
Saremi et al. (Comm. Agric. Appl. Biol. Sci., 2008, 73(2), Abstract only).*
Kumar, Sanjay et al: "Imidazopyridine derivatives as inhibitors of PI3K, mTOR, STAT3, TNF-.alpha., IL-6 and their preparation and use for the treatment of diseases", XP002755583, Chemical Abstracts Service, Columbus, Ohio, US; 2011.
Ragab, Fatma Abdel-Fattah et al: "Synthesis and anticonvulsant activity of certain substituted furochromone, benzofuran and flavone derivatives", Chemical & Pharmaceutical Bulletin, 58 (9), 1148-1156 CODEN: CPBTAL; ISSN: 0009-2363, 2010.
International Search Report and Written Opinion for PCT/EP2016/051015, dated Apr. 25, 2016.
L. Blackburn, R.J.K. Taylor, Org. Lett., 2001(3), pp. 1637-1639.
A.L. Korich, T.S. Huges, Synlett, 2007, pp. 2602-2604.
Ch. V. Reddy, J.V. Kingston, J.G. Verkade, J. Org. Chem., 2008(73), pp. 3047-3062.

* cited by examiner

*Primary Examiner* — Erin E Hirt
(74) *Attorney, Agent, or Firm* — Baker & Hostetler, LLP; Toni-Junell Herbert

(57) ABSTRACT

Compounds of formula (I), wherein the substituents are as defined in claim 1, and agrochemically acceptable salts and enantiomers thereof, can be used as insecticides.

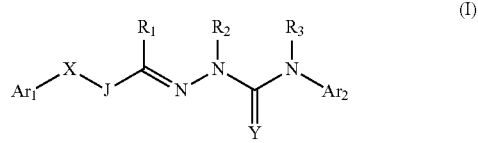

22 Claims, No Drawings

PESTICIDALLY ACTIVE SEMI-CARBAZONES AND THIOSEMICARBAZONES DERIVATIVES

RELATED APPLICATION INFORMATION

This application is a 371 of International Application No. PCT/EP2016/051015, filed 19 Jan. 2016, which claims priority to EP Patent Application No. 15152277.8, filed 23 Jan. 2015, the contents of which are incorporated herein by reference herein.

The present invention relates to compounds of formula (I) below, to processes for preparing them, to pesticidal, in particular insecticidal, acaricidal, molluscicidal and nematicidal compositions comprising them and to methods of using them to combat and control pests such as insect, acarine, mollusc and nematode pests.

Heterocyclic compounds with pesticidal activity are known and described, for example, in WO09/102736, WO11/017505, WO12/109125, WO13/116052, WO13/116053 and WO14/011429. There have now been found novel pesticidal active semi-carbazones and thiosemicarbazones with bicyclic rings substituents.

The present invention accordingly relates to compounds of formula I,

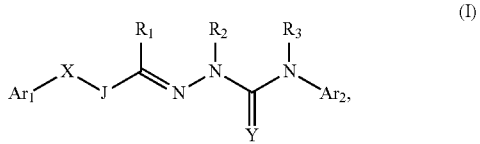

(I)

wherein, $Ar_1$ and $Ar_2$ are independently of each other phenyl, thienyl, pyridyl, pyrimidinyl, pyrazinyl, pyridazinyl, furanyl, wherein said phenyl, thienyl, pyridyl, pyrimidinyl, pyrazinyl, pyridazinyl, furanyl can be substituted by one to three substituents independently selected from the group consisting of hydrogen, $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_2$-$C_4$haloalkenyl, $C_2$-$C_4$haloalkynyl, $C_3$-$C_6$halocycloalkyl, $C_1$-$C_3$haloalkyl-$C_3$-$C_6$cycloalkyl, $C_3$-$C_6$cycloalkoxy, halogen, cyano, cyano-$C_1$-$C_4$alkyl, cyano-$C_3$-$C_6$cycloalkyl, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_1$-$C_4$alkylamino, $C_2$-$C_6$dialkylamino, $C_3$-$C_6$cycloalkylamino, $C_1$-$C_4$alkyl-$C_3$-$C_6$cycloalkylamino, $C_2$-$C_4$alkylcarbonyl, CHO, $C_2$-$C_6$alkoxycarbonyl, $C_2$-$C_6$haloalkoxycarbonyl, $C_2$-$C_6$alkylaminocarbonyl, $C_2$-$C_6$haloalkylaminocarbonyl or $C_2$-$C_8$ dialkylaminocarbonyl;

X is a direct bond, O, S, $SO_2$, $CR_4R_5$ or $NR_6$;

Y is oxygen or sulfur;

$R_1$ is hydrogen, $C_1$-$C_6$-alkyl, halo-$C_1$-$C_6$-alkyl, $C_3$-$C_6$-cycloalkyl or $C_1$-$C_3$-alkoxy;

$R_2$ and $R_3$ are independently from each other hydrogen, $C_1$-$C_6$-alkyl, $C_1$-$C_6$-haloalkyl, $C_3$-$C_6$-cycloalkyl, halo-$C_3$-$C_6$-cycloalkyl, $C_2$-$C_6$-alkenyl, $C_2$-$C_6$haloalkenyl, $C_2$-$C_6$-alkynyl, $C_2$-$C_6$haloalkynyl, $C_1$-$C_4$alkoxy-$C_1$-$C_4$alkyl, $C_1$-$C_4$haloalkylsulfinyl, $C_1$-$C_4$haloalkylsulfonyl, $C_1$-$C_4$alkylsulfinyl, $C_1$-$C_4$alkylsulfonyl, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, or $C_1$-$C_4$alkoxyimino-$C_1$-$C_4$alkyl; provided that when $R_2$ and $R_3$ are different from hydrogen, $R_2$ and $R_3$ can be substituted by one to three substituents independently selected from the group consisting of $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_2$-$C_4$haloalkenyl, $C_2$-$C_4$haloalkynyl, $C_3$-$C_6$halocycloalkyl, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_1$-$C_4$alkylamino, $C_2$-$C_6$dialkylamino, $C_3$-$C_6$cycloalkylamino, $C_1$-$C_4$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, and $C_2$-$C_8$ dialkylaminocarbonyl;

$R_4$, $R_5$ and $R_6$ are independently from each other hydrogen, $C_1$-$C_6$-alkyl, halo-$C_1$-$C_6$-alkyl, $C_3$-$C_6$-cycloalkyl or $C_1$-$C_3$-alkoxy;

J is an aromatic or a non-aromatic bicyclic ring system selected from $J_1$, $J_2$ and $J_3$

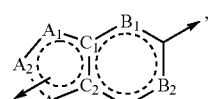

($J_1$)

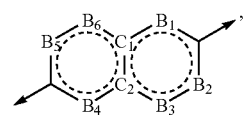

($J_2$)

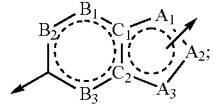

($J_3$)

wherein ⊂ ⊃ indicates that the ring is aromatic or non-aromatic;

in which the arrows show the connectivity as depicted in formula (I) wherein $A_1$ is nitrogen, N—$R_{7a}$, sulfur, oxygen or C—$R_{7b}$;
$A_2$ is nitrogen, N—$R_{8a}$, sulfur, oxygen or C—$R_{8b}$;
$A_3$ is nitrogen, N—$R_{9a}$, sulfur, oxygen or C—$R_{9b}$;
$B_1$ is nitrogen or C—$R_{10}$;
$B_2$ is nitrogen or C—$R_{11}$;
$B_3$ is nitrogen or C—$R_{12}$;
$B_4$ is nitrogen or C—$R_{13}$;
$B_5$ is nitrogen or C—$R_{14}$;
$B_6$ is nitrogen or C—$R_{15}$;
$C_1$ is nitrogen, C or C—$R_{16}$;
$C_2$ is nitrogen, C or C—$R_{17}$;
with the provisos that
a) not more than two substituents A can be oxygen or sulfur,
b) when two substituents A are oxygen and/or sulphur, these substituents are $A_1$ and $A_3$, and $A_2$ is C—$R_{8b}$, and
c) when $C_1$ is N, then $C_2$ is C or C—$R_{16}$ and when $C_2$ is N, then $C_1$ is C or C—$R_{17}$;

each of $R_{7a}$, $R_{7b}$, $R_{8a}$, $R_{8b}$, $R_{9a}$, $R_{9b}$, $R_{10}$, $R_{11}$, $R_{12}$, $R_{13}$, $R_{14}$, $R_{15}$, $R_{16}$ and $R_{17}$ are independently from each other hydrogen, halogen, nitro, cyano, hydroxy, =O, CHO, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkoxy, $C_1$-$C_4$alkoxy-$C_1$-$C_4$alkoxy-$C_1$-$C_4$alkyl, $C_1$-$C_4$haloalkoxy, $C_1$-$C_4$alkylthio, $C_1$-$C_4$haloalkylthio, $C_1$-$C_4$haloalkylsulfinyl, $C_1$-$C_4$haloalkylsulfonyl, $C_1$-$C_4$alkylsulfinyl, $C_1$-$C_4$alkylsulfonyl, $C_1$-$C_4$alkylsulfonyl-$C_1$-$C_4$alkyl, $C_1$-$C_4$alkylsulfoximino-$C_1$-$C_4$alkyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, $C_1$-$C_4$alkoxyimino-$C_1$-$C_4$alkyl, —CONHSO$_2$—$C_1$-$C_6$-alkyl, —CONHSO$_2$N($C_1$-$C_6$-alkyl)$_2$, or $C_3$-$C_6$trialkylsilyl;

or an agrochemically acceptable salt, stereoisomer, tautomer and N-oxide of the compounds of formula I.

In one embodiment, the present invention relates to compounds of formula I,

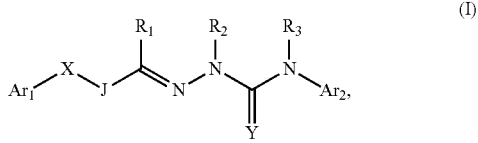

wherein,

Ar$_1$ and Ar$_2$ are independently of each other phenyl, thienyl, pyridyl, pyrimidinyl, pyrazinyl, pyridazinyl, furanyl, wherein said phenyl, thienyl, pyridyl, pyrimidinyl, pyrazinyl, pyridazinyl, furanyl can be substituted by one to three substituents independently selected from the group consisting of hydrogen, $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_2$-$C_4$haloalkenyl, $C_2$-$C_4$haloalkynyl, $C_3$-$C_6$halocycloalkyl, $C_1$-$C_3$haloalkyl-$C_3$-$C_6$cycloalkyl, $C_3$-$C_6$cycloalkoxy, halogen, cyano, cyano-$C_1$-$C_4$alkyl, cyano-$C_3$-$C_6$cycloalkyl nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_1$-$C_4$alkylamino, $C_2$-$C_6$dialkylamino, $C_3$-$C_6$cycloalkylamino, $C_1$-$C_4$alkyl-$C_3$-$C_6$cycloalkylamino, $C_2$-$C_4$alkylcarbonyl, CHO, $C_2$-$C_6$alkoxycarbonyl, $C_2$-$C_6$haloalkoxycarbonyl, $C_2$-$C_6$alkylaminocarbonyl, $C_2$-$C_6$haloalkylaminocarbonyl or $C_2$-$C_8$ dialkylaminocarbonyl;

X is a direct bond, O, S, SO$_2$, CR$_4$R$_5$ or NR$_6$;

Y is oxygen or sulfur;

R$_1$ is hydrogen, $C_1$-$C_6$-alkyl, halo-$C_1$-$C_6$-alkyl, $C_3$-$C_6$-cycloalkyl or $C_1$-$C_3$-alkoxy;

R$_2$ and R$_3$ are independently from each other hydrogen, $C_1$-$C_6$-alkyl, $C_1$-$C_6$-haloalkyl, $C_3$-$C_6$-cycloalkyl, halo-$C_3$-$C_6$-cycloalkyl, $C_2$-$C_6$-alkenyl, $C_2$-$C_6$haloalkenyl, $C_2$-$C_6$-alkynyl, $C_2$-$C_6$haloalkynyl, $C_1$-$C_4$alkoxy-$C_1$-$C_4$alkyl, $C_1$-$C_4$haloalkylsulfinyl, $C_1$-$C_4$haloalkylsulfonyl, $C_1$-$C_4$alkylsulfinyl, $C_1$-$C_4$alkylsulfonyl, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, or $C_1$-$C_4$alkoxyimino-$C_1$-$C_4$alkyl; provided that when R$_2$ and R$_3$ are different from hydrogen, R$_2$ and R$_3$ can be substituted by one to three substituents independently selected from the group consisting of $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_2$-$C_4$haloalkenyl, $C_2$-$C_4$haloalkynyl, $C_3$-$C_6$halocycloalkyl, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_1$-$C_4$alkylamino, $C_2$-$C_6$dialkylamino, $C_3$-$C_6$cycloalkylamino, $C_1$-$C_4$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, and $C_2$-$C_8$ dialkylaminocarbonyl;

R$_4$, R$_5$ and R$_6$ are independently from each other hydrogen, $C_1$-$C_6$-alkyl, halo-$C_1$-$C_6$-alkyl, $C_3$-$C_6$-cycloalkyl or $C_1$-$C_3$-alkoxy;

J is an aromatic bicyclic ring system selected from J$_1$, J$_2$ and J$_3$

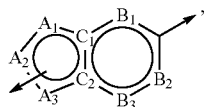

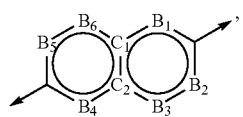

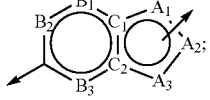

wherein ◯ indicates that the ring is aromatic;
in which the arrows show the connectivity as depicted in formula (I) wherein
A$_1$ is nitrogen, N—R$_{7a}$, sulfur, oxygen or C—R$_{7b}$;
A$_2$ is nitrogen, N—R$_{8a}$, sulfur, oxygen or C—R$_{5b}$;
A$_3$ is nitrogen, N—R$_{9a}$, sulfur, oxygen or C—R$_{9b}$;
B$_1$ is nitrogen or C—R$_{10}$;
B$_2$ is nitrogen or C—R$_{11}$;
B$_3$ is nitrogen or C—R$_{12}$;
B$_4$ is nitrogen or C—R$_{13}$;
B$_5$ is nitrogen or C—R$_{14}$;
B$_6$ is nitrogen or C—R$_{15}$;
C$_1$ is nitrogen or C;
C$_2$ is nitrogen or C;
with the provisos that
a) not more than two substituents A can be oxygen or sulfur,
b) when two substituents A are oxygen and/or sulphur, these substituents are A$_1$ and A$_3$, and A$_2$ is C—R$_{8b}$, and
c) when C$_1$ is N, then C$_2$ is C and when C$_2$ is N, then C$_1$ is C;
each of R$_{7a}$, R$_{7b}$, R$_{8a}$, R$_{8b}$, R$_{9a}$, R$_{9b}$, R$_{10}$, R$_{11}$, R$_{12}$, R$_{13}$, R$_{14}$ and R$_{15}$ are independently from each other hydrogen, halogen, nitro, cyano, hydroxy, =O, CHO, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkoxy, C-$C_4$alkoxy-$C_1$-$C_4$alkoxy-$C_1$-$C_4$alkyl, $C_1$-$C_4$haloalkoxy, $C_1$-$C_4$alkylthio, $C_1$-$C_4$haloalkylthio, $C_1$-$C_4$haloalkylsulfinyl, $C_1$-$C_4$haloalkylsulfonyl, $C_1$-$C_4$alkylsulfinyl, $C_1$-$C_4$alkylsulfonyl, $C_1$-$C_4$alkylsulfonyl-$C_1$-$C_4$alkyl, $C_1$-$C_4$alkylsulfoximino-$C_1$-$C_4$alkyl, $C_1$-$C_4$alkylamino, $C_2$-$C_4$dialkylamino, $C_3$-$C_6$cycloalkylamino, $C_1$-$C_6$alkyl- $C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, $C_1$-$C_4$alkoxyimino-$C_1$-$C_4$alkyl, —CONHSC$_2$—$C_1$-$C_6$-alkyl, —CONHSO$_2$N($C_1$-$C_6$-alkyl)$_2$, or $C_3$-$C_6$trialkylsilyl;

or an agrochemically acceptable salt, stereoisomer, tautomer and N-oxide of the compounds of formula I.

The present invention accordingly relates to compounds of formula I,

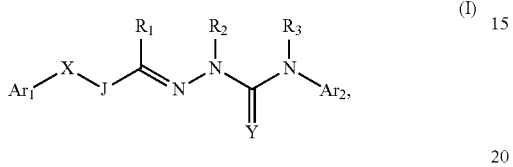

(I)

Wherein,

Ar$_1$ and Ar$_2$ are independently of each other phenyl, thienyl, pyridyl, pyrimidinyl, pyrazinyl, pyridazinyl, furanyl, wherein said phenyl, thienyl, pyridyl, pyrimidinyl, pyrazinyl, pyridazinyl, furanyl can be substituted by one to three substituents independently selected from the group consisting of hydrogen, $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_2$-$C_4$haloalkenyl, $C_2$-$C_4$haloalkynyl, $C_3$-$C_6$halocycloalkyl, $C_1$-$C_3$haloalkyl-$C_3$-$C_6$cycloalkyl, $C_3$-$C_6$cycloalkoxy, halogen, cyano, cyano-$C_1$-$C_4$alkyl, cyano-$C_3$-$C_6$cycloalkyl nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_1$-$C_4$alkylamino, $C_2$-$C_6$dialkylamino, $C_3$-$C_6$cycloalkylamino, $C_1$-$C_4$alkyl-$C_3$-$C_6$cycloalkylamino, $C_2$-$C_4$alkylcarbonyl, CHO, $C_2$-$C_6$alkoxycarbonyl, $C_2$-$C_6$haloalkoxycarbonyl, $C_2$-$C_6$alkylaminocarbonyl, $C_2$-$C_6$haloalkylaminocarbonyl or $C_2$-$C_8$dialkylaminocarbonyl;

X is a direct bond, O, S, SO$_2$, CR$_4$R$_5$ or NR$_6$;

Y is oxygen or sulfur;

R$_1$ is hydrogen, $C_1$-$C_6$-alkyl, halo-$C_1$-$C_6$-alkyl, $C_3$-$C_6$-cycloalkyl or $C_1$-$C_3$-alkoxy;

R$_2$ and R$_3$ are independently from each other hydrogen, $C_1$-$C_6$-alkyl, $C_1$-$C_6$-haloalkyl, $C_3$-$C_6$-cycloalkyl, halo-$C_3$-$C_6$-cycloalkyl, $C_2$-$C_6$-alkenyl, $C_2$-$C_6$-haloalkenyl, $C_2$-$C_6$-alkynyl, $C_2$-$C_6$-haloalkynyl, $C_1$-$C_4$alkoxy-$C_1$-$C_4$alkyl, $C_1$-$C_4$haloalkylsulfinyl, $C_1$-$C_4$haloalkylsulfonyl, $C_1$-$C_4$alkylsulfinyl, $C_1$-$C_4$alkylsulfonyl, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, or $C_1$-$C_4$alkoxyimino-$C_1$-$C_4$alkyl; provided that when R$_2$ and R$_3$ are different from hydrogen, R$_2$ and R$_3$ can be substituted by one to three substituents independently selected from the group consisting of $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_2$-$C_4$haloalkenyl, $C_2$-$C_4$haloalkynyl, $C_3$-$C_6$halocycloalkyl, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_1$-$C_4$alkylamino, $C_2$-$C_6$dialkylamino, $C_3$-$C_6$cycloalkylamino, $C_1$-$C_4$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, and $C_2$-$C_8$ dialkylaminocarbonyl;

R$_4$, R$_5$ and R$_6$ are independently from each other hydrogen, $C_1$-$C_6$-alkyl, halo-$C_1$-$C_6$-alkyl, $C_3$-$C_6$-cycloalkyl or $C_1$-$C_3$-alkoxy;

J is an aromatic or a non-aromatic bicyclic ring system selected from J$_1$, J$_2$ and J$_3$

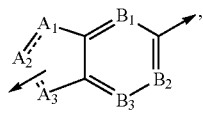

(J$_1$)

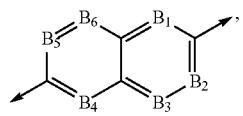

(J$_2$)

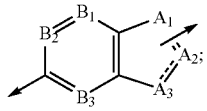

(J$_3$)

in which the arrows show the connectivity as depicted in formula (I) wherein

A$_1$ is nitrogen, N—R$_{7a}$, sulfur, oxygen or C—R$_{7b}$;
A$_2$ is nitrogen, N—R$_{8a}$, sulfur, oxygen or C—R$_{8b}$;
A$_3$ is nitrogen, N—R$_{9a}$, sulfur, oxygen or C—R$_{9b}$;
B$_1$ is nitrogen or C—R$_{10}$;
B$_2$ is nitrogen or C—R$_{11}$;
B$_3$ is nitrogen or C—R$_{12}$;
B$_4$ is nitrogen or C—R$_{13}$;
B$_5$ is nitrogen or C—R$_{14}$;
B$_6$ is nitrogen or C—R$_{15}$; with the provisos that
a) not more than two substituents A can be oxygen or sulfur, and
b) when two substituents A are oxygen and/or sulphur, these substituents are A$_1$ and A$_3$, and A$_2$ is C—R$_{8b}$; each of R$_{7a}$, R$_{7b}$, R$_{8a}$, R$_{8b}$, R$_{9a}$, R$_{9b}$, R$_{10}$, R$_{11}$, R$_{12}$, R$_{13}$, R$_{14}$ and R$_{15}$, are independently from each other hydrogen, halogen, nitro, cyano, hydroxy, =O, CHO, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkoxy, $C_1$-$C_4$alkoxy-$C_1$-$C_4$alkoxy-$C_1$-$C_4$alkyl, $C_1$-$C_4$haloalkoxy, $C_1$-$C_4$alkylthio, $C_1$-$C_4$haloalkylthio, $C_1$-$C_4$haloalkylsulfinyl, $C_1$-$C_4$haloalkylsulfonyl, $C_1$-$C_4$alkylsulfinyl, $C_1$-$C_4$alkylsulfonyl, $C_1$-$C_4$alkylsulfonyl-$C_1$-$C_4$alkyl, $C_1$-$C_4$alkylsulfoximino-$C_1$-$C_4$alkyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, $C_1$-$C_4$alkoxyimino-$C_1$-$C_4$alkyl, —CONHSC$_2$—$C_1$-$C_6$-alkyl, —CONHSO$_2$N($C_1$-$C_6$-alkyl)$_2$, or $C_3$-$C_6$trialkylsilyl;

and agrochemically acceptable salts and enantiomers, stereoisomers, tautomers and N-oxides of the compounds of formula I.

Definitions

The term "halogen" refers to fluorine, chlorine, bromine or iodine, preferably fluorine, chlorine or bromine.

Alkyl substituents may be straight-chained or branched. Alkyl on its own or as part of another substituent is, depending upon the number of carbon atoms mentioned, for example, methyl, ethyl, n-propyl, n-butyl, n-pentyl, n-hexyl and the isomers thereof, for example, iso-propyl, iso-butyl, sec-butyl, tert-butyl, iso-amyl or pivaloyl.

Alkenyl substituents can be in the form of straight or branched chains, and the alkenyl moieties, where appropriate, can be of either the (E)- or (Z)-configuration. Examples are vinyl and allyl. The alkenyl groups are preferably $C_2$-$C_6$, more preferably $C_2$-$C_4$ and most preferably $C_2$-$C_3$ alkenyl groups.

Alkynyl substituents can be in the form of straight or branched chains. Examples are ethynyl and propargyl. The alkynyl groups are preferably $C_2$-$C_6$, more preferably $C_2$-$C_4$ and most preferably $C_2$-$C_3$ alkynyl groups.

Haloalkyl groups may contain one or more identical or different halogen atoms and, for example, may stand for $CH_2Cl$, $CHCl_2$, $CCl_3$, $CH_2F$, $CHF_2$, $CF_3$, $CF_3CH_2$, $CH_3CF_2$, $CF_3CF_2$ or $CCl_3CCl_2$. Haloalkenyl groups are alkenyl groups, respectively, which are substituted with one or more of the same or different halogen atoms and are, for example, 2,2-difluorovinyl or 1,2-dichloro-2-fluoro-vinyl.

Haloalkynyl groups are alkynyl groups, respectively, which are substituted with one or more of the same or different halogen atoms and are, for example, 1-chloro-prop-2-ynyl.

Alkoxy means a radical —OR, where R is alkyl, e.g. as defined above. Alkoxy groups include, but are not limited to, methoxy, ethoxy, 1-methylethoxy, propoxy, butoxy, 1-methylpropoxy and 2-methylpropoxy.

Cyano means a —CN group.

Amino means an $NH_2$ group.

Hydroxyl or hydroxy stands for a —OH group.

The presence of one or more C=N double bonds in a compound of formula I means that the compounds may occur in E or Z isomeric forms. Formula I is intended to include all those possible isomeric forms and mixtures thereof.

The presence of one or more possible asymmetric carbon atoms in a compound of formula I means that the compounds may occur in optically isomeric forms, i.e. enantiomeric or diastereomeric forms. Also atropisomers may occur as a result of restricted rotation about a single bond. Formula I is intended to include all those possible isomeric forms and mixtures thereof. The present invention includes all those possible isomeric forms and mixtures thereof for a compound of formula I. Likewise, formula I is intended to include all possible tautomers. The present invention includes all possible tautomeric forms for a compound of formula I.

In each case, the compounds of formula I according to the invention are in free form, in oxidized form as a N-oxide or in salt form, e.g. an agronomically usable salt form.

The following list provides definitions, including preferred definitions, for substituents $A_1$, $A_2$, $A_3$, $B_1$, $B_2$, $B_3$, $B_4$, $B_5$, $B_6$, $Ar_1$, $Ar_2$, $R_1$, $R_2$, $R_3$, $R_4$, $R_5$, $R_6$, $R_{7a}$, $R_{7b}$, $R_{8a}$, $R_{8b}$, $R_{9a}$, $R_{9b}$, $R_{10}$, $R_{11}$, $R_{12}$, $R_{13}$, $R_{14}$, $R_{15}$, X, Y and J with reference to compounds of formula I and other compounds of the invention carrying the same substituents. For any one of these substituents, any of the definitions given below may be combined with any definition of any other substituent given below or elsewhere in this document.

$Ar_1$ and $Ar_2$ are independently of each other phenyl, thienyl, pyridyl, pyrimidinyl, pyrazinyl, pyridazinyl, furanyl, wherein said phenyl, thienyl, pyridyl, pyrimidinyl, pyrazinyl, pyridazinyl, furanyl can be substituted by one to three substituents independently selected from the group consisting of hydrogen, $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_2$-$C_4$haloalkenyl, $C_2$-$C_4$haloalkynyl, $C_3$-$C_6$halocycloalkyl, $C_1$-$C_3$haloalkyl-$C_3$-$C_6$cycloalkyl, $C_3$-$C_6$halocycloalkoxy, halogen, cyano, cyano-$C_1$-$C_4$alkyl, cyano-$C_3$-$C_6$cycloalkyl nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_1$-$C_4$alkylamino, $C_2$-$C_6$dialkylamino, $C_3$-$C_6$cycloalkylamino, $C_1$-$C_4$alkyl-$C_3$-$C_6$cycloalkylamino, $C_2$-$C_4$alkylcarbonyl, CHO, $C_2$-$C_6$alkoxycarbonyl, $C_2$-$C_6$haloalkoxycarbonyl, $C_2$-$C_6$alkylaminocarbonyl, $C_2$-$C_6$haloalkylaminocarbonyl or $C_2$-$C_8$ dialkylaminocarbonyl.

Preferably, $Ar_1$ is phenyl or phenyl substituted by one to three substituents independently selected from the group consisting of hydrogen, $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_3$-$C_6$halocycloalkyl, $C_1$-$C_3$haloalkyl-$C_3$-$C_6$cycloalkyl, $C_3$-$C_6$cycloalkoxy, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_2$-$C_4$alkylcarbonyl, CHO, $C_2$-$C_6$alkoxycarbonyl, and $C_2$-$C_6$haloalkoxycarbonyl. More preferably, $Ar_1$ is phenyl or phenyl substituted by one to three substituents independently selected from the group consisting of hydrogen, $C_1$-$C_4$alkyl, $C_3$-$C_6$cycloalkyl, $C_1$-$C_4$haloalkyl, $C_3$-$C_6$halocycloalkyl, $C_1$-$C_3$haloalkyl-$C_3$-$C_6$cycloalkyl, $C_3$-$C_6$cycloalkoxy, halogen, $C_1$-$C_4$alkoxy, and $C_1$-$C_4$haloalkoxy. Even more preferably, $Ar_1$ is phenyl substituted by $C_1$-$C_4$haloalkoxy.

Preferably, $Ar_2$ is phenyl or phenyl substituted by one to three substituents independently selected from the group consisting of hydrogen, $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_3$-$C_6$halocycloalkyl, $C_1$-$C_3$haloalkyl-$C_3$-$C_6$cycloalkyl, $C_3$-$C_6$cycloalkoxy, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_2$-$C_4$alkylcarbonyl, CHO, $C_2$-$C_6$alkoxycarbonyl, $C_2$-$C_6$haloalkoxycarbonyl. More preferably, $Ar_2$ is phenyl or phenyl substituted by one to three substituents independently selected from the group consisting of hydrogen, $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_3$-$C_6$halocycloalkyl, $C_1$-$C_3$haloalkyl-$C_3$-$C_6$cycloalkyl, $C_3$-$C_6$cycloalkoxy, halogen, cyano, $C_1$-$C_4$alkoxy, $C_1$-$C_4$haloalkoxy, $C_1$-$C_4$alkylthio. Even more preferably, $Ar_2$ is phenyl substituted by one to three substituents independently selected from the group consisting of hydrogen, $C_1$-$C_4$alkyl, $C_1$-$C_4$haloalkyl, halogen, $C_1$-$C_4$alkoxy, $C_1$-$C_4$haloalkoxy.

X is a direct bond, O, S, $SO_2$, $CR_4R_5$, or $NR_6$. Preferably, X is a direct bond or O.

Y is oxygen or sulfur.

$R_1$ is hydrogen, $C_1$-$C_6$-alkyl, halo-$C_1$-$C_6$-alkyl, $C_3$-$C_6$-cycloalkyl or $C_1$-$C_3$-alkoxy. Preferably, $R_1$ is hydrogen, or $C_1$-$C_6$-alkyl.

$R_2$ and $R_3$ are independently from each other hydrogen, $C_1$-$C_6$-alkyl, $C_1$-$C_6$-haloalkyl, $C_3$-$C_6$-cycloalkyl, halo-$C_3$-$C_6$-cycloalkyl, $C_2$-$C_6$-alkenyl, $C_2$-$C_6$haloalkenyl, $C_2$-$C_6$-alkynyl, $C_2$-$C_6$haloalkynyl, $C_1$-$C_4$alkoxy-$C_1$-$C_4$alkyl, $C_1$-$C_4$haloalkylsulfinyl, $C_1$-$C_4$haloalkylsulfonyl, $C_1$-$C_4$alkylsulfinyl, $C_1$-$C_4$alkylsulfonyl, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, or $C_1$-$C_4$alkoxyimino-$C_1$-

$C_4$alkyl; provided that when $R_2$ and $R_3$ are different from hydrogen, $R_2$ and $R_3$ can be substituted by one to three substituents independently selected from the group consisting of $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_2$-$C_4$haloalkenyl, $C_2$-$C_4$haloalkynyl, $C_3$-$C_6$halocycloalkyl, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_1$-$C_4$alkylamino, $C_2$-$C_6$dialkylamino, $C_3$-$C_6$cycloalkylamino, $C_1$-$C_4$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, and $C_2$-$C_8$ dialkylaminocarbonyl;

Preferably, $R_2$ and $R_3$ are independently from each other hydrogen, $C_1$-$C_6$-alkyl, $C_1$-$C_6$-haloalkyl, $C_3$-$C_6$-cycloalkyl, halo-$C_3$-$C_6$-cycloalkyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, provided that when $R_2$ and $R_3$ groups are different from hydrogen, said $R_2$ and $R_3$ groups can be substituted by one to three substituents independently selected from the group consisting of $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_3$-$C_6$halocycloalkyl, halogen, cyano, nitro, $C_1$-$C_4$alkoxy, $C_1$-$C_4$haloalkoxy, and $C_1$-$C_4$alkylthio. More preferably, $R_2$ and $R_3$ are independently from each other hydrogen, $C_1$-$C_6$-alkyl, or $C_1$-$C_6$-haloalkyl.

$R_4$, $R_5$ and $R_6$ are independently from each other hydrogen, $C_1$-$C_6$-alkyl, halo-$C_1$-$C_6$-alkyl, $C_3$-$C_6$-cycloalkyl or $C_1$-$C_3$-alkoxy. Preferably, $R_4$, $R_5$ and $R_6$ are independently from each other hydrogen or $C_1$-$C_6$-alkyl.

J is an aromatic or a non-aromatic bicyclic ring system selected from $J_1$, $J_2$ and $J_3$

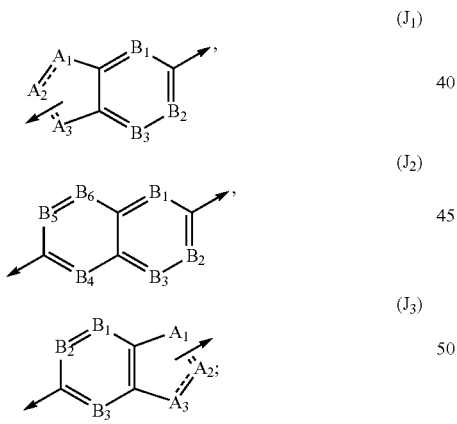

in which the arrows show the connectivity as depicted in formula (I) wherein
$A_1$ is nitrogen, N—$R_{7a}$, sulfur, oxygen or C—$R_{7b}$;
$A_2$ is nitrogen, N—$R_{8a}$, sulfur, oxygen or C—$R_{5b}$;
$A_3$ is nitrogen, N—$R_{9a}$, sulfur, oxygen or C—$R_{9b}$;
$B_1$ is nitrogen or C—$R_{10}$;
$B_2$ is nitrogen or C—$R_{11}$;
$B_3$ is nitrogen or C—$R_{12}$;
$B_4$ is nitrogen or C—$R_{13}$;
$B_5$ is nitrogen or C—$R_{14}$;
$B_6$ is nitrogen or C—$R_{15}$; with the provisos that:
a) not more than two substituents A can be oxygen or sulfur, and
b) when two substituents A are oxygen and/or sulphur, these substituents are $A_1$ and $A_3$, and $A_2$ is C—$R_{8b}$;

Preferably, J is a group selected from $J_{1'}$ to $J_{15}$:

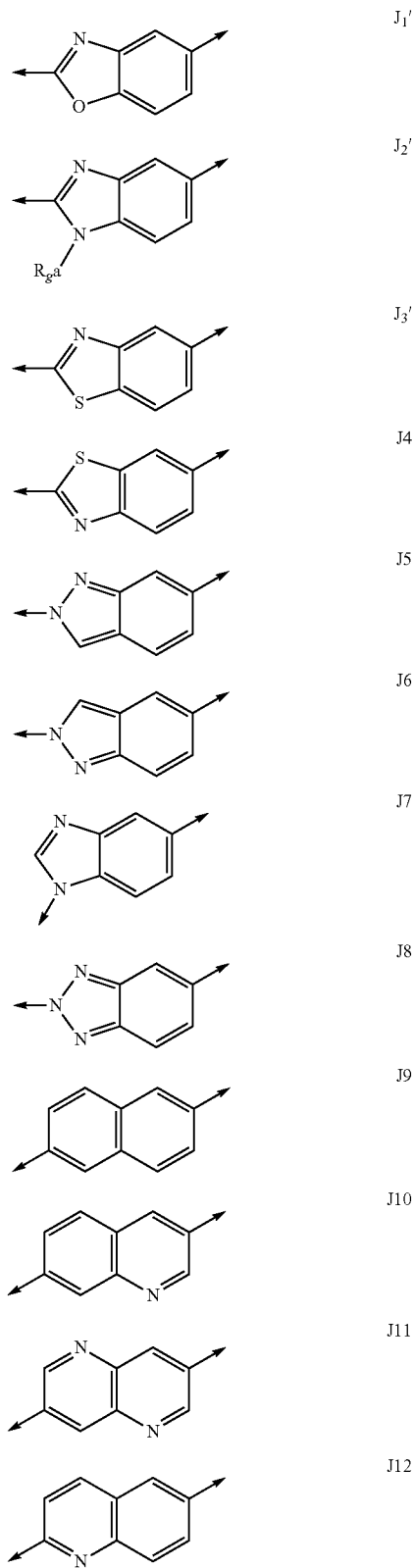

-continued
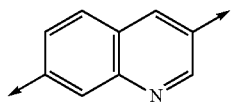
J10
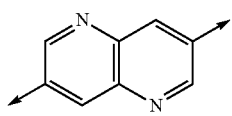
J11
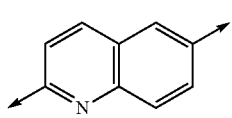
J12
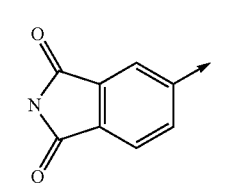
J13
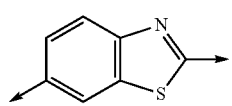
J14
More preferably, J is a group selected from:
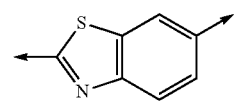
J4
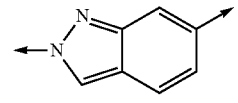
J5
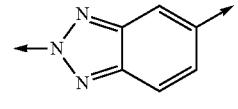
J8
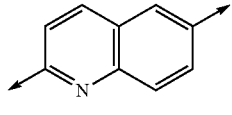
J11
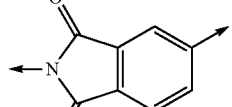
J13
Even more preferably, J is a group selected from:
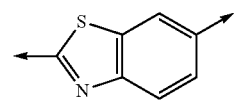
J4
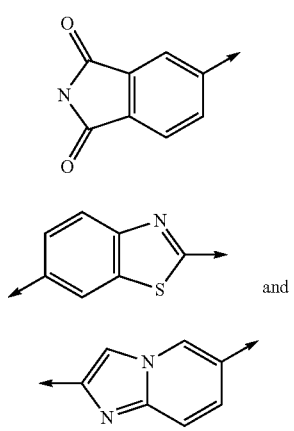
J13
J14
and
J15
Particularly preferably, J is a group selected from $J_{1'}$ to $J_{14}$:
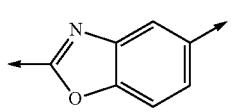
$J_1'$
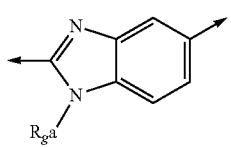
$J_2'$
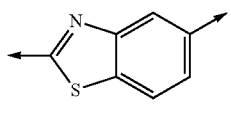
$J_3'$
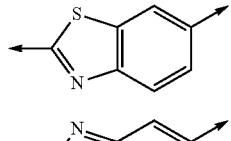
J4
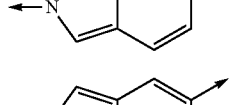
J5
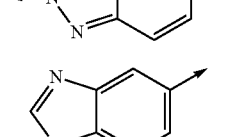
J6
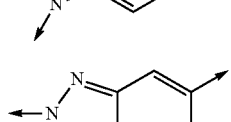
J7
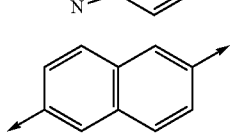
J8
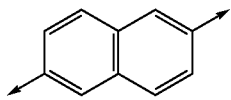
J9

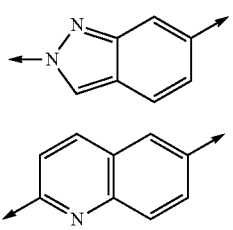

J5

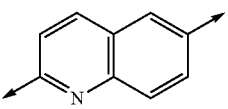

J11

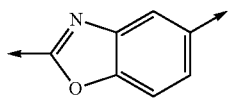

J1'

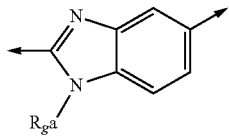

J2'

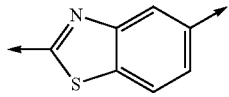

J3'

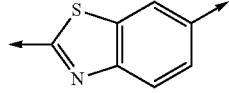

J4

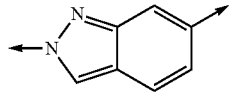

J5

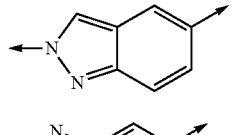

J6

Preferably the compound of formula I is a compound wherein:

$Ar_1$ is phenyl or phenyl substituted by one to three substituents independently selected from the group consisting of hydrogen, $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_3$-$C_6$halocycloalkyl, $C_1$-$C_3$haloalkyl-$C_3$-$C_6$cycloalkyl, $C_3$-$C_6$cycloalkoxy, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_2$-$C_4$alkylcarbonyl, CHO, $C_2$-$C_6$alkoxycarbonyl, or $C_2$-$C_6$haloalkoxycarbonyl;

$Ar_2$ is phenyl or phenyl substituted by one to three substituents independently selected from the group consisting of hydrogen, $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_3$-$C_6$halocycloalkyl, $C_1$-$C_3$haloalkyl-$C_3$-$C_6$cycloalkyl, $C_3$-$C_6$cycloalkoxy, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_2$-$C_4$alkylcarbonyl, CHO, $C_2$-$C_6$alkoxycarbonyl, or $C_2$-$C_6$haloalkoxycarbonyl;

X is a direct bond, O, S, $SO_2$, $CR_4R_5$, or $NR_6$;

Y is oxygen or sulfur;

$R_1$ is hydrogen, $C_1$-$C_6$-alkyl, halo-$C_1$-$C_6$-alkyl, $C_3$-$C_6$-cycloalkyl or $C_1$-$C_3$-alkoxy;

$R_2$ and $R_3$ are independently from each other hydrogen, $C_1$-$C_6$-alkyl, $C_1$-$C_6$-haloalkyl, $C_3$-$C_6$-cycloalkyl, halo-$C_3$-$C_6$-cycloalkyl, $C_2$-$C_6$-alkenyl, $C_2$-$C_6$haloalkenyl, $C_2$-$C_6$-alkynyl, $C_2$-$C_6$haloalkynyl, $C_1$-$C_4$alkoxy-$C_1$-$C_4$alkyl, $C_1$-$C_4$haloalkylsulfinyl, $C_1$-$C_4$haloalkylsulfonyl, $C_1$-$C_4$alkylsulfinyl, $C_1$-$C_4$alkylsulfonyl, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, or $C_1$-$C_4$alkoxyimino-$C_1$-$C_4$alkyl; provided that when $R_2$ and $R_3$ are different from hydrogen, $R_2$ and $R_3$ can be substituted by one to three substituents independently selected from the group consisting of $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_2$-$C_4$haloalkenyl, $C_2$-$C_4$haloalkynyl, $C_3$-$C_6$halocycloalkyl, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_1$-$C_4$alkylamino, $C_2$-$C_6$dialkylamino, $C_3$-$C_6$cycloalkylamino, $C_1$-$C_4$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, and $C_2$-$C_8$ dialkylaminocarbonyl;

$R_4$, $R_5$ and $R_6$ are independently from each other hydrogen, $C_1$-$C_6$-alkyl, halo-$C_1$-$C_6$-alkyl, $C_3$-$C_6$-cycloalkyl or $C_1$-$C_3$-alkoxy;

J is a group selected from $J_1$, to $J_{14}$;

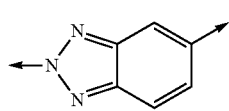

J7

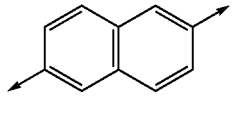

J8

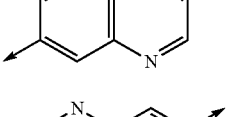

J9

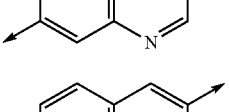

J10

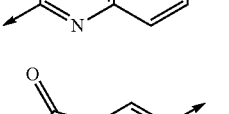

J11

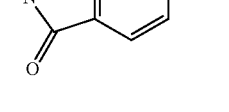

J12

J13

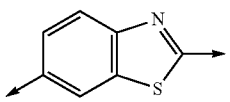
J14 wherein $R_{9a}$ is hydrogen, halogen, nitro, cyano, hydroxy, =O, CHO, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkoxy, $C_1$-$C_4$alkoxy-$C_1$-$C_4$alkoxy-$C_1$-$C_4$alkyl, $C_1$-$C_4$haloalkoxy, $C_1$-$C_4$alkylthio, $C_1$-$C_4$haloalkylthio, $C_1$-$C_4$haloalkylsulfinyl, $C_1$-$C_4$haloalkylsulfonyl, $C_1$-$C_4$alkylsulfinyl, $C_1$-$C_4$alkylsulfonyl, $C_1$-$C_4$alkylsulfonyl-$C_1$-$C_4$alkyl, $C_1$-$C_4$alkylsulfoximino-$C_1$-$C_4$alkyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, $C_1$-$C_4$alkoxyimino-$C_1$-$C_4$alkyl, —CONHSC$_2$—$C_1$-$C_6$-alkyl, —CONHSO$_2$N($C_1$-$C_6$-alkyl)$_2$, or $C_3$-$C_6$trialkylsilyl;

and agrochemically acceptable salts and enantiomers thereof.

Preferably the compound of formula I is a compound wherein:

$Ar_1$ is phenyl or phenyl substituted by one to three substituents independently selected from the group consisting of hydrogen, $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_3$-$C_6$halocycloalkyl, $C_1$-$C_3$haloalkyl-$C_3$-$C_6$cycloalkyl, $C_3$-$C_6$cycloalkoxy, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_2$-$C_4$alkylcarbonyl, CHO, $C_2$-$C_6$alkoxycarbonyl, or $C_2$-$C_6$haloalkoxycarbonyl;

$Ar_2$ is phenyl or phenyl substituted by one to three substituents independently selected from the group consisting of hydrogen, $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_3$-$C_6$halocycloalkyl, $C_1$-$C_3$haloalkyl-$C_3$-$C_6$cycloalkyl, $C_3$-$C_6$cycloalkoxy, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_2$-$C_4$alkylcarbonyl, CHO, $C_2$-$C_6$alkoxycarbonyl, or $C_2$-$C_6$haloalkoxycarbonyl;

X is a direct bond, O, S, SO$_2$, CR$_4$R$_5$, or NR$_6$;

Y is oxygen or sulfur;

$R_1$ is hydrogen, or $C_1$-$C_6$-alkyl, $R_2$ and $R_3$ are independently from each other hydrogen, $C_1$-$C_6$-alkyl, $C_1$-$C_6$-haloalkyl, $C_3$-$C_6$-cycloalkyl, halo-$C_3$-$C_6$-cycloalkyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, provided that when $R_2$ and $R_3$ groups are different from hydrogen, said $R_2$ and $R_3$ groups can be substituted by one to three substituents independently selected from the group consisting of $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_3$-$C_6$halocycloalkyl, halogen, cyano, nitro, $C_1$-$C_4$alkoxy, $C_1$-$C_4$haloalkoxy, and $C_1$-$C_4$alkylthio;

$R_4$, $R_5$ and $R_6$ are independently from each other hydrogen or $C_1$-$C_6$-alkyl;

J is a group selected from $J_{1'}$ to $J_{14}$:

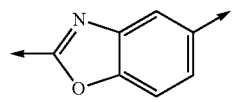
$J_1'$

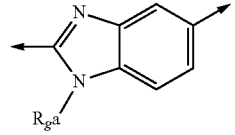
$J_2'$

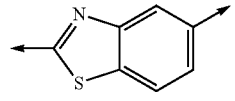
$J_3'$

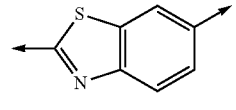
J4

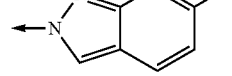
J5

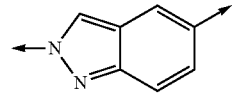
J6

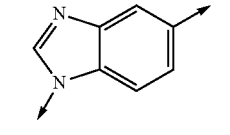
J7

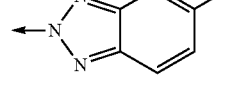
J8

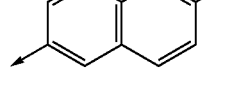
J9

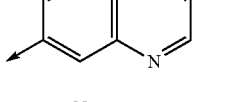
J10

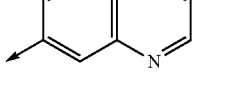
J11

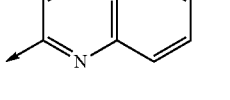
J12

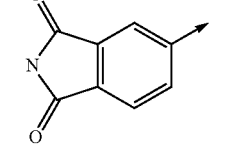
J13

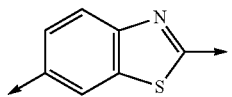  J14 wherein $R_{9a}$ is $C_1$-$C_6$alkyl or $C_1$-$C_6$haloalkyl,
and agrochemically acceptable salts and enantiomers thereof.

Preferably the compound of formula I is a compound wherein:

$Ar_1$ is phenyl or phenyl substituted by one to three substituents independently selected from the group consisting of hydrogen, $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_3$-$C_6$halocycloalkyl, $C_1$-$C_3$haloalkyl-$C_3$-$C_6$cycloalkyl, $C_3$-$C_6$cycloalkoxy, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_2$-$C_4$alkylcarbonyl, CHO, $C_2$-$C_6$alkoxycarbonyl, $C_2$-$C_6$haloalkoxycarbonyl;

$Ar_2$ is phenyl or phenyl substituted by one to three substituents independently selected from the group consisting of hydrogen, $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_3$-$C_6$halocycloalkyl, $C_1$-$C_3$haloalkyl-$C_3$-$C_6$cycloalkyl, $C_3$-$C_6$cycloalkoxy, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_2$-$C_4$alkylcarbonyl, CHO, $C_2$-$C_6$alkoxycarbonyl, and $C_2$-$C_6$haloalkoxycarbonyl;

X is a direct bond, or O;
Y is oxygen or sulfur;
$R_1$ is hydrogen, or $C_1$-$C_6$-alkyl,
$R_2$ and $R_3$ are independently from each other hydrogen, $C_1$-$C_6$-alkyl, $C_1$-$C_6$-haloalkyl, $C_3$-$C_6$-cycloalkyl, halo-$C_3$-$C_6$-cycloalkyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, provided that when $R_2$ and $R_3$ groups are different from hydrogen, said $R_2$ and $R_3$ groups can be substituted by one to three substituents independently selected from the group consisting of $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_3$-$C_6$halocycloalkyl, halogen, cyano, nitro, $C_1$-$C_4$alkoxy, $C_1$-$C_4$haloalkoxy, and $C_1$-$C_4$alkylthio;

J is a group selected from $J_1'$ to $J_{14}$:

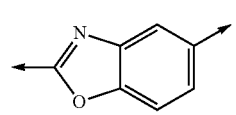  $J_1'$

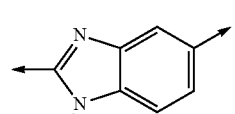  $J_2'$

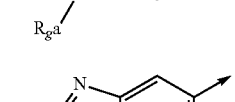  $J_3'$

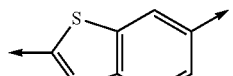  J4

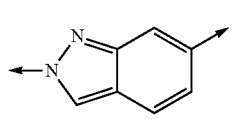  J5

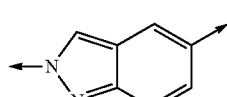  J6

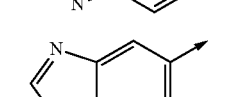  J7

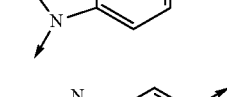  J8

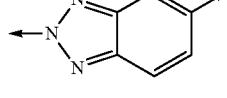  J9

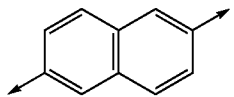  J10

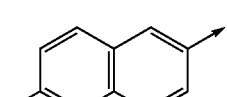  J11

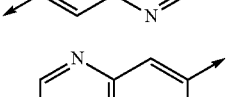  J12

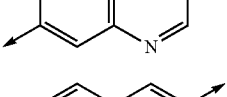  J13

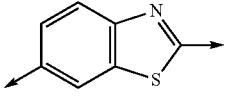  J14 each of $R_{7a}$, $R_{7b}$, $R_{8a}$, $R_{8b}$, $R_{9a}$, $R_{9b}$, $R_{10}$, $R_{11}$, $R_{12}$, $R_{13}$, $R_{14}$ and $R_{15}$, are independently from each other hydrogen, halogen, nitro, cyano, hydroxy, =O, CHO, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkoxy, $C_1$-$C_4$alkoxy-$C_1$-$C_4$alkoxy-$C_1$-$C_4$alkyl, $C_1$-$C_4$haloalkoxy, $C_1$-$C_4$alkylthio, $C_1$-$C_4$haloalkylthio, $C_1$-$C_4$haloalkylsulfinyl, $C_1$-$C_4$haloalkylsulfonyl, $C_1$-$C_4$alkylsulfinyl, $C_1$-$C_4$alkylsulfonyl, $C_1$-$C_4$alkylsulfonyl-$C_1$-$C_4$alkyl, $C_1$-$C_4$alkylsulfoximino-$C_1$-$C_4$alkyl, $C_1$-$C_4$alkylamino, $C_2$-$C_4$dialkylamino, $C_3$-$C_6$cycloalkylamino, $C_1$-$C_6$alkyl-$C_3$-

$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, $C_1$-$C_4$alkoxyimino-$C_1$-$C_4$alkyl, —CONHSC$_2$—$C_1$-$C_6$-alkyl, —CONHSO$_2$N($C_1$-$C_6$-alkyl)$_2$, or $C_3$-$C_6$trialkylsilyl;
and agrochemically acceptable salts and enantiomers thereof.

Preferably the compound of formula I is a compound wherein:

Ar$_1$ is phenyl or phenyl substituted by one to three substituents independently selected from the group consisting of hydrogen, $C_1$-$C_4$alkyl, $C_3$-$C_6$cycloalkyl, $C_1$-$C_4$haloalkyl, $C_3$-$C_6$halocycloalkyl, $C_1$-$C_3$haloalkyl-$C_3$-$C_6$cycloalkyl, $C_3$-$C_6$cycloalkoxy, halogen, $C_1$-$C_4$alkoxy, and $C_1$-$C_4$haloalkoxy;

Ar$_2$ is phenyl or phenyl substituted by one to three substituents independently selected from the group consisting of hydrogen, $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_3$-$C_6$halocycloalkyl, $C_1$-$C_3$haloalkyl-$C_3$-$C_6$cycloalkyl, $C_3$-$C_6$cycloalkoxy, halogen, cyano, $C_1$-$C_4$alkoxy, $C_1$-$C_4$haloalkoxy, $C_1$-$C_4$alkylthio.

X is a direct bond, O, S, SO$_2$, CR$_4$R$_5$, or NR$_6$;

Y is oxygen or sulfur;

R$_1$ is hydrogen, $C_1$-$C_6$-alkyl, halo-$C_1$-$C_6$-alkyl, $C_3$-$C_6$-cycloalkyl or $C_1$-$C_3$-alkoxy;

R$_2$ and R$_3$ are independently from each other hydrogen, $C_1$-$C_6$-alkyl, $C_1$-$C_6$-haloalkyl, $C_3$-$C_6$-cycloalkyl, halo-$C_3$-$C_6$-cycloalkyl, $C_2$-$C_6$-alkenyl, $C_2$-$C_6$haloalkenyl, $C_2$-$C_6$-alkynyl, $C_2$-$C_6$haloalkynyl, $C_1$-$C_4$alkoxy-$C_1$-$C_4$alkyl, $C_1$-$C_4$haloalkylsulfinyl, $C_1$-$C_4$haloalkylsulfonyl, $C_1$-$C_4$alkylsulfinyl, $C_1$-$C_4$alkylsulfonyl, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, or $C_1$-$C_4$alkoxyimino-$C_1$-$C_4$alkyl; provided that when R$_2$ and R$_3$ are different from hydrogen, R$_2$ and R$_3$ can be substituted by one to three substituents independently selected from the group consisting of $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_2$-$C_4$haloalkenyl, $C_2$-$C_4$haloalkynyl, $C_3$-$C_6$halocycloalkyl, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_1$-$C_4$alkylamino, $C_2$-$C_6$dialkylamino, $C_3$-$C_6$cycloalkylamino, $C_1$-$C_4$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, and $C_2$-$C_8$ dialkylaminocarbonyl;

R$_4$, R$_5$ and R$_6$ are independently from each other hydrogen, $C_1$-$C_6$-alkyl, halo-$C_1$-$C_6$-alkyl, $C_3$-$C_6$-cycloalkyl or $C_1$-$C_3$-alkoxy;

J is a group selected from:

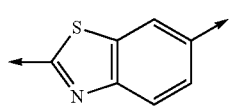

J4

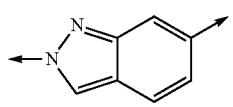

J5

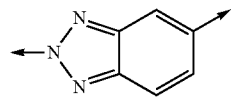

J8

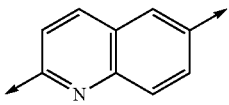

J11

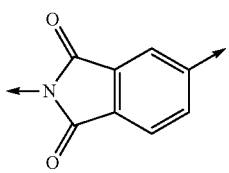

J13 and agrochemically acceptable salts and enantiomers thereof.

Preferably the compound of formula I is a compound wherein:

Ar$_1$ is phenyl or phenyl substituted by one to three substituents independently selected from the group consisting of hydrogen, $C_1$-$C_4$alkyl, $C_3$-$C_6$cycloalkyl, $C_1$-$C_4$haloalkyl, $C_3$-$C_6$halocycloalkyl, $C_1$-$C_3$haloalkyl-$C_3$-$C_6$cycloalkyl, $C_3$-$C_6$cycloalkoxy, halogen, $C_1$-$C_4$alkoxy, and $C_1$-$C_4$haloalkoxy;

Ar$_2$ is phenyl or phenyl substituted by one to three substituents independently selected from the group consisting of hydrogen, $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_3$-$C_6$halocycloalkyl, $C_1$-$C_3$haloalkyl-$C_3$-$C_6$cycloalkyl, $C_3$-$C_6$cycloalkoxy, halogen, cyano, $C_1$-$C_4$alkoxy, $C_1$-$C_4$haloalkoxy, $C_1$-$C_4$alkylthio.

X is a direct bond, O, S, SO$_2$, CR$_4$R$_5$, or NR$_6$;

Y is oxygen or sulfur;

R$_1$ is hydrogen, or $C_1$-$C_6$-alkyl;

R$_2$ and R$_3$ are independently from each other hydrogen, $C_1$-$C_6$-alkyl, $C_1$-$C_6$-haloalkyl;

R$_4$, R$_5$ and R$_6$ are independently from each other hydrogen or $C_1$-$C_6$-alkyl;

J is a group selected from:

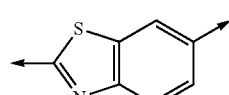

J4

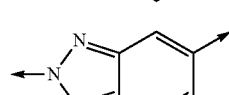

J5

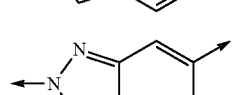

J8

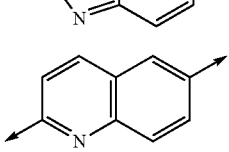

J11

-continued

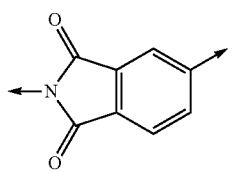
J13 and agrochemically acceptable salts and enantiomers thereof.

Preferably, the compound of formula I is a compound wherein:
Ar$_1$ is phenyl substituted by C$_1$-C$_4$haloalkoxy;
Ar$_2$ is phenyl substituted by one to three substituents independently selected from the group consisting of hydrogen, C$_1$-C$_4$alkyl, C$_1$-C$_4$haloalkyl, halogen, C$_1$-C$_4$alkoxy, C$_1$-C$_4$haloalkoxy;
X is a direct bond, O, S, SO$_2$, CR$_4$R$_5$, or NR$_6$;
Y is oxygen or sulfur;
R$_1$ is hydrogen, C$_1$-C$_6$-alkyl, halo-C$_1$-C$_6$-alkyl, C$_3$-C$_6$-cycloalkyl or C$_1$-C$_3$-alkoxy;
R$_2$ and R$_3$ are independently from each other hydrogen, C$_1$-C$_6$-alkyl, C$_1$-C$_6$-haloalkyl, C$_3$-C$_6$-cycloalkyl, halo-C$_3$-C$_6$-cycloalkyl, C$_2$-C$_6$-alkenyl, C$_2$-C$_6$haloalkenyl, C$_2$-C$_6$-alkynyl, C$_2$-C$_6$haloalkynyl, C$_1$-C$_4$alkoxy-C$_1$-C$_4$alkyl, C$_1$-C$_4$haloalkylsulfinyl, C$_1$-C$_4$haloalkylsulfonyl, C$_1$-C$_4$alkylsulfinyl, C$_1$-C$_4$alkylsulfonyl, C$_2$-C$_4$alkylcarbonyl, C$_2$-C$_6$alkoxycarbonyl, C$_2$-C$_6$alkylaminocarbonyl, C$_3$-C$_6$dialkylaminocarbonyl, C$_2$-C$_6$alkoxycarbonyloxy, C$_2$-C$_6$alkylaminocarbonyloxy, C$_3$-C$_6$dialkylaminocarbonyloxy, or C$_1$-C$_4$alkoxyimino-C$_1$-C$_4$alkyl; provided that when R$_2$ and R$_3$ are different from hydrogen, R$_2$ and R$_3$ can be substituted by one to three substituents independently selected from the group consisting of C$_1$-C$_4$alkyl, C$_2$-C$_4$alkenyl, C$_2$-C$_4$alkynyl, C$_3$-C$_6$cycloalkyl, C$_1$-C$_4$haloalkyl, C$_2$-C$_4$haloalkenyl, C$_2$-C$_4$haloalkynyl, C$_3$-C$_6$halocycloalkyl, halogen, cyano, nitro, C$_1$-C$_4$alkoxy, C$_1$-C$_4$haloalkoxy, C$_1$-C$_4$alkylthio, C$_1$-C$_4$alkylsulfinyl, C$_1$-C$_4$alkylsulfonyl, C$_1$-C$_4$alkylsulfoximino, C$_1$-C$_4$alkylamino, C$_2$-C$_6$dialkylamino, C$_3$-C$_6$cycloalkylamino, C$_1$-C$_4$alkyl-C$_3$-C$_6$cycloalkylamino, C$_2$-C$_4$alkylcarbonyl, C$_2$-C$_6$alkoxycarbonyl, C$_2$-C$_6$alkylaminocarbonyl, and C$_2$-C$_8$ dialkylaminocarbonyl;
R$_4$, R$_5$ and R$_6$ are independently from each other hydrogen, C$_1$-C$_6$-alkyl, halo-C$_1$-C$_6$-alkyl, C$_3$-C$_6$-cycloalkyl or C$_1$-C$_3$-alkoxy;
J is a group selected from:

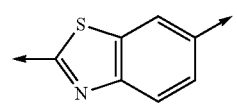
J4

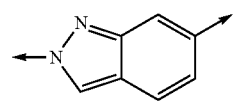
J5

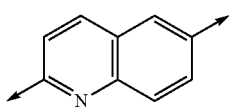
J11 and agrochemically acceptable salts and enantiomers thereof.

Preferably the compound of formula I is a compound wherein:
Ar$_1$ is phenyl substituted by C$_1$-C$_4$haloalkoxy;
Ar$_2$ is phenyl substituted by one to three substituents independently selected from the group consisting of hydrogen, C$_1$-C$_4$alkyl, C$_1$-C$_4$haloalkyl, halogen, C$_1$-C$_4$alkoxy, C$_1$-C$_4$haloalkoxy;
X is a direct bond or O;
Y is oxygen or sulfur;
R$_1$ is hydrogen or C$_1$-C$_6$-alkyl,
R$_2$ and R$_3$ are independently from each other hydrogen, C$_1$-C$_6$-alkyl, C$_1$-C$_6$-haloalkyl
J is a group selected from:

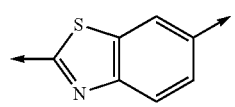
J4

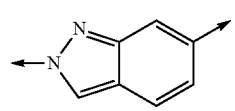
J5

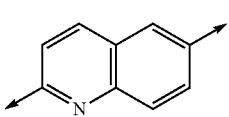
J11 and agrochemically acceptable salts and enantiomers thereof.

Even more preferably, the compound of formula (I) is the compound P1, P2 or P3 below:

1-(2,6-dimethylphenyl)-3-[[2-[4-(trifluoromethoxy)phenyl]indazol-6-yl]methyleneamino]thiourea, 1-(2,6-dimethylphenyl)-3-[[2-[4-(trifluoromethoxy)phenoxy]-6-quinolyl]methyleneamino]thiourea, 1-(2-isopropylphenyl)-3[[2-[4-(trifluoromethoxy)phenoxy]-1,3-benzothiazol-5-yl]methyleneamino]thiourea.

The invention also relates to compounds of formula (IV), (VI), (VIa), (VIb), (VIc), (VId), (VIe), (VIf), (XV) and (XXI) as shown below, wherein Ar$_1$, Ar$_2$, R$_1$, R$_2$, J, A$_1$, A$_2$, B$_1$, B$_2$, B$_3$, B$_4$, B$_5$ and B$_6$ are as defined for formula I. These compounds, including salts or N-oxides thereof, are useful as intermediates in the synthesis of compounds of formula I. Preferred definitions of Ar$_1$, Ar$_2$, R$_1$, R$_2$, J, A$_1$, A$_2$, B$_1$, B$_2$, B$_3$, B$_4$, B$_5$ and B$_6$ are as defined for formula I.

The process according to the invention for preparing compounds of formula I is carried out in principle by methods known to those skilled in the art. More specifically, compounds of formula (I) can be prepared, as depicted in scheme 1, by reacting compounds of formula (II) with compounds of formula (III), wherein LG is a leaving group such as halogen, preferentially chlorine, bromine or iodine, or a sulfonate, like for example a methanesulfonate or a trifluoromethanesulfonate in the presence or in the absence of a base, like sodium carbonate or triethylamine, in a solvent or a solvent mixture, like, for tetrahydrofuran, DMF, dioxane or acetonitrile. The reaction temperature can preferentially range from room temperature to the boiling point of the reaction mixture. In formula (I), (II) and (III), Ar$_1$, X, J, R$_1$, R$_2$, Y, R$_3$ and Ar$_2$ are as described above.

Scheme 1

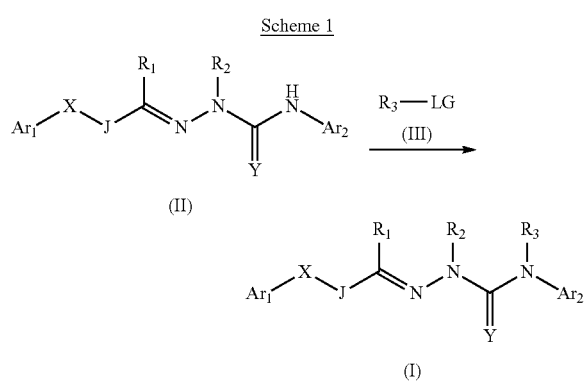

Compounds of formula (II) can be prepared, as depicted in scheme 2, by reacting compounds of formula (IV) with compounds of formula (V), in the presence or in the absence of a base such as triethylamine or N,N-diisopropylethylamine, in a solvent or a solvent mixture, like, for tetrahydrofuran, DMF, dioxane or acetonitrile. The reaction temperature can preferentially range from room temperature to the boiling point of the reaction mixture. Compounds of formula (V) are isocyanates (Y is O) or isothiocyanates (Y is S) and can be prepared by methods known to those skilled in the art (see e.g. M. Smith, J. March, March's Advanced Organic Chemistry, 6$^{th}$ edition, Wiley, 2007). In formula (II), (IV) and (V), $Ar_1$, X, J, $R_1$, $R_2$, Y and $Ar_2$ are as described above.

Scheme 2

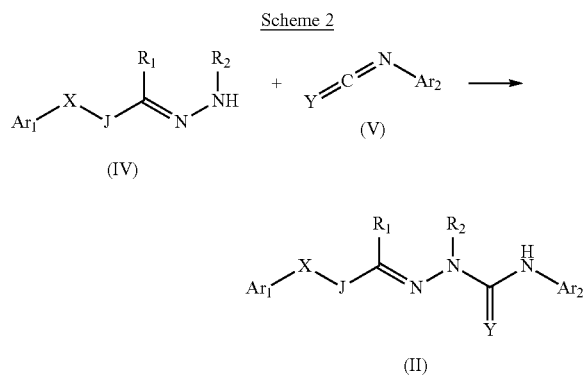

Compounds of formula (IV) can be prepared, as depicted in scheme 3, by reacting compounds of formula (VI) with compounds of formula (VII), by methods known to those skilled in the art (see e.g. M. Smith, J. March, March's Advanced Organic Chemistry, 6$^{th}$ edition, Wiley, 2007). Compounds of formula (VII) can be prepared by methods known to those skilled in the art (see e.g. M. Smith, J. March, March's Advanced Organic Chemistry, 6$^{th}$ edition, Wiley, 2007). In formula (IV), (VI) and (VII), $Ar_1$, X, J, $R_1$ and $R_2$, are as described above.

Scheme 3

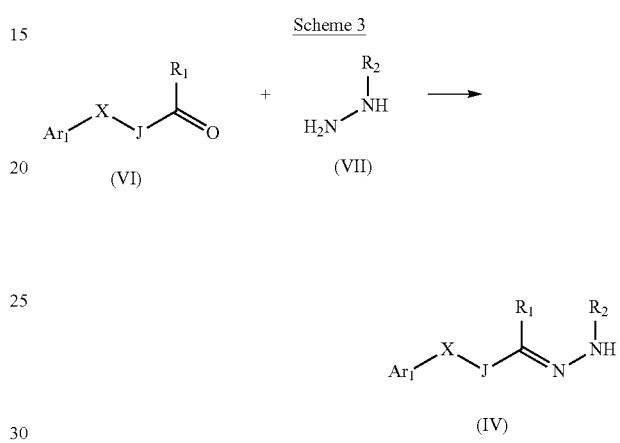

Compounds of formula (VI) can be prepared according to several methods known to those skilled in the art.

More specifically, compounds of formula (VIa) can be prepared according to scheme 4. Compound of formula (VIII) reacts with a compound of formula (IX) (T is e.g. Cl, Br, I, OTf, OMes) under Cu(I) catalysis in the presence of a ligand such as proline or N,N'-dimethylethylenediamine. There are several way of elaborating the methyl group of compound of formula (X) to the aldehyde of formula (VIa) as depicted in scheme 4, using methods known to those skilled in the art (see e.g. M. Smith, J. March, March's Advanced Organic Chemistry, 6$^{th}$ edition, Wiley, 2007). In formula (VIa), (VIII), (IX), (X), (XI), (XII) and (XIII), $A_1$, $A_3$ and $Ar_1$ are as described above.

Scheme 4

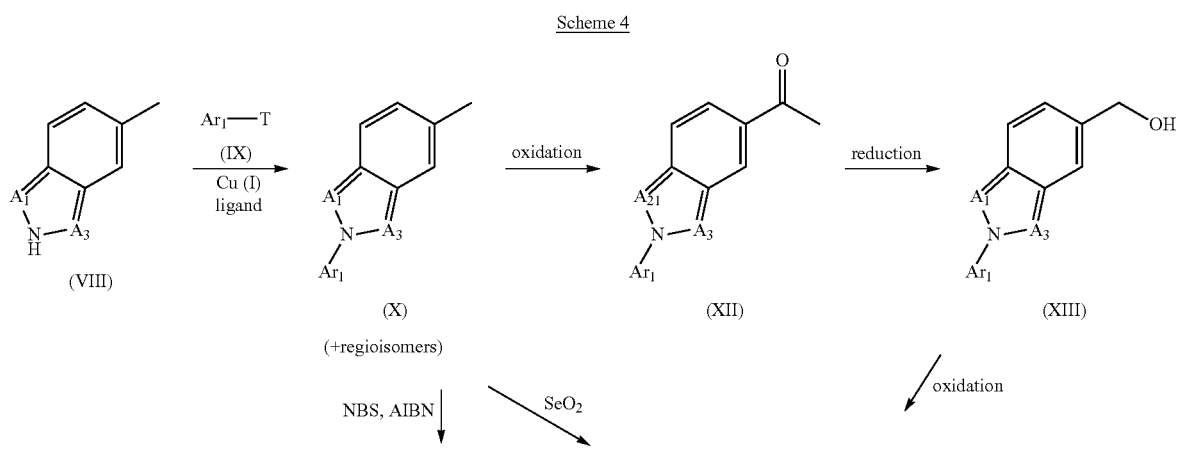

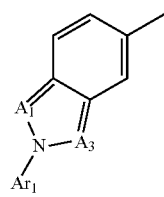

(XI)

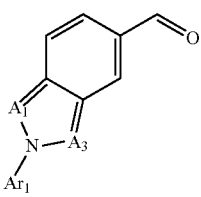

(VIa)

Compounds of formula (VIb) can be prepared according to scheme 5. Compounds of formula (XIV) or (XVI) are reacted with a compound of formula (IX) (T is e.g. Cl, Br, I, OTf, OMes) under Cu(I) catalysis in the presence of a ligand such as proline or N,N'-dimethylethylenediamine. Addition of a compound of formula $R_1$-M (M is e.g. MgCl, MgBr, Li, ZnCl) to compounds of formula (XV) or (XVII) gives compounds of formula (VIb). In formula (VIb), (IX), (XIV), (XV), (XVI) and (XVII), $A_1$, $A_3$ and $R_1$ are as defined above.

Scheme 6

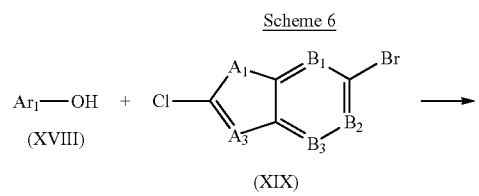

(XVIII)         (XIX)

Scheme 5

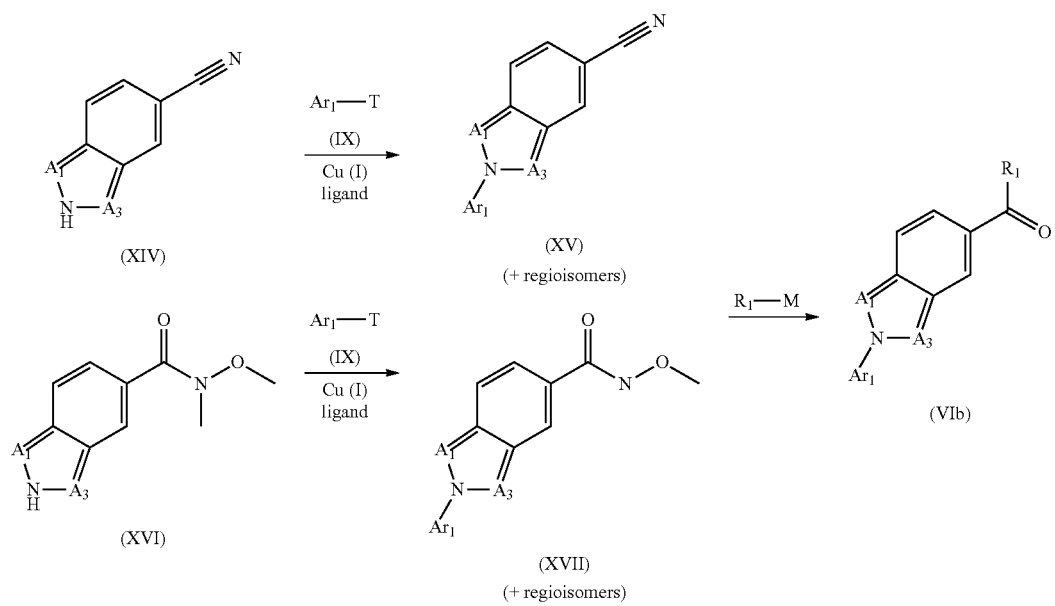

Compounds of formula (VIc) and (VId) can be prepared according to scheme 6. Compounds of formula (XVIII) can be reacted with a compound of formula (XIX) in a presence of a base such as NaH to give compounds of formula (XX). Compounds of formula (XX) can be metalated with an agent such as n-BuLi or iPrMgCl and reacted with a formylating agent such as DMF to give a compound of formula (VIc). Alternatively, compounds of formula (XX) can be reacted with a cyanation agent such as CuCN or $Zn(CN)_2$ in the presence of a catalyst such as $Pd(PPh_3)_4$ or CuI to give compounds of formula (XXI). Compounds of formula (XXI) can be elaborated to compounds of formula (VId) in the same manner as compounds of formula (XV) are elaborated to compounds of formula (VIb) as depicted in schemes 5 and 6. In formula (VIc), (VId), (XVIII) (XIX) (XX) and (XXI), $A_1$, $A_3$, $B_1$, $B_2$, $B_3$ and $R_1$ are as defined above.

-continued

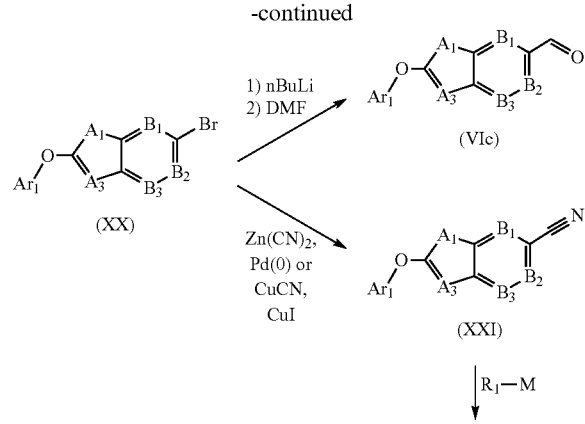

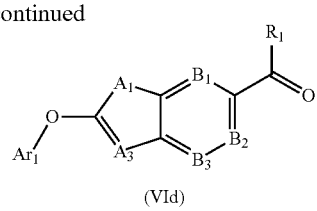

(VId)

Compounds of formula (VIe) and (VIf) can be prepared according to scheme 7. Compounds of formula (XVIII) can be reacted with a compound of formula (XXII) in a presence of a base such as NaH to give compounds of formula (XXIII). Compounds of formula (XXIII) can be metalated with an agent such as n-BuLi or iPrMgCl and reacted with a formylating agent such as DMF to give compounds of formula (VIe). Alternatively, compounds of formula (XXIII) can be reacted with a cyanation agent such as CuCN or $Zn(CN)_2$ in the presence of a catalyst such as $Pd(PPh_3)_4$ or CuI to give compounds of formula (XXIV). Compounds of formula (XXIV) can be elaborated to compounds of formula (VIf) in the same manner as compounds of formula (XV) are elaborated to compounds of formula (VIb) as depicted in schemes 5 and 7. In formula (VIe), (VIf), (XVIII), (XXII) (XXIII) and (XXIV), $Ar_1$, $B_1$, $B_2$, $B_3$, $B_4$, $B_5$, $B_6$ and $R_1$ are as defined above. Hal1 and Hal2 are independently Cl, Br, I.

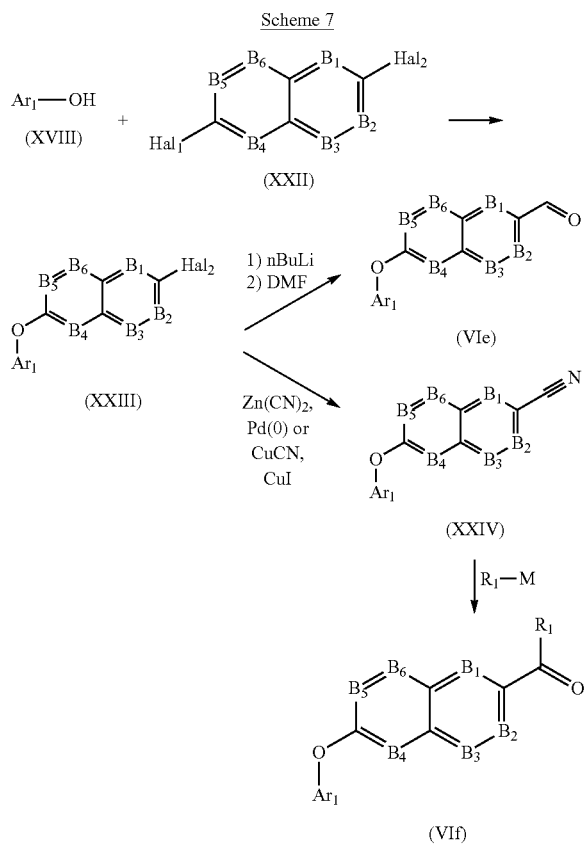

The compounds according to the following Tables 1 to 13 below can be prepared according to the methods described above. The examples which follow are intended to illustrate the invention and show preferred compounds of formula I.

Depending on the procedure or the reaction conditions, the compounds of formula I, which have salt-forming properties can be obtained in free form or in the form of salts.

The compounds of formula I and, where appropriate, the tautomers thereof, in each case in free form or in salt form, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

Diastereomer mixtures or racemate mixtures of compounds of formula I, in free form or in salt form, which can be obtained depending on which starting materials and procedures have been chosen can be separated in a known manner into the pure diasteromers or racemates on the basis of the physicochemical differences of the components, for example by fractional crystallization, distillation and/or chromatography.

Enantiomer mixtures, such as racemates, which can be obtained in a similar manner can be resolved into the optical antipodes by known methods, for example by recrystallization from an optically active solvent, by chromatography on chiral adsorbents, for example high-performance liquid chromatography (HPLC) on acetyl cellulose, with the aid of suitable microorganisms, by cleavage with specific, immobilized enzymes, via the formation of inclusion compounds, for example using chiral crown ethers, where only one enantiomer is complexed, or by conversion into diastereomeric salts, for example by reacting a basic end-product racemate with an optically active acid, such as a carboxylic acid, for example camphor, tartaric or malic acid, or sulfonic acid, for example camphorsulfonic acid, and separating the diastereomer mixture which can be obtained in this manner, for example by fractional crystallization based on their differing solubilities, to give the diastereomers, from which the desired enantiomer can be set free by the action of suitable agents, for example basic agents.

Pure diastereomers or enantiomers can be obtained according to the invention not only by separating suitable isomer mixtures, but also by generally known methods of diastereoselective or enantioselective synthesis, for example by carrying out the process according to the invention with starting materials of a suitable stereochemistry.

N-oxides can be prepared by reacting a compound of the formula I with a suitable oxidizing agent, for example the $H_2O_2$/urea adduct in the presence of an acid anhydride, e.g. trifluoroacetic anhydride. Such oxidations are known from the literature, for example from *J. Med. Chem.* 1989, 32, 2561 or WO 2000/15615.

It is advantageous to isolate or synthesize in each case the biologically more effective isomer, for example enantiomer or diastereomer, or isomer mixture, for example enantiomer mixture or diastereomer mixture, if the individual components have a different biological activity.

The compounds of formula I and, where appropriate, the tautomers thereof, in each case in free form or in salt form, can, if appropriate, also be obtained in the form of hydrates and/or include other solvents, for example those which may have been used for the crystallization of compounds which are present in solid form.

Table X: This table discloses 100 substituent definitions X.001 to X.100 of the formula I-1a:

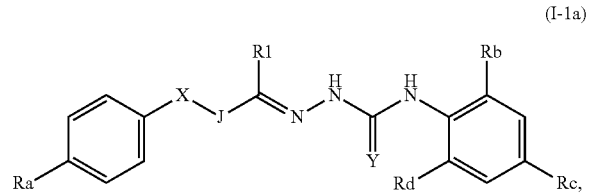

wherein $R_a$, X, $R_1$, Y, $R_b$, $R_c$ and $R_d$ are as defined below:

TABLE X

| Comp. No | $R_a$ | X | $R_1$ | Y | $R_b$ | $R_c$ | $R_d$ |
|---|---|---|---|---|---|---|---|
| X. 001 | OCF$_3$ | Direct bond | H | O | CH$_3$ | H | CH$_3$ |
| X. 002 | OCF$_3$ | Direct bond | H | O | iPr | H | H |
| X. 003 | OCF$_3$ | Direct bond | H | O | CH$_3$ | OCH$_3$ | CH$_3$ |
| X. 004 | OCF$_3$ | Direct bond | H | O | CH$_3$ | H | Cl |
| X. 005 | OCF$_3$ | Direct bond | H | O | CH$_3$ | OCH$_3$ | Cl |
| X. 006 | OCF$_3$ | Direct bond | H | O | Cl | H | Cl |
| X. 007 | OCF$_3$ | Direct bond | H | O | Cl | H | F |
| X. 008 | OCF$_3$ | Direct bond | H | O | CH$_3$ | H | H |
| X. 009 | OCF$_3$ | Direct bond | H | O | Cl | H | H |
| X. 010 | OCF$_3$ | Direct bond | H | O | CH$_3$ | OCH$_3$ | H |
| X. 011 | OCF$_2$CF$_3$ | Direct bond | H | O | CH$_3$ | H | CH$_3$ |
| X. 012 | OCF$_2$CF$_3$ | Direct bond | H | O | iPr | H | H |
| X. 013 | OCF$_2$CF$_3$ | Direct bond | H | O | CH$_3$ | OCH$_3$ | CH$_3$ |
| X. 014 | OCF$_2$CF$_3$ | Direct bond | H | O | CH$_3$ | H | Cl |
| X. 015 | OCF$_2$CF$_3$ | Direct bond | H | O | CH$_3$ | OCH$_3$ | Cl |
| X. 016 | OCF$_2$CF$_3$ | Direct bond | H | O | Cl | H | Cl |
| X. 017 | OCF$_2$CF$_3$ | Direct bond | H | O | Cl | H | F |
| X. 018 | OCF$_2$CF$_3$ | Direct bond | H | O | CH$_3$ | H | H |
| X. 019 | OCF$_2$CF$_3$ | Direct bond | H | O | Cl | H | H |
| X. 020 | OCF$_2$CF$_3$ | Direct bond | H | O | CH$_3$ | OCH$_3$ | H |
| X. 021 | OCF$_3$ | O | H | O | CH$_3$ | H | CH$_3$ |
| X. 022 | OCF$_3$ | O | H | O | iPr | H | H |
| X. 023 | OCF$_3$ | O | H | O | CH$_3$ | OCH$_3$ | CH$_3$ |
| X. 024 | OCF$_3$ | O | H | O | CH$_3$ | H | Cl |
| X. 025 | OCF$_3$ | O | H | O | CH$_3$ | OCH$_3$ | Cl |
| X. 026 | OCF$_3$ | O | H | O | Cl | H | Cl |
| X. 027 | OCF$_3$ | O | H | O | Cl | H | F |
| X. 028 | OCF$_3$ | O | H | O | CH$_3$ | H | H |
| X. 029 | OCF$_3$ | O | H | O | Cl | H | H |
| X. 030 | OCF$_3$ | O | H | O | CH$_3$ | OCH$_3$ | H |
| X. 031 | OCF$_3$ | O | CH$_3$ | O | CH$_3$ | H | CH$_3$ |
| X. 032 | OCF$_3$ | O | CH$_3$ | O | iPr | H | H |
| X. 033 | OCF$_3$ | O | CH$_3$ | O | CH$_3$ | OCH$_3$ | CH$_3$ |
| X. 034 | OCF$_3$ | O | CH$_3$ | O | CH$_3$ | H | Cl |
| X. 035 | OCF$_3$ | O | CH$_3$ | O | CH$_3$ | OCH$_3$ | Cl |
| X. 036 | OCF$_3$ | O | CH$_3$ | O | Cl | H | Cl |
| X. 037 | OCF$_3$ | O | CH$_3$ | O | Cl | H | F |
| X. 038 | OCF$_3$ | O | CH$_3$ | O | CH$_3$ | H | H |
| X. 039 | OCF$_3$ | O | CH$_3$ | O | Cl | H | H |
| X. 040 | OCF$_3$ | O | CH$_3$ | O | CH$_3$ | OCH$_3$ | H |
| X. 041 | OCF$_3$ | Direct bond | CH$_3$ | O | CH$_3$ | H | CH$_3$ |
| X. 042 | OCF$_3$ | Direct bond | CH$_3$ | O | iPr | H | H |
| X. 043 | OCF$_3$ | Direct bond | CH$_3$ | O | CH$_3$ | OCH$_3$ | CH$_3$ |
| X. 044 | OCF$_3$ | Direct bond | CH$_3$ | O | CH$_3$ | H | Cl |
| X. 045 | OCF$_3$ | Direct bond | CH$_3$ | O | CH$_3$ | OCH$_3$ | Cl |
| X. 046 | OCF$_3$ | Direct bond | CH$_3$ | O | Cl | H | Cl |
| X. 047 | OCF$_3$ | Direct bond | CH$_3$ | O | Cl | H | F |
| X. 048 | OCF$_3$ | Direct bond | CH$_3$ | O | CH$_3$ | H | H |
| X. 049 | OCF$_3$ | Direct bond | CH$_3$ | O | Cl | H | H |
| X. 050 | OCF$_3$ | Direct bond | CH$_3$ | O | CH$_3$ | OCH$_3$ | H |
| X. 051 | OCF$_3$ | Direct bond | H | S | CH$_3$ | H | CH$_3$ |
| X. 052 | OCF$_3$ | Direct bond | H | S | iPr | H | H |
| X. 053 | OCF$_3$ | Direct bond | H | S | CH$_3$ | OCH$_3$ | CH$_3$ |
| X. 054 | OCF$_3$ | Direct bond | H | S | CH$_3$ | H | Cl |
| X. 055 | OCF$_3$ | Direct bond | H | S | CH$_3$ | OCH$_3$ | Cl |
| X. 056 | OCF$_3$ | Direct bond | H | S | Cl | H | Cl |
| X. 057 | OCF$_3$ | Direct bond | H | S | Cl | H | F |
| X. 058 | OCF$_3$ | Direct bond | H | S | CH$_3$ | H | H |
| X. 059 | OCF$_3$ | Direct bond | H | S | Cl | H | H |
| X. 060 | OCF$_3$ | Direct bond | H | S | CH$_3$ | OCH$_3$ | H |
| X. 061 | OCF$_2$CF$_3$ | Direct bond | H | S | CH$_3$ | H | CH$_3$ |
| X. 062 | OCF$_2$CF$_3$ | Direct bond | H | S | iPr | H | H |
| X. 063 | OCF$_2$CF$_3$ | Direct bond | H | S | CH$_3$ | OCH$_3$ | CH$_3$ |
| X. 064 | OCF$_2$CF$_3$ | Direct bond | H | S | CH$_3$ | H | Cl |
| X. 065 | OCF$_2$CF$_3$ | Direct bond | H | S | CH$_3$ | OCH$_3$ | Cl |
| X. 066 | OCF$_2$CF$_3$ | Direct bond | H | S | Cl | H | Cl |
| X. 067 | OCF$_2$CF$_3$ | Direct bond | H | S | Cl | H | F |
| X. 068 | OCF$_2$CF$_3$ | Direct bond | H | S | CH$_3$ | H | H |
| X. 069 | OCF$_2$CF$_3$ | Direct bond | H | S | Cl | H | H |
| X. 070 | OCF$_2$CF$_3$ | Direct bond | H | S | CH$_3$ | OCH$_3$ | H |
| X. 071 | OCF$_3$ | O | H | S | CH$_3$ | H | CH$_3$ |
| X. 072 | OCF$_3$ | O | H | S | iPr | H | H |
| X. 073 | OCF$_3$ | O | H | S | CH$_3$ | OCH$_3$ | CH$_3$ |
| X. 074 | OCF$_3$ | O | H | S | CH$_3$ | H | Cl |
| X. 075 | OCF$_3$ | O | H | S | CH$_3$ | OCH$_3$ | Cl |
| X. 076 | OCF$_3$ | O | H | S | Cl | H | Cl |
| X. 077 | OCF$_3$ | O | H | S | Cl | H | F |
| X. 078 | OCF$_3$ | O | H | S | CH$_3$ | H | H |
| X. 079 | OCF$_3$ | O | H | S | Cl | H | H |
| X. 080 | OCF$_3$ | O | H | S | CH$_3$ | OCH$_3$ | H |
| X. 081 | OCF$_3$ | O | CH$_3$ | S | CH$_3$ | H | CH$_3$ |
| X. 082 | OCF$_3$ | O | CH$_3$ | S | iPr | H | H |
| X. 083 | OCF$_3$ | O | CH$_3$ | S | CH$_3$ | OCH$_3$ | CH$_3$ |
| X. 084 | OCF$_3$ | O | CH$_3$ | S | CH$_3$ | H | Cl |
| X. 085 | OCF$_3$ | O | CH$_3$ | S | CH$_3$ | OCH$_3$ | Cl |
| X. 086 | OCF$_3$ | O | CH$_3$ | S | Cl | H | Cl |
| X. 087 | OCF$_3$ | O | CH$_3$ | S | Cl | H | F |
| X. 088 | OCF$_3$ | O | CH$_3$ | S | CH$_3$ | H | H |
| X. 089 | OCF$_3$ | O | CH$_3$ | S | Cl | H | H |
| X. 090 | OCF$_3$ | O | CH$_3$ | S | CH$_3$ | OCH$_3$ | H |
| X. 091 | OCF$_3$ | Direct bond | CH$_3$ | S | CH$_3$ | H | CH$_3$ |
| X. 092 | OCF$_3$ | Direct bond | CH$_3$ | S | iPr | H | H |
| X. 093 | OCF$_3$ | Direct bond | CH$_3$ | S | CH$_3$ | OCH$_3$ | CH$_3$ |
| X. 094 | OCF$_3$ | Direct bond | CH$_3$ | S | CH$_3$ | H | Cl |
| X. 095 | OCF$_3$ | Direct bond | CH$_3$ | S | CH$_3$ | OCH$_3$ | Cl |
| X. 096 | OCF$_3$ | Direct bond | CH$_3$ | S | Cl | H | Cl |
| X. 097 | OCF$_3$ | Direct bond | CH$_3$ | S | Cl | H | F |
| X. 098 | OCF$_3$ | Direct bond | CH$_3$ | S | CH$_3$ | H | H |
| X. 099 | OCF$_3$ | Direct bond | CH$_3$ | S | Cl | H | H |
| X. 100 | OCF$_3$ | Direct bond | CH$_3$ | S | CH$_3$ | OCH$_3$ | H | and the N-oxides of the compounds of Table X.

Table 1: This table discloses the 100 compounds 1.001 to 1.100 of the formula 1-1, wherein $R_a$, X, $R_1$, Y, $R_b$, $R_c$ and $R_d$ are as defined in Table X.

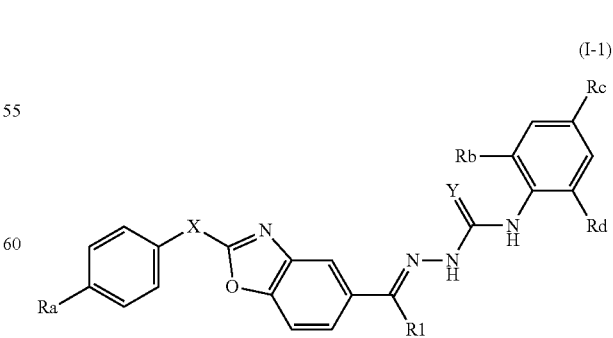

For example, compound No. 1.001 has the following structure:

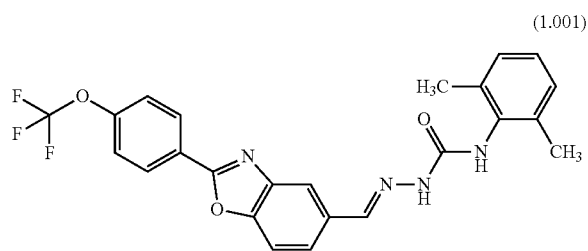 [SMILES: Cc1cccc(C)c1NC(=O)N/N=C/c1ccc2oc(-c3ccc(OC(F)(F)F)cc3)nc2c1]

(1.001)

Table 2: This table discloses the 100 compounds 2.001 to 2.100 of the formula 1-2, wherein $R_a$, X, $R_1$, Y, $R_b$, $R_c$ and $R_d$ are as defined in Table X.

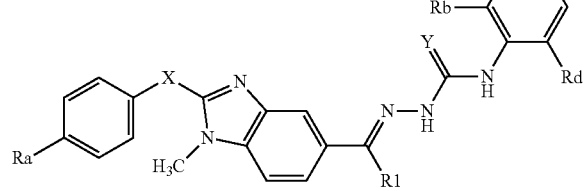

(I-2)

Table 3: This table discloses the 100 compounds 3.001 to 3.100 of the formula 1-3, wherein $R_a$, X, $R_1$, Y, $R_b$, $R_c$ and $R_d$ are as defined in Table X.

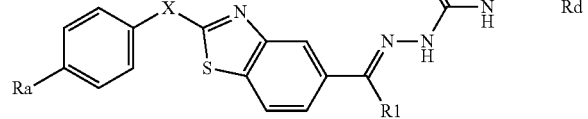

(I-3)

Table 4: This table discloses the 100 compounds 4.001 to 4.100 of the formula 1-4, wherein $R_a$, X, $R_1$, Y, $R_b$, $R_c$ and $R_d$ are as defined in Table X.

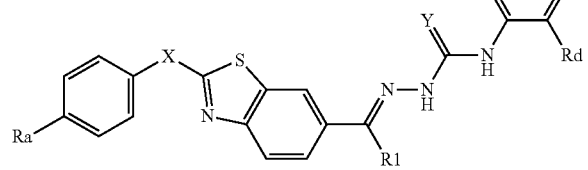

(I-4)

Table 5: This table discloses the 100 compounds 5.001 to 5.100 of the formula 1-5, wherein $R_a$, X, $R_1$, Y, $R_b$, $R_c$ and $R_d$ are as defined in Table X.

(I-5)

Table 6: This table discloses the 100 compounds 6.001 to 6.100 of the formula 1-6, wherein $R_a$, X, $R_1$, Y, $R_b$, $R_c$ and $R_d$ are as defined in Table X.

(I-6)

Table 7: This table discloses the 100 compounds 7.001 to 7.100 of the formula 1-7, wherein $R_a$, X, $R_1$, Y, $R_b$, $R_c$ and $R_d$ are as defined in Table X.

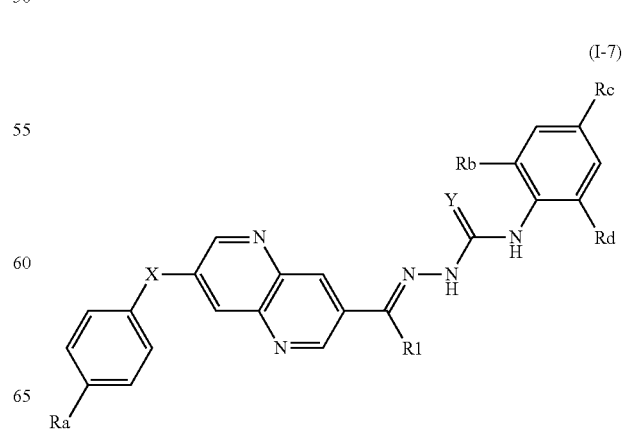

(I-7)

Table 8: This table discloses the 100 compounds 8.001 to 8.100 of the formula 1-8, wherein $R_a$, X, $R_1$, Y, $R_b$, $R_c$ and $R_d$ are as defined in Table X.

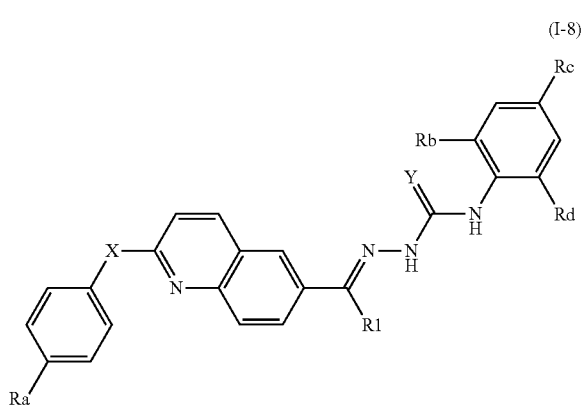

(I-8)

Table Y: This table discloses 60 substituent definitions Y.001 to Y.060 of the formula I-1b:

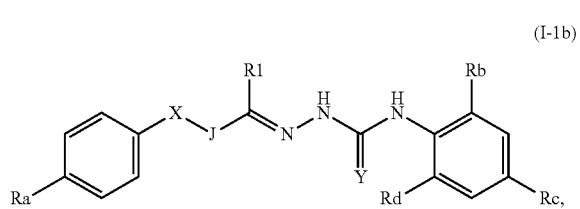

(I-1b)

wherein $R_a$, X, $R_1$, $R_b$, $R_c$ and $R_d$ are as defined below:

TABLE Y

| Comp. No | $R_a$ | $R_1$ | Y | $R_b$ | $R_c$ | $R_d$ |
|---|---|---|---|---|---|---|
| Y. 001 | OCF$_3$ | H | O | CH$_3$ | H | CH$_3$ |
| Y. 002 | OCF$_3$ | H | O | iPr | H | H |
| Y. 003 | OCF$_3$ | H | O | CH$_3$ | OCH$_3$ | CH$_3$ |
| Y. 004 | OCF$_3$ | H | O | CH$_3$ | H | Cl |
| Y. 005 | OCF$_3$ | H | O | CH$_3$ | OCH$_3$ | Cl |
| Y. 006 | OCF$_3$ | H | O | Cl | H | Cl |
| Y. 007 | OCF$_3$ | H | O | Cl | H | F |
| Y. 008 | OCF$_3$ | H | O | CH$_3$ | H | H |
| Y. 009 | OCF$_3$ | H | O | Cl | H | H |
| Y. 010 | OCF$_3$ | H | O | CH$_3$ | OCH$_3$ | H |
| Y. 011 | OCF$_2$CF$_3$ | H | O | CH$_3$ | H | CH$_3$ |
| Y. 012 | OCF$_2$CF$_3$ | H | O | iPr | H | H |
| Y. 013 | OCF$_2$CF$_3$ | H | O | CH$_3$ | OCH$_3$ | CH$_3$ |
| Y. 014 | OCF$_2$CF$_3$ | H | O | CH$_3$ | H | Cl |
| X. 015 | OCF$_2$CF$_3$ | H | O | CH$_3$ | OCH$_3$ | Cl |
| Y. 016 | OCF$_2$CF$_3$ | H | O | Cl | H | Cl |
| Y. 017 | OCF$_2$CF$_3$ | H | O | Cl | H | F |
| Y. 018 | OCF$_2$CF$_3$ | H | O | CH$_3$ | H | H |
| Y. 019 | OCF$_2$CF$_3$ | H | O | Cl | H | H |
| Y. 020 | OCF$_2$CF$_3$ | H | O | CH$_3$ | OCH$_3$ | H |
| Y. 021 | OCF$_3$ | CH$_3$ | O | CH$_3$ | H | CH$_3$ |
| Y. 022 | OCF$_3$ | CH$_3$ | O | iPr | H | H |
| Y. 023 | OCF$_3$ | CH$_3$ | O | CH$_3$ | OCH$_3$ | CH$_3$ |
| Y. 024 | OCF$_3$ | CH$_3$ | O | CH$_3$ | H | Cl |
| Y. 025 | OCF$_3$ | CH$_3$ | O | CH$_3$ | OCH$_3$ | Cl |
| Y. 026 | OCF$_3$ | CH$_3$ | O | Cl | H | Cl |
| Y. 027 | OCF$_3$ | CH$_3$ | O | Cl | H | F |
| Y. 028 | OCF$_3$ | CH$_3$ | O | CH$_3$ | H | H |
| Y. 029 | OCF$_3$ | CH$_3$ | O | Cl | H | H |
| Y. 030 | OCF$_3$ | CH$_3$ | O | CH$_3$ | OCH$_3$ | H |
| Y. 031 | OCF$_3$ | H | S | CH$_3$ | H | CH$_3$ |
| Y. 032 | OCF$_3$ | H | S | iPr | H | H |
| Y. 033 | OCF$_3$ | H | S | CH$_3$ | OCH$_3$ | CH$_3$ |

TABLE Y-continued

| Comp. No | $R_a$ | $R_1$ | Y | $R_b$ | $R_c$ | $R_d$ |
|---|---|---|---|---|---|---|
| Y. 034 | OCF$_3$ | H | S | CH$_3$ | H | Cl |
| Y. 035 | OCF$_3$ | H | S | CH$_3$ | OCH$_3$ | Cl |
| Y. 036 | OCF$_3$ | H | S | Cl | H | Cl |
| Y. 037 | OCF$_3$ | H | S | Cl | H | F |
| Y. 038 | OCF$_3$ | H | S | CH$_3$ | H | H |
| Y. 039 | OCF$_3$ | H | S | Cl | H | H |
| Y. 040 | OCF$_3$ | H | S | CH$_3$ | OCH$_3$ | H |
| Y. 041 | OCF$_2$CF$_3$ | H | S | CH$_3$ | H | CH$_3$ |
| Y. 042 | OCF$_2$CF$_3$ | H | S | iPr | H | H |
| Y. 043 | OCF$_2$CF$_3$ | H | S | CH$_3$ | OCH$_3$ | CH$_3$ |
| Y. 044 | OCF$_2$CF$_3$ | H | S | CH$_3$ | H | Cl |
| Y. 045 | OCF$_2$CF$_3$ | H | S | CH$_3$ | OCH$_3$ | Cl |
| Y. 046 | OCF$_2$CF$_3$ | H | S | Cl | H | Cl |
| Y. 047 | OCF$_2$CF$_3$ | H | S | Cl | H | F |
| Y. 048 | OCF$_2$CF$_3$ | H | S | CH$_3$ | H | H |
| Y. 049 | OCF$_2$CF$_3$ | H | S | Cl | H | H |
| Y. 050 | OCF$_2$CF$_3$ | H | S | CH$_3$ | OCH$_3$ | H |
| Y. 051 | OCF$_3$ | CH$_3$ | S | CH$_3$ | H | CH$_3$ |
| Y. 052 | OCF$_3$ | CH$_3$ | S | iPr | H | H |
| Y. 053 | OCF$_3$ | CH$_3$ | S | CH$_3$ | OCH$_3$ | CH$_3$ |
| Y. 054 | OCF$_3$ | CH$_3$ | S | CH$_3$ | H | Cl |
| Y. 055 | OCF$_3$ | CH$_3$ | S | CH$_3$ | OCH$_3$ | Cl |
| Y. 056 | OCF$_3$ | CH$_3$ | S | Cl | H | Cl |
| Y. 057 | OCF$_3$ | CH$_3$ | S | Cl | H | F |
| Y. 058 | OCF$_3$ | CH$_3$ | S | CH$_3$ | H | H |
| Y. 059 | OCF$_3$ | CH$_3$ | S | Cl | H | H |
| Y. 060 | OCF$_3$ | CH$_3$ | S | CH$_3$ | OCH$_3$ | H | and the N-oxides of the compounds of Table Y.

Table 9: This table discloses the 60 compounds 9.001 to 9.060 of the formula 1-9, wherein $R_a$, $R_1$, Y, $R_b$, $R_c$ and $R_d$ are as defined in Table Y.

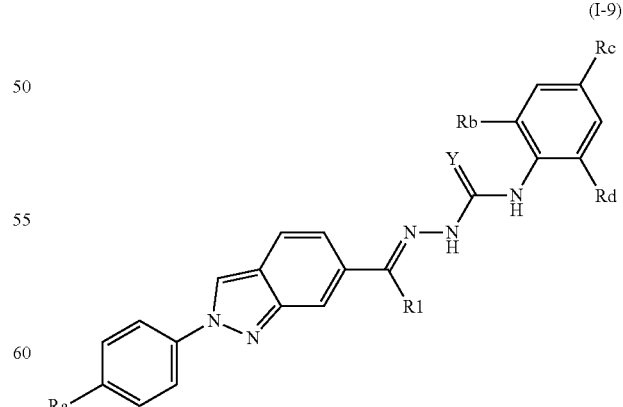

(I-9)

Table 10: This table discloses the 60 compounds 10.001 to 10.060 of the formula 1-10, wherein $R_a$, $R_1$, Y, $R_b$, $R_c$ and $R_d$ are as defined in Table Y.

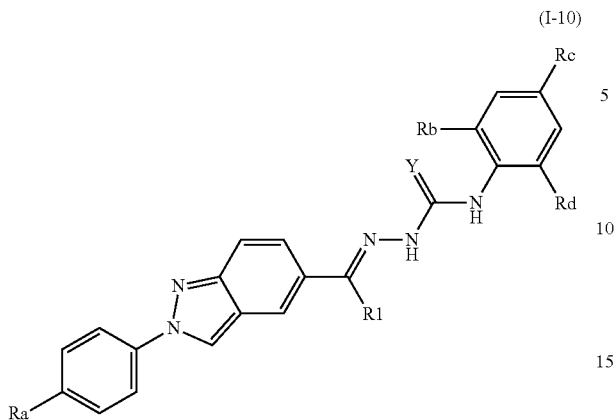

(I-10)

Table 11: This table discloses the 60 compounds 11.001 to 11.060 of the formula 1-11, wherein $R_a$, $R_1$, Y, $R_b$, $R_c$ and $R_d$ are as defined in Table Y.

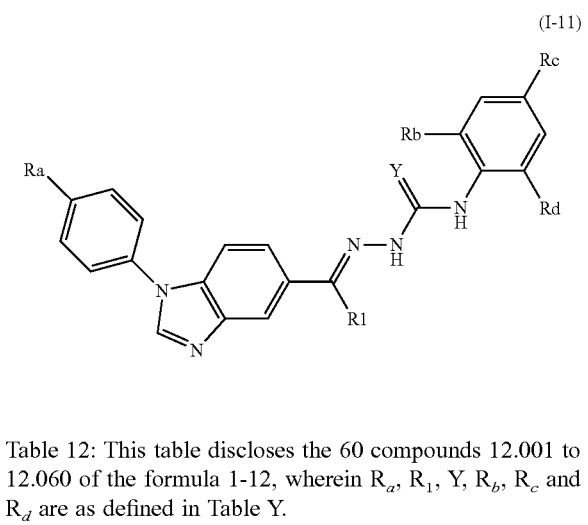

(I-11)

Table 12: This table discloses the 60 compounds 12.001 to 12.060 of the formula 1-12, wherein $R_a$, $R_1$, Y, $R_b$, $R_c$ and $R_d$ are as defined in Table Y.

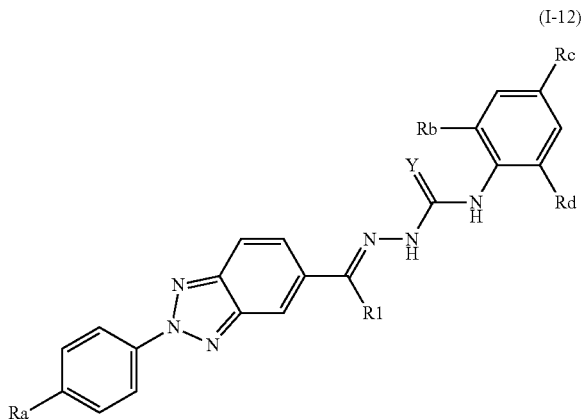

(I-12)

Table 13: This table discloses the 60 compounds 13.001 to 13.060 of the formula 1-13, wherein $R_a$, $R_1$, Y, $R_b$, $R_c$ and $R_d$ are as defined in Table Y.

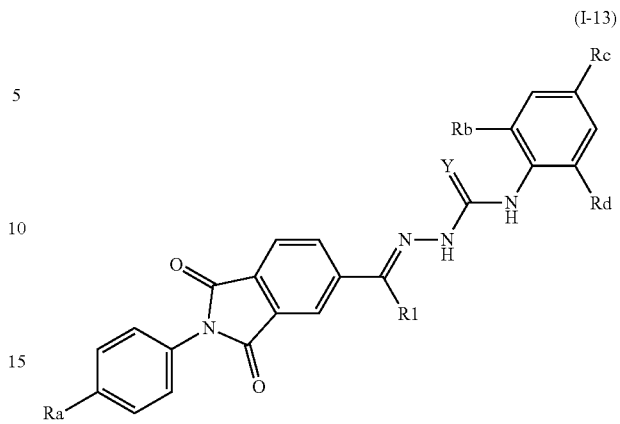

(I-13)

The compounds of formula I according to the invention are preventively and/or curatively valuable active ingredients in the field of pest control, even at low rates of application, which have a favorable biocidel spectrum and are well tolerated by warm-blooded species, fish and plants. Compounds of formula I may act against all or only individual developmental stages of normally sensitive, but also resistant, animal pests, such as insects or representatives of the order Acarina. The insecticidal or acaricidal activity of the compounds can manifest itself directly, i. e. in destruction of the pests, which takes place either immediately or only after some time has elapsed, for example during ecdysis, or indirectly, for example in a reduced oviposition and/or hatching rate, a good activity corresponding to a destruction rate (mortality) of at least 50 to 60%.

Examples of the abovementioned animal pests are:

from the order Acarina, for example, *Acalitus* spp, *Aculus* spp, *Acaricalus* spp, *Aceria* spp, *Acarus siro*, *Amblyomma* spp., *Argas* spp., *Boophilus* spp., *Brevipalpus* spp., *Bryobia* spp, *Calipitrimerus* spp., *Chorioptes* spp., *Dermanyssus gallinae*, *Dermatophagoides* spp, *Eotetranychus* spp, *Eriophyes* spp., *Hemitarsonemus* spp, *Hyalomma* spp., *Ixodes* spp., *Olygonychus* spp, *Ornithodoros* spp., *Polyphagotarsone latus*, *Panonychus* spp., *Phyllocoptruta oleivora*, *Phytonemus* spp, *Polypha-gotarsonemus* spp, *Psoroptes* spp., *Rhipicephalus* spp., *Rhizoglyphus* spp., *Sarcoptes* spp., *Steneotarsonemus* spp, *Tarsonemus* spp. and *Tetranychus* spp.;

from the order Anoplura, for example, *Haematopinus* spp., *Linognathus* spp., *Pediculus* spp., *Pemphigus* spp. and *Phylloxera* spp.;

from the order Coleoptera, for example, *Agriotes* spp., *Amphimallon majale*, *Anomala orientalis*, *Anthonomus* spp., *Aphodius* spp, *Astylus atromaculatus*, *Ataenius* spp, *Atomaria linearis*, *Chaetocnema tibialis*, *Cerotoma* spp, *Conoderus* spp, *Cosmopolites* spp., *Cotinis nitida*, *Curculio* spp., *Cyclocephala* spp, *Dermestes* spp., *Diabrotica* spp., *Diloboderus abderus*, *Epilachna* spp., *Eremnus* spp., *Heteronychus arator*, *Hypothenemus hampei*, *Lagria vilosa*, *Leptinotarsa decemLineata*, *Lissorhoptrus* spp., *Liogenys* spp, *Maecolaspis* spp, *Maladera castanea*, *Megascelis* spp, *Melighetes aeneus*, *Melolontha* spp., *Myochrous armatus*, *Orycaephilus* spp., *Otiorhynchus* spp., *Phyllophaga* spp, *Phlyctinus* spp., *Popillia* spp., *Psylliodes* spp., *Rhyssomatus aubtilis*, *Rhizopertha* spp., *Scarabeidae*, *Sitophilus* spp., *Sitotroga* spp., *Somaticus* spp, *Sphenophorus* spp, *Sternechus subsignatus*, *Tenebrio* spp., *Tribolium* spp. and *Trogoderma* spp.;

from the order Diptera, for example, *Aedes* spp., *Anopheles* spp, *Antherigona soccata, Bactrocea oleae, Bibio hortulanus, Bradysia* spp, *Calliphora erythrocephala, Ceratitis* spp., *Chrysomyia* spp., *Culex* spp., *Cuterebra* spp., *Dacus* spp., *Delia* spp, *Drosophila melanogaster, Fannia* spp., *Gastrophilus* spp., *Geomyza tripunctata, Glossina* spp., *Hypoderma* spp., *Hyppobosca* spp., *Liriomyza* spp., *Lucilia* spp., *Melanagromyza* spp., *Musca* spp., *Oestrus* spp., *Orseolia* spp., *Oscinella frit, Pegomyia hyoscyami, Phorbia* spp., *Rhagoletis* spp, *Rivelia quadrifasciata, Scatella* spp, *Sciara* spp., *Stomoxys* spp., *Tabanus* spp., *Tannia* spp. and *Tipula* spp.;

from the order Hemiptera, for example, *Acanthocoris scabrator, Acrostemum* spp, *Adelphocoris lineolatus, Amblypelta nitida, Bathycoelia thalassina, Blissus* spp, *Cimex* spp., *Clavigralla tomentosicollis, Creontiades* spp, *Distantiella theobroma, Dichelops furcatus, Dysdercus* spp., *Edessa* spp, *Euchistus* spp., *Eurydema pulchrum, Eurygaster* spp., *Halyomorpha halys, Horcias nobilellus, Leptocorisa* spp., *Lygus* spp, *Margarodes* spp, *Murgantia histrionic, Neomegalotomus* spp, *Nesidiocoris tenuis, Nezara* spp., *Nysius simulans, Oebalus insularis, Piesma* spp., *Piezodorus* spp, *Rhodnius* spp., *Sahlbergella singularis, Scaptocoris castanea, Scotinophara* spp., *Thyanta* spp, *Triatoma* spp., and *Vatiga illudens;* from the order homoptera, for example, *Acyrthosium pisum, Adalges* spp, *Agalliana ensigera, Agonoscena targionii, Aleurodicus* spp, *Aleurocanthus* spp, *Aleurolobus barodensis, Aleurothrixus floccosus, Aleyrodes brassicae, Amarasca biguttula, Amritodus atkinsoni, Aonidiella* spp., *Aonidiella auranti, Aphididae, Aphis* spp., *Aspidiotus* spp., *Aulacorthum solani, Bactericera cockerelli, Bemisia* spp, *Brachycaudus* spp, *Brevicoryne brassicae, Cacopsylla* spp, *Cavariella aegopodii* Scop., *Ceroplaster* spp., *Chrysomphalus aonidium, Chrysomphalus dictyospermi, Cicadella* spp, *Cofana spectra, Cryptomyzus* spp, *Cicadulina* spp, *Coccus hesperidum, Dalbulus maidis, Dialeurodes* spp, *Diaphorina citri, Diuraphis noxia, Dysaphis* spp, *Empoasca* spp., *Eriosoma larigerum, Erythroneura* spp., *Gascardia* spp., *Glycaspis brimblecombei, Hyadaphis pseudobrassicae, Hyalopterus* spp, *Hyperomyzus pallidus, ldioscopus clypealis, Jacobiasca lybica, Laodelphax* spp., *Lecanium corn, Lepidosaphes* spp., *Lopaphis erysimi, Lyogenys maidis, Macrosiphum* spp., *Mahanarva* spp, *Metcalfa pruinosa, Metopolophium dirhodum, Myndus crudus, Myzus* spp., *Neotoxoptera* sp, *Nephotettix* spp., *Nilaparvata* spp., *Nippolachnus piri Mats, Odonaspis ruthae, Oregma lanigera Zehnter, Parabemisia myricae, Paratrioza cockerelli, Parlatoria* spp., *Pemphigus* spp., *Peregrinus maidis, Perkinsiella* spp, *Phorodon humuli, Phylloxera* spp, *Planococcus* spp., *Pseudaulacaspis* spp., *Pseudococcus* spp., *Pseudatomoscelis seriatus, Psylla* spp., *Pulvinaria aethiopica, Quadraspidiotus* spp., *Quesada gigas, Recilia dorsalis, Rhopalosiphum* spp., *Saissetia* spp., *Scaphoideus* spp., *Schizaphis* spp., *Sitobion* spp., *Sogatella furcifera, Spissistilus festinus, Tarophagus Proserpina, Toxoptera* spp, *Trialeurodes* spp, *Tridiscus sporoboli, Trionymus* spp, *Trioza erytreae, Unaspis citri, Zygina flammigera,* and *Zyginidia scutellaris;* from the order Hymenoptera, for example, *Acromyrmex, Arge* spp, *Atta* spp., *Cephus* spp., *Diprion* spp., *Diprionidae, Gilpinia polytoma, Hoplocampa* spp., *Lasius* spp., *Monomorium pharaonis, Neodiprion* spp., *Pogonomyrmex* spp., *Slenopsis invicta, Solenopsis* spp. and *Vespa* spp.;

from the order Isoptera, for example, *Coptotermes* spp, *Corniternes cumulans, Incisitermes* spp, *Macrotermes* spp, *Mastotermes* spp, *Microtermes* spp, *Reticulitermes* spp.; *Solenopsis geminate;* from the order Lepidoptera, for example, *Acleris* spp., *Adoxophyes* spp., *Aegeria* spp., *Agrotis* spp., *Alabama argillaceae, Amylois* spp., *Anticarsia gemmatalis, Archips* spp., *Argyresthia* spp, *Argyrotaenia* spp., *Autographa* spp., *Bucculatrix thurberiella, Busseola fusca, Cadra cautella, Carposina nipponensis, Chilo* spp., *Choristoneura* spp., *Chrysoteuchia topiaria, Clysia ambiguella, Cnaphalocrocis* spp., *Cnephasia* spp., *Cochylis* spp., *Coleophora* spp., *Colias lesbia, Cosmophila flava, Crambus* spp, *Crocidolomia binotalis, Cryptophlebia leucotreta, Cydalima perspectalis, Cydia* spp., *Diaphania perspectalis, Diatraea* spp., *Diparopsis castanea, Earias* spp., *Eldana saccharina, Ephestia* spp., *Epinotia* spp, *Estigmene acrea, Etiella zinckinella, Eucosma* spp., *Eupoecilia ambiguella, Euproctis* spp., *Euxoa* spp., *Feltia jaculiferia, Grapholita* spp., *Hedya nubiferana, Heliothis* spp., *Hellula undalis, Herpetogramma* spp, *Hyphantria cunea, Keiferia lycopersicella, Lasmopalpus lignosellus, Leucoptera scitella, Lithocollethis* spp., *Lobesia botrana, Loxostege bifidalis, Lymantria* spp., *Lyonetia* spp., *Malacosoma* spp., *Mamestra brassicae, Manduca sexta, Mythimna* spp, *Noctua* spp, *Operophtera* spp., *Orniodes indica, Ostrinia nubilalis, Pammene* spp., *Pandemis* spp., *Panolis flammea, Papaipema nebris, Pectinophora gossypiela, Perileucoptera coffeella, Pseudaletia unipuncta, Phthorimaea operculella, Pieris rapae, Pieris* spp., *Plutella xylostella, Prays* spp., *Pseudoplusia* spp, *Rachiplusia nu, Richia albicosta, Scirpophaga* spp., *Sesamia* spp., *Sparganothis* spp., *Spodoptera* spp., *Sylepta derogate, Synanthedon* spp., *Thaumetopoea* spp., *Tortrix* spp., *Trichoplusia ni, Tuta absoluta,* and *Yponomeuta* spp.;

from the order Mallophaga, for example, *Damalinea* spp. and *Trichodectes* spp.;

from the order Orthoptera, for example, *Blatta* spp., *Blattella* spp., *Gryllotalpa* spp., *Leucophaea maderae, Locusta* spp., *Neocurtilla hexadactyla, Periplaneta* spp., *Scapteriscus* spp, and *Schistocerca* spp.;

from the order Psocoptera, for example, *Liposcelis* spp.;

from the order Siphonaptera, for example, *Ceratophyllus* spp., *Ctenocephalides* spp. and *Xenopsylla cheopis;* from the order Thysanoptera, for example, *Calliothrips phaseoli, Frankliniella* spp., *Heliothrips* spp, *Hercinothrips* spp., *Parthenothrips* spp, *Scirtothrips aurantii, Sericothrips variabilis, Taeniothrips* spp., *Thrips* spp; and/or from the order Thysanura, for example, *Lepisma saccharina.*

Examples of soil-inhabiting pests, which can damage a crop in the early stages of plant development, are:

from the order Lepidoptera, for example, *Acleris* spp., *Aegeria* spp., *Agrotis* spp., *Alabama argillaceae, Amylois* spp., *Autographa* spp., *Busseola fusca, Cadra cautella, Chilo* spp., *Crocidolomia binotalis, Diatraea* spp., *Diparopsis castanea, Elasmopalpus* spp., *Heliothis* spp., *Mamestra brassicae, Phthorimaea operculella, Plutella xylostella, Scirpophaga* spp., *Sesamia* spp., *Spodoptera* spp. and *Tortrix* spp.;

from the order Coleoptera, for example, *Agriotes* spp., *Anthonomus* spp., *Atomaria linearis, Chaetocnema tibialis, Conotrachelus* spp., *Cosmopolites* spp., *Curculio* spp., *Derrnestes* spp., *Diabrotica* spp., *Dilopoderus* spp., *Epilachna* spp., *Eremnus* spp., *Heteronychus* spp., *Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae, Sitotroga* spp., *Somaticus* spp., *Tanymecus* spp., *Tenebrio* spp., *Tribolium* spp., *Trogoderma* spp. and *Zabrus* spp.;

from the order Orthoptera, for example, *Gryllotalpa* spp.;

from the order Isoptera, for example, *Reticulitermes* spp.;

from the order Psocoptera, for example, *Liposcelis* spp.;

from the order Anoplura, for example, *Haematopinus* spp., *Linognathus* spp., *Pediculus* spp., *Pemphigus* spp. and *Phylloxera* spp.;

from the order Homoptera, for example, *Eriosoma larigerum;* from the order Hymenoptera, for example, *Acromyrmex, Atta* spp., *Cephus* spp., *Lasius* spp., *Monomorium pharaonis, Neodiprion* spp., *Solenopsis* spp. and *Vespa* spp.;

from the order Diptera, for example, *Tipula* spp.;

crucifer flea beetles (*Phyllotreta* spp.), root maggots (*Delia* spp.), cabbage seedpod weevil (*Ceutorhynchus* spp.) and aphids.

The compounds of formula (I) may be useful for the control of nematodes. Thus, in a further aspect, the invention also relates to a method of controlling damage to plant and parts thereof by plant parasitic nematodes (Endoparasitic-, Sem iendoparasitic- and Ectoparasitic nematodes), especially plant parasitic nematodes such as root knot nematodes, *Meloidogyne hapla, Meloidogyne incognita, Meloidogyne javanica, Meloidogyne arenaria* and other *Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Eelonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Ditylenchus* species; Awl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Pin nematodes, *Pratylenchus* species; Lesion nematodes, *Pratylenchus neglectus, Pratylenchus penetrans, Pratylenchus curvitatus, Pratylenchus goodeyi* and other *Pratylenchus* species; Burrowing nematodes, *Radopholus similis* and other *Radopholus* species; Reniform nematodes, *Rotylenchus robustus, Rotylenchus reniformis* and other *Rotylenchus* species; *Scutellonema* species; Stubby root nematodes, *Trichodorus primitivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species, such as *Subanguina.*, spp *Hypsoperine* spp., *Macroposthonia* spp., *Melinius* spp., *Punctodera* spp., and *Quinisulcius* spp.

In particular, the nematode species *Meloidogyne* spp., *Heterodera* spp., *Rotylenchus* spp. and *Pratylenchus* spp. can be controlled by the present inventive compounds.

The active ingredients according to the invention can be used for controlling, i. e. containing or destroying, pests of the abovementioned type which occur in particular on plants, especially on useful plants and ornamentals in agriculture, in horticulture and in forests, or on organs, such as fruits, flowers, foliage, stalks, tubers or roots, of such plants, and in some cases even plant organs which are formed at a later point in time remain protected against these pests.

Suitable target crops are, in particular, cereals, such as wheat, barley, rye, oats, rice, maize or sorghum; beet, such as sugar or fodder beet; fruit, for example pomaceous fruit, stone fruit or soft fruit, such as apples, pears, plums, peaches, almonds, cherries or berries, for example strawberries, raspberries or blackberries; leguminous crops, such as beans, lentils, peas or soya; oil crops, such as oilseed rape, mustard, poppies, olives, sunflowers, coconut, castor, cocoa or ground nuts; cucurbits, such as pumpkins, cucumbers or melons; fibre plants, such as cotton, flax, hemp or jute; citrus fruit, such as oranges, lemons, grapefruit or tangerines; vegetables, such as spinach, lettuce, asparagus, cabbages, carrots, onions, tomatoes, potatoes or bell peppers; Lauraceae, such as avocado, Cinnamonium or camphor; and also tobacco, nuts, coffee, eggplants, sugarcane, tea, pepper, grapevines, hops, the plantain family, latex plants and ornamentals.

The term "crops" is to be understood as including also crop plants which have been so transformed by the use of recombinant DNA techniques that they are capable of synthesising one or more selectively acting toxins, such as are known, for example, from toxin-producing bacteria, especially those of the genus *Bacillus*.

Further areas of use of the compositions according to the invention are the protection of stored goods and store ambients and the protection of raw materials, such as wood, textiles, floor coverings or buildings, and also in the hygiene sector, especially the protection of humans, domestic animals and productive livestock against pests of the mentioned type.

The present invention also provides a method for controlling pests (such as mosquitoes and other disease vectors). In one embodiment, the method for controlling pests comprises applying the compositions of the invention to the pests or their environment, to their locus, for example the soil or to a surface or substrate by brushing, rolling, spraying, spreading or dipping. By way of example, an IRS (indoor residual spraying) application of a surface such as a wall, ceiling or floor surface is contemplated by the method of the invention. In another embodiment, it is contemplated to apply such compositions to a substrate such as non-woven or a fabric material in the form of (or which can be used in the manufacture of) netting, clothing, bedding, curtains and tents.

In one embodiment, the method for controlling such pests comprises applying a pesticidally effective amount of the compositions of the invention to the target pests, to their locus, or to a surface or substrate so as to provide effective residual pesticidal activity on the surface or substrate. Such application may be made by brushing, rolling, spraying, spreading or dipping the pesticidal composition of the invention. By way of example, an IRS application of a surface such as a wall, ceiling or floor surface is contemplated by the method of the invention so as to provide effective residual pesticidal activity on the surface. In another embodiment, it is contemplated to apply such compositions for residual control of pests on a substrate such as a fabric material in the form of (or which can be used in the manufacture of) netting, clothing, bedding, curtains and tents.

Substrates including non-woven, fabrics or netting to be treated may be made of natural fibres such as cotton, raffia, jute, flax, sisal, hessian, or wool, or synthetic fibres such as polyamide, polyester, polypropylene, polyacrylonitrile or the like. The polyesters are particularly suitable. The methods of textile treatment are known, e.g. WO 2008/151984, WO 2003/034823, U.S. Pat. No. 5,631,072, WO 2005/64072, WO2006/128870, EP 1724392, WO2005113886 or WO 2007/090739.

The invention therefore also relates to pesticidal compositions such as emulsifiable concentrates, suspension concentrates, microemulsions, oil dispersibles, directly sprayable or dilutable solutions, spreadable pastes, dilute emulsions, soluble powders, dispersible powders, wettable powders, dusts, granules or encapsulations in polymeric substances, which comprise—at least—one of the active ingredients according to the invention and which are to be selected to suit the intended aims and the prevailing circumstances.

The inventions therefore relates to a pesticidal composition, which comprises at least one compound of formula (I), or where appropriate, a tautomer thereof, in each case in free form or in agrochemically utilizable salt form, as active ingredient and at least one auxiliary In these compositions, the active ingredient is employed in pure form, a solid active ingredient for example in a specific particle size, or, preferably, together with—at least—one of the auxiliaries conventionally used in the art of formulation, such as extenders, for example solvents or solid carriers, or such as surface-active compounds (surfactants).

Examples of suitable solvents are: unhydrogenated or partially hydrogenated aromatic hydrocarbons, preferably the fractions $C_8$ to $C_{12}$ of alkylbenzenes, such as xylene mixtures, alkylated naphthalenes or tetrahydronaphthalene, aliphatic or cycloaliphatic hydrocarbons, such as paraffins or cyclohexane, alcohols such as ethanol, propanol or butanol, glycols and their ethers and esters such as propylene glycol, dipropylene glycol ether, ethylene glycol or ethylene glycol monomethyl ether or ethylene glycol monoethyl ether, ketones, such as cyclohexanone, isophorone or diacetone alcohol, strongly polar solvents, such as N-methylpyrrolid-2-one, dimethyl sulfoxide or N,N-dimethylformamide, water, unepoxidized or epoxidized vegetable oils, such as unexpodized or epoxidized rapeseed, castor, coconut or soya oil, and silicone oils.

Solid carriers which are used for example for dusts and dispersible powders are, as a rule, ground natural minerals such as calcite, talc, kaolin, montmorillonite or attapulgite. To improve the physical properties, it is also possible to add highly disperse silicas or highly disperse absorbtive polymers. Suitable adsorptive carriers for granules are porous types, such as pumice, brick grit, sepiolite or bentonite, and suitable non-sorptive carrier materials are calcite or sand. In addition, a large number of granulated materials of inorganic or organic nature can be used, in particular dolomite or comminuted plant residues.

Suitable surface-active compounds are, depending on the type of the active ingredient to be formulated, non-ionic, cationic and/or anionic surfactants or surfactant mixtures which have good emulsifying, dispersing and wetting properties. The surfactants mentioned below are only to be considered as examples; a large number of further surfactants which are conventionally used in the art of formulation and suitable according to the invention are described in the relevant literature.

Suitable non-ionic surfactants are, especially, polyglycol ether derivatives of aliphatic or cycloaliphatic alcohols, of saturated or unsaturated fatty acids or of alkyl phenols which may contain approximately 3 to approximately 30 glycol ether groups and approximately 8 to approximately 20 carbon atoms in the (cyclo)aliphatic hydrocarbon radical or approximately 6 to approximately 18 carbon atoms in the alkyl moiety of the alkyl phenols. Also suitable are water-soluble polyethylene oxide adducts with polypropylene glycol, ethylenediaminopolypropylene glycol or alkyl polypropylene glycol having 1 to approximately 10 carbon atoms in the alkyl chain and approximately 20 to approximately 250 ethylene glycol ether groups and approximately 10 to approximately 100 propylene glycol ether groups. Normally, the abovementioned compounds contain 1 to approximately 5 ethylene glycol units per propylene glycol unit. Examples which may be mentioned are nonylphenoxypolyethoxyethanol, castor oil polyglycol ether, polypropylene glycol/polyethylene oxide adducts, tributylphenoxypolyethoxyethanol, polyethylene glycol or octylphenoxypolyethoxyethanol. Also suitable are fatty acid esters of polyoxyethylene sorbitan, such as polyoxyethylene sorbitan trioleate.

The cationic surfactants are, especially, quarternary ammonium salts which generally have at least one alkyl radical of approximately 8 to approximately 22 C atoms as substituents and as further substituents (unhalogenated or halogenated) lower alkyl or hydroxyalkyl or benzyl radicals. The salts are preferably in the form of halides, methylsulfates or ethylsulfates. Examples are stearyltrimethylammonium chloride and benzylbis(2-chloroethyl)ethylammonium bromide.

Examples of suitable anionic surfactants are water-soluble soaps or water-soluble synthetic surface-active compounds. Examples of suitable soaps are the alkali, alkaline earth or (unsubstituted or substituted) ammonium salts of fatty acids having approximately 10 to approximately 22 C atoms, such as the sodium or potassium salts of oleic or stearic acid, or of natural fatty acid mixtures which are obtainable for example from coconut or tall oil; mention must also be made of the fatty acid methyl taurates. However, synthetic surfactants are used more frequently, in particular fatty sulfonates, fatty sulfates, sulfonated benzimidazole derivatives or alkylaryl sulfonates. As a rule, the fatty sulfonates and fatty sulfates are present as alkali, alkaline earth or (substituted or unsubstituted) ammonium salts and they generally have an alkyl radical of approximately 8 to approximately 22 C atoms, alkyl also to be understood as including the alkyl moiety of acyl radicals; examples which may be mentioned are the sodium or calcium salts of lignosulfonic acid, of the dodecylsulfuric ester or of a fatty alcohol sulfate mixture prepared from natural fatty acids. This group also includes the salts of the sulfuric esters and sulfonic acids of fatty alcohol/ethylene oxide adducts. The sulfonated benzimidazole derivatives preferably contain 2 sulfonyl groups and a fatty acid radical of approximately 8 to approximately 22 C atoms. Examples of alkylarylsulfonates are the sodium, calcium or triethanolammonium salts of decylbenzenesulfonic acid, of dibutylnaphthalenesulfonic acid or of a naphthalenesulfonic acid/formaldehyde condensate. Also possible are, furthermore, suitable phosphates, such as salts of the phosphoric ester of a p-nonylphenol/(4-14)ethylene oxide adduct, or phospholipids.

As a rule, the compositions comprise 0.1 to 99%, especially 0.1 to 95%, of active ingredient and 1 to 99.9%, especially 5 to 99.9%, of at least one solid or liquid adjuvant, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient.

Typically, a pre-mix formulation for foliar application comprises 0.1 to 99.9%, especially 1 to 95%, of the desired ingredients, and 99.9 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Normally, a tank-mix formulation for seed treatment application comprises 0.25 to 80%, especially 1 to 75%, of the desired ingredients, and 99.75 to 20%, especially 99 to 25%, of a solid or liquid auxiliaries (including, for example, a solvent such as water), where the auxiliaries can be a surfactant in an amount of 0 to 40%, especially 0.5 to 30%, based on the tank-mix formulation.

Typically, a pre-mix formulation for seed treatment application comprises 0.5 to 99.9%, especially 1 to 95%, of the desired ingredients, and 99.5 to 0.1%, especially 99 to 5%, of a solid or liquid adjuvant (including, for example, a solvent such as water), where the auxiliaries can be a surfactant in an amount of 0 to 50%, especially 0.5 to 40%, based on the pre-mix formulation.

Whereas commercial products will preferably be formulated as concentrates (e.g., pre-mix composition (formulation)), the end user will normally employ dilute formulations (e.g., tank mix composition).

Preferred seed treatment pre-mix formulations are aqueous suspension concentrates. The formulation can be applied to the seeds using conventional treating techniques and machines, such as fluidized bed techniques, the roller mill method, rotostatic seed treaters, and drum coaters. Other methods, such as spouted beds may also be useful. The seeds may be presized before coating. After coating, the seeds are typically dried and then transferred to a sizing machine for sizing. Such procedures are known in the art.

In general, the pre-mix compositions of the invention contain 0.5 to 99.9 especially 1 to 95, advantageously 1 to 50%, by mass of the desired ingredients, and 99.5 to 0.1, especially 99 to 5%, by mass of a solid or liquid adjuvant (including, for example, a solvent such as water), where the auxiliaries (or adjuvant) can be a surfactant in an amount of 0 to 50, especially 0.5 to 40%, by mass based on the mass of the pre-mix formulation.

Examples of foliar formulation types for pre-mix compositions are:
GR: Granules
WP: wettable powders
WG: water dispersable granules (powders)
SG: water soluble granules
SL: soluble concentrates
EC: emulsifiable concentrate
EW: emulsions, oil in water
ME: micro-emulsion
SC: aqueous suspension concentrate
CS: aqueous capsule suspension
OD: oil-based suspension concentrate, and
SE: aqueous suspo-emulsion.

Whereas, examples of seed treatment formulation types for pre-mix compositions are:
WS: wettable powders for seed treatment slurry
LS: solution for seed treatment
ES: emulsions for seed treatment
FS: suspension concentrate for seed treatment
WG: water dispersible granules, and
CS: aqueous capsule suspension.

Examples of formulation types suitable for tank-mix compositions are solutions, dilute emulsions, suspensions, or a mixture thereof, and dusts.

Preferred compositions are composed in particular as follows (%=percent by weight):
Emulsifiable Concentrates:
active ingredient: 1 to 95%, preferably 5 to 20%
surfactant: 1 to 30%, preferably 10 to 20
solvent: 5 to 98%, preferably 70 to 85%

Dusts:
active ingredient: 0.1 to 10%, preferably 0.1 to 1%
solid carrier: 99.9 to 90%, preferably 99.9 to 99%
Suspension concentrates:
active ingredient: 5 to 75%, preferably 10 to 50%
water: 94 to 24%, preferably 88 to 30%
surfactant: 1 to 40%, preferably 2 to 30%
Wettable powders:
active ingredient: 0.5 to 90%, preferably 1 to 80%
surfactant: 0.5 to 20%, preferably 1 to 15%
solid carrier: 5 to 99%, preferably 15 to 98%
Granulates:
active ingredient: 0.5 to 30%, preferably 3 to 15%
solid carrier: 99.5 to 70%, preferably 97 to 85%

PREPARATORY EXAMPLES

"Mp" means melting point in ° C. $^1$H NMR measurements were recorded on a Brucker 400 MHz spectrometer, chemical shifts are given in ppm relevant to a TMS standard. Spectra measured in deuterated solvents as indicated.

LC MS Method: Standard:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 0% B, 100% A; 1.2-1.5 min 100% B; Flow (ml/min) 0.85.

Example P1: Preparation of N-(2,6-dimethylphenyl)-2-((2-(4-(trifluoromethoxy)phenyl)-2H-indazol-6-yl)methylene)hydrazinecarbothioamide (Compound P1)

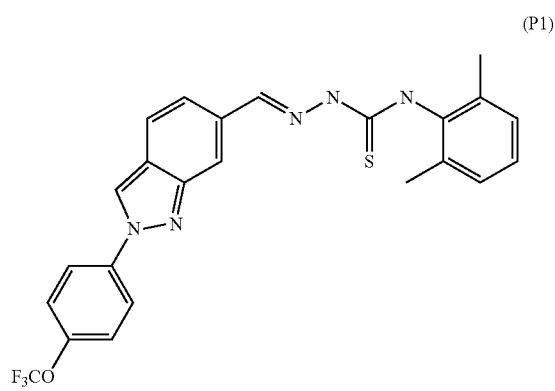 [SMILES: Cc1cccc(C)c1NC(=S)N/N=C/c1ccc2cn(-c3ccc(OC(F)(F)F)cc3)nc2c1]

(P1)

Step A-1: Preparation of 6-methyl-2-[4-(trifluoromethoxy)phenyl]indazole

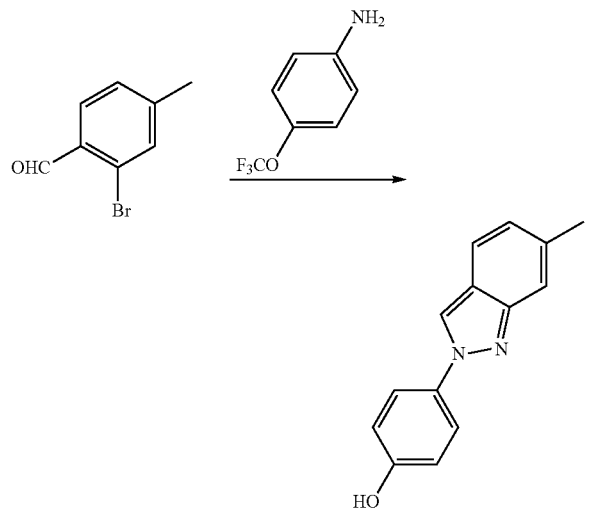

A solution of 2-bromo-4-methyl-benzaldehyde (30.0 g, 0.15 mol) and 4-(trifluoromethoxy)aniline (32.0 g, 0.180 mol) in dimethylformamide (300 mL) was charged with sodium azide (18.9 g, 0.30 mol) followed by tetramethylethylenediamine (1.74 g, 0.015 mol) at room temperature followed stirring for 10 minutes. Copper iodide (2.85 g, 0.015 mol) was added to the reaction mixture and heated to 120° C. for 16 hours. The reaction mixture was cooled to 0° C., diluted with water (300 mL) and extracted into ethyl acetate (2×500 mL). The combined organic layers were washed with brine (100 mL), dried over anhydrous sodium sulfate and concentrated under the reduced pressure. The residue was purified by column chromatography to afford 6-methyl-2-[4-(trifluoromethoxy)phenyl]indazole (5.00 g) as light brown solid.

MS m/z: 293 [M+H]$^+$.

$^1$H NMR (400 MHz, CDCl$_3$): δ 8.31 (s, 1H), 7.92 (dd, 2H), 7.59 (d, 1H), 7.51 (s, 1H), 7.37 (d, 2H), 6.96 (dd, 1H), 2.46 (s, 3H).

Step A-2: Preparation of 2-[4-(trifluoromethoxy)phenyl]indazole-6-carbaldehyde

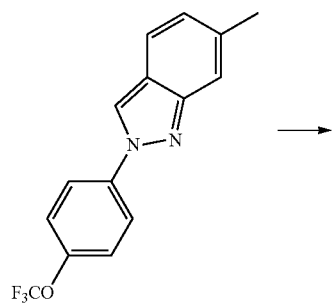

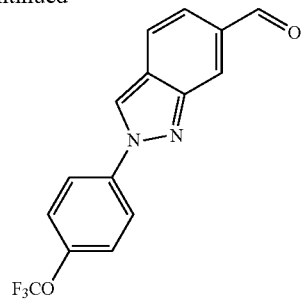

A solution of 6-methyl-2-[4-(trifluoromethoxy)phenyl]indazole (5.0 g, 0.017 mol) in 1, 4-dioxane (100 mL) was charged with selenium oxide (5.65 g, 0.514 mol) at room temperature and heated to 110° C. for 72 hours. The reaction mixture was cooled to 0° C., diluted with water (100 mL) and extracted with ethyl acetate (2×300 mL). The combined organics was washed with brine (50 mL), dried over anhydrous sodium sulfate and concentrated under the reduced pressure. The residue was purified by column chromatography to afford 2-[4-(trifluoromethoxy)phenyl]indazole-6-carbaldehyde (3.00 g) as pale yellow solid.

MS m/z: 307 [M+H]$^+$.

$^1$H NMR (300 MHz, CDCl$_3$): δ 10.10 (s, 1H), 8.46 (d, 1H), 8.30 (d, 1H), 7.95-7.99 (m, 2H), 7.80 (d, 1H), 7.66 (dd, 1H), 7.42 (d, 2H).

Step A-3: Preparation of 2-isothiocyanato-1,3-dimethyl-benzene

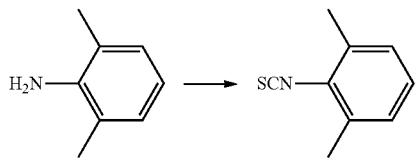

A solution of 2,6-dimethylaniline (5.00 g, 0.04 mol) in acetonitrile (100 mL) was charged with 1,1'-thiocarbonyldiimidazole (14.7 g, 0.08 mol) drop wise at 0° C. over 10 min and stirred at room temperature for 16 hours. The reaction mixture was cooled to 0° C., quenched with water (200 mL) and extracted with ethyl acetate (2×100 mL). The combined organic layers were washed with water (100 mL) and brine (50 mL), dried over anhydrous sodium sulfate, and concentrated under reduced pressure. The residue was purified by flash column chromatography to afford 2-isothiocyanato-1,3-dimethyl-benzene (4.50 g) as a colorless liquid.

$^1$H NMR (300 MHz, CDCl$_3$): δ 7.09-7.01 (m, 3H), 2.37 (s, 6H).

Step A-4: Preparation of 1-amino-3-(2,6-dimethylphenyl)thiourea

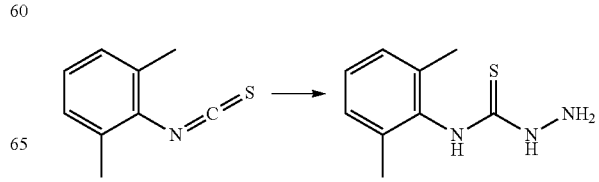

A solution of 2-isothiocyanato-1,3-dimethyl-benzene (2.00 g, 0.01 mol) in ethanol (40 mL) was charged with hydrazine hydrate (5.80 mL, 0.12 mol) drop wise at 0° C. over 10 min and stirred at room temperature for 16 hours. The reaction mixture was concentrated under reduced pressure and treated with MTBE (50 mL) and was dried under vacuum to afford to afford 1-amino-3-(2,6-dimethylphenyl) thiourea (2.20 g) as an off white solid.

MS m/z: 196 [M+H]$^+$.

$^1$H NMR (300 MHz, CDCl$_3$): δ 9.09 (bs, 1H), 8.90 (bs, 1H), 7.05-7.04 (m, 3H), 4.69 (bs, 2H), 2.14 (s, 6H).

Step A-5: Preparation of 1-(2,6-dimethylphenyl)-3-[[2-[4-(trifluoromethoxy)phenyl]indazol-6-yl]methyleneamino]thiourea

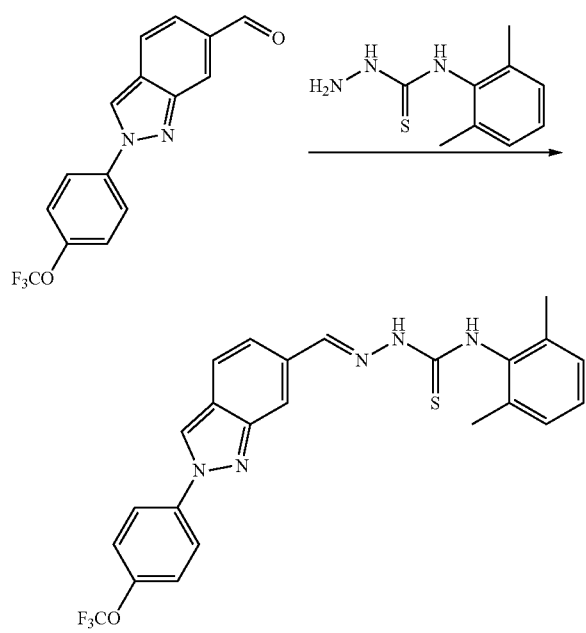

A solution of 2-[4-(trifluoromethoxy)phenyl]indazole-6-carbaldehyde (1.00 g, 3.26 mmol, and 1-amino-3-(2,6-dimethylphenyl)thiourea (0.64 g, 3.26 mmol) in ethanol (25 mL) was charged with acetic acid (40 mg, 0.65 mmol) at room temperature and heated to 90° C. for 16 hours. The reaction mixture was cooled to room temperature and the solids were filtered, washed with ethanol (10 mL) and dried under vacuum to afford 1-(2,6-dimethylphenyl)-3-[(E)-[2-[4-(trifluoromethoxy)phenyl]indazol-6-yl]methyleneamino]thiourea (0.71 g) as pale yellow solid.

MS m/z: 484 [M+H]$^+$.

Example P2: Preparation of N-(2-isopropylphenyl)-2-((2-(4-(trifluoromethoxy)phenoxy)quinolin-6-yl)methylene)hydrazinecarbothioamide (Compound P2)

(P2)

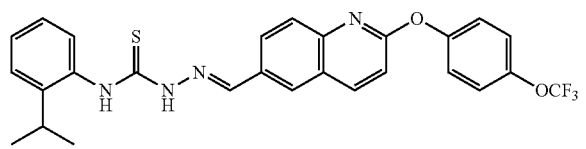

Step B-1: Preparation of 6-bromo-2-[4-(trifluoromethoxy)phenoxy]quinoline

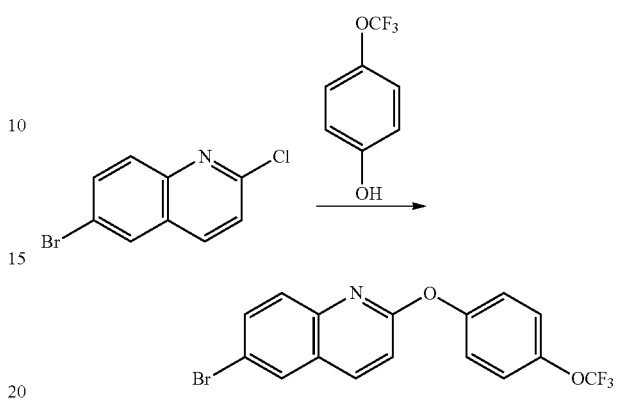

A suspension of sodium hydride (0.25 g, 6.16 mmol) in dimethylformamide (5 mL) was charged with a solution of 4-(trifluoromethoxy)phenol (1.00 g, 5.60 mmol) in dimethylformamide (5 mL) at 0° C. and stirred at same temperature for 30 minutes. A solution of 6-bromo-2-chloro-quinoline (1.36 g, 5.60 mmol) in dimethylformamide (5 mL) was added to the reaction mixture drop wise over 15 minutes at 0° C. The reaction mixture was heated to 90° C. for 16 hours. The reaction mixture was cooled to 0° C., diluted with water (20 mL) and extracted into ethyl acetate (2×50 mL). The combined organics was washed with brine (20 mL), dried over anhydrous sodium sulfate, concentrated under the reduced pressure. The residue was triturated with ethanol (20 mL) and filtered, dried under vacuum to afford 6-bromo-2-[4-(trifluoromethoxy)phenoxy]quinoline (1.10 g) as brown solid.

MS m/z: 384 [M+H]$^+$ $^1$H NMR (400 MHz, CDCl$_3$): δ 8.05 (d, 1H), 7.92 (d, 1H), 7.62-7.70 (m, 2H), 7.27 (d, 1H), 7.13 (d, 1H).

Step B-2: Preparation of 2-[4-(trifluoromethoxy)phenoxy]quinoline-6-carbaldehyde

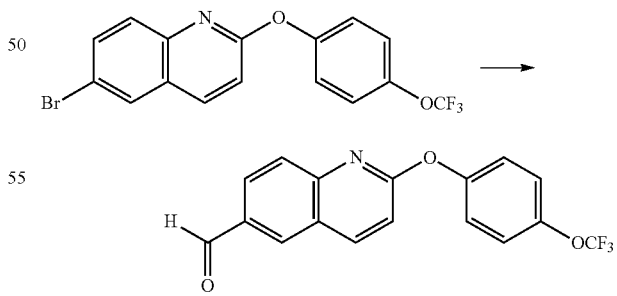

A solution of 6-bromo-2-[4-(trifluoromethoxy)phenoxy]quinoline (0.80 g, 2.08 mmol) in tetrahydrofuran (20 mL) was charged with n-buthyllithium (1.0 mL, 2.5 M in hexanes) drop wise over 5 minutes at −78° C. and stirred at the same temperature for 1 hour. Dimethylformamide (25 mg, 4.16 mmol) in tetrahydrofuran (1.0 mL) was added drop wise over 2 minutes at −78° C. The reaction mixture was stirred at same temperature for another 2 hours. The reaction mixture was diluted with 2 N HCl (10 mL) and extracted with ethyl acetate (2×50 mL). The combined organics was washed with brine (20 mL), dried over anhydrous sodium sulfate and concentrated under the reduced pressure. The residue was purified by column chromatography to afford 2-[4-(trifluoromethoxy)phenoxy]quinoline-6-carbaldehyde (0.20 g) as an off white solid.

MS m/z: 334 [M+H]$^+$ $^1$H NMR (400 MHz, DMSO-d$_6$): δ 10.1 (s, 1H), 8.67 (d, 1H), 8.62 (d, 1H), 8.07 (dd, 1H), 7.77 (d, 1H), 7.44-7.51 (m, 5H).

Step B-3: Preparation of 1-amino-3-(2-isopropylphenyl)thiourea

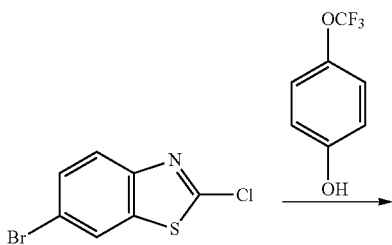

A solution of 1-isopropyl-2-isothiocyanato-benzene (1.00 g, 5.64 mmol) in ethanol (10 mL) was charged with hydrazine monohydrochloride (1 mL) at room temperature and stirred 16 hours. The resulted solids were filtered, washed with ethanol (5 mL) and dried under vacuum to afford 1-amino-3-(2-isopropylphenyl)thiourea (0.60 g) as an off white solid.

$^1$H NMR (400 MHz, DMSO-d$_6$): δ 9.01 (bs, 1H), 7.35 (s, 1H), 7.29 (dd, 1H), 7.12-7.27 (m, H), 4.30-5.30 (bs, 2H), 3.08 (m, 1H), 1.16 (d, 6H).

Step B-4: Preparation of 1-(2-isopropylphenyl)-3-[[2-[4-(trifluoromethoxy)phenoxy]-6-quinolyl]-methyleneamino]thiourea

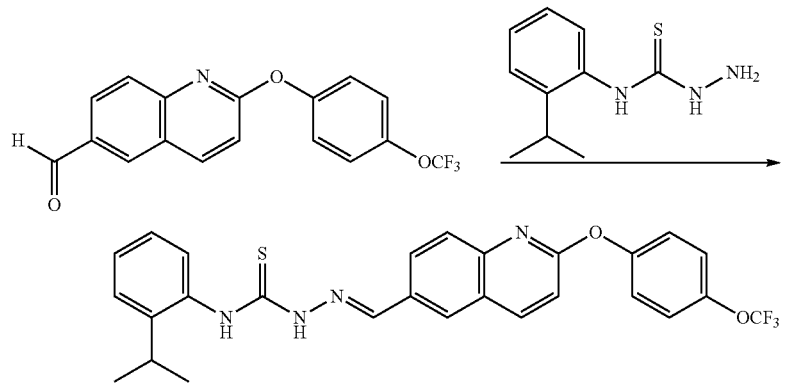

A solution of 2-[4-(trifluoromethoxy)phenoxy]quinoline-6-carbaldehyde (0.20 g, 0.60 mmol) and 1-amino-3-(2-isopropylphenyl)thiourea (0.126 g, 0.60 mmol) in ethanol (10 mL) was charged with acetic acid (7.0 mg, 0.12 mmol) at room temperature and heated at 90° C. for 16 hours. The reaction mixture was cooled to room temperature and the solids were filtered, washed with ethanol (5 mL) and dried under vacuum to afford 1-(2-isopropylphenyl)-3-[(E)-[2-[4-(trifluoromethoxy)phenoxy]-6-quinolyl]methyleneamino]thiourea (0.20 g) as pale yellow solid.

MS m/z: 525 [M+H]$^+$.

$^1$H NMR (400 MHz, DMSO-d$_6$): δ 11.8 (s, 1H), 10.10 (s, 1H), 8.44-8.51 (m, 2H), 8.29 (s, 1H), 8.21 (d, 1H), 7.62 (d, 1H), 7.40-7.50 (m, 4H), 7.17-7.37 (m, 5H).

Example P3: Preparation of 1-(2-isopropylphenyl)-3-[[2-[4-(trifluoromethoxy)phenoxy]-1,3-benzothiazol-6-yl]methyleneamino]thiourea (Compound P3)

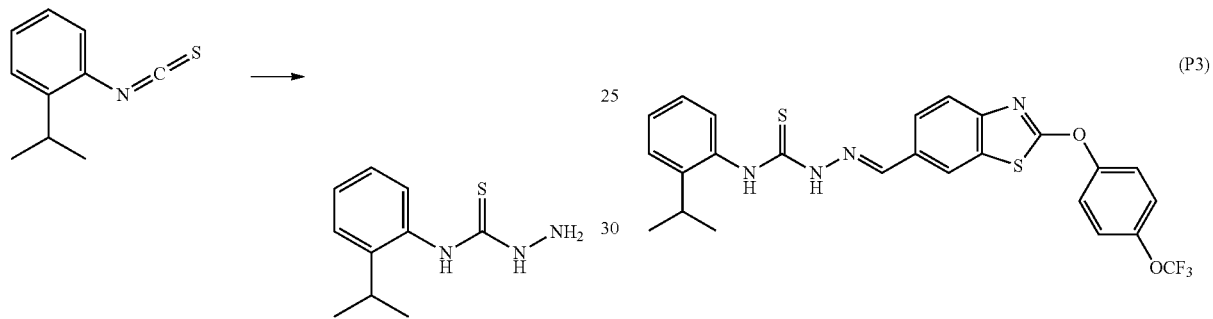

Step C-1: Preparation of 6-bromo-2-[4-(trifluoromethoxy)phenoxy]-1,3-benzothiazole

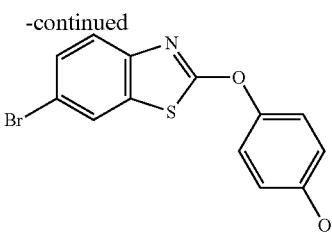

A suspension of sodium hydride (0.25 g, 6.16 mmol) in dimethylformamide (5 mL) was charged with a solution of 4-(trifluoromethoxy)phenol (1.0 g, 5.60 mmol) in dimethylformamide (5 mL) at 0° C. and stirred for 30 minutes. 6-bromo-2-chloro-1,3-benzothiazole (1.40 g, 5.60 mmol) in dimethylformamide (5 mL) was added to the reaction mixture drop wise over 15 minutes at 0° C. The reaction mixture was heated to 90° C. for 16 hours. The reaction mixture was cooled to 0° C., diluted with water (20 mL) and extracted with ethyl acetate (2×50 mL). The combined organics was washed with brine (20 mL), dried over anhydrous sodium sulfate, concentrated under the reduced pressure. The residue was triturated with ethanol (20 mL) and filtered, dried under vacuum to afford 6-bromo-2-[4-(trifluoromethoxy) phenoxy]-1,3-benzothiazole (1.00 g) as off white solid.

MS m/z: 392.0 [M+H]+.

$^1$H NMR (300 MHz, DMSO-d$_6$): δ 8.26 (d, 1H), 7.53-7.67 (m, 6H).

Step C-2: Preparation of 2-[4-(trifluoromethoxy) phenoxy]-1,3-benzothiazole-6-carbaldehyde

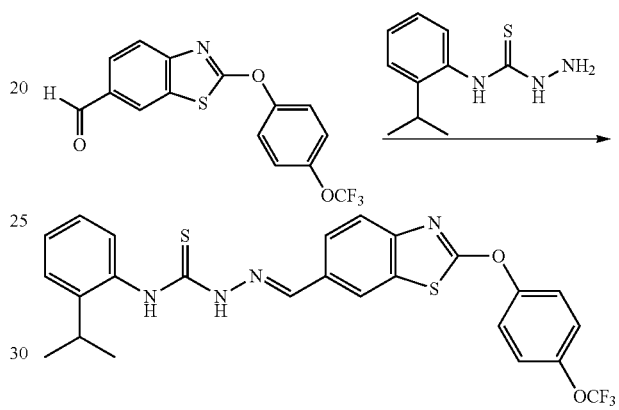

A solution of 6-bromo-2-[4-(trifluoromethoxy)phenoxy]-1,3-benzothiazole (1.00 g, 2.56 mmol) in tetrahydrofuran (20 mL) was charged with n-buthyllithium (1.1 mL, 2.50 M in hexanes) drop wise over 5 minutes at −78° C. and stirred at same temperature for 1 hour. Dimethylformamide (370 mg, 5.12 mmol) in tetrahydrofuran (1.0 mL) was added drop wise over 2 minutes at −78° C. The reaction mixture was stirred at same temperature for another 2 hours. The reaction mixture was diluted with HCl (2 N, 10 mL) and extracted with ethyl acetate (2×50 mL). The combined organics was washed with brine (20 mL), dried over anhydrous sodium sulfate and concentrated under the reduced pressure. The residue was purified by column chromatography to afford 2-[4-(trifluoromethoxy)phenoxy]-1,3-benzothiazole-6-carbaldehyde (0.10 g) as an off white solid.

MS m/z: 340 [M+H]+.

$^1$H NMR (300 MHz, DMSO-d$_6$): δ 10.03 (s, 1H), 8.59 (d, 1H), 7.96 (dd, 1H), 7.88 (d, 1H), 7.59-7.69 (m, 2H), 7.57 (d, 2H).

Step C-3: Preparation of 1-(2-isopropylphenyl)-3-[[2-[4-(trifluoromethoxy)phenoxy]-1,3-benzothiazol-6-yl]methyleneamino]thiourea

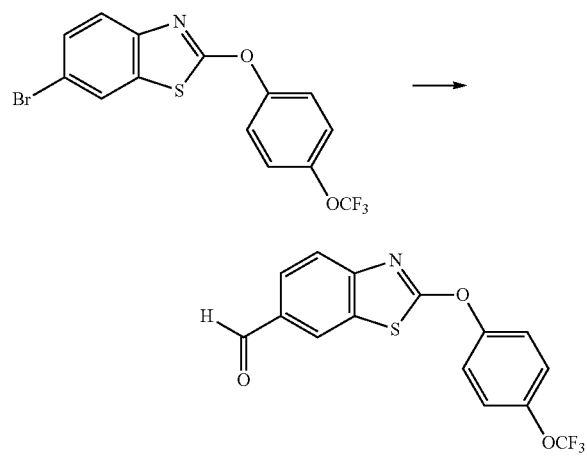

A solution of 2-[4-(trifluoromethoxy)phenoxy]-1,3-benzothiazole-6-carbaldehyde (0.10 g, 0.295 mmol) and 1-amino-3-(2-isopropylphenyl)thiourea (62 mg, 0.295 mmol, described in step B-3) in ethanol (5 mL) was charged with acetic acid (3.50 mg, 0.06 mmol) at room temperature and heated to 90° C. for 16 hours. The reaction mixture was cooled to room temperature and the solids were filtered, washed with ethanol (2 mL) and dried under vacuum to afford 1-(2-isopropylphenyl)-3-[(E)-[2-[4-(trifluoromethoxy)phenoxy]-1,3-benzothiazol-6-yl]methyleneamino]thiourea (40 mg) as pale yellow solid.

MS m/z: 531 [M+H]+.

$^1$H NMR (300 MHz, DMSO-d$_6$): δ 11.81 (s, 1H), 10.00 (s, 1H), 8.48 (s, 1H), 8.19 (s, 1H), 8.04 (dd, 1H), 7.72 (d, 1H), 7.66-7.62 (m, 2H), 7.54 (d, 2H), 7.17-7.37 (m, 4H).

Example P4: Preparation of 1-(2,6-dimethylphenyl)-3-[(E)-[1,3-dioxo-2-[4-(trifluoromethoxy)phenyl]isoindolin-5-yl]methyleneamino]thiourea (Compound P4)

(P4)

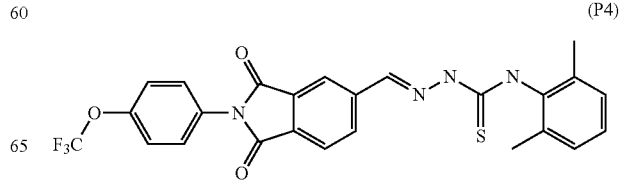

Step D-1: Preparation of 1,3-dioxo-2-[4-(trifluoromethoxy)phenyl]isoindoline-5-carboxylic acid

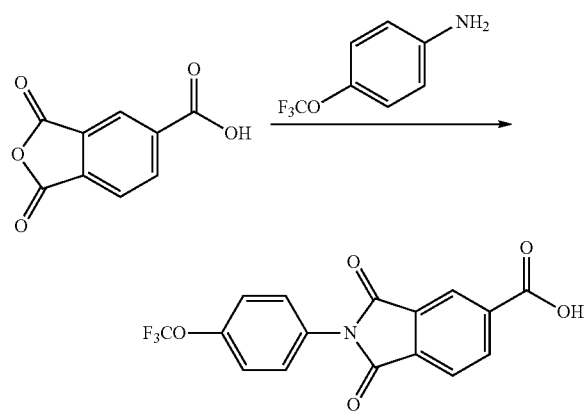

Under Argon a mixture of 1,3-dioxoisobenzofuran-5-carboxylic acid (200 mg, 1.04 mmol) and 4-(trifluoromethoxy)aniline (0.184 mg, 1.04 mmol)) in acetic acid (5 ml) was heated to reflux for 2 hours. The reaction was quenched with ice water and the precipitate was filtered off and washed with water and tert-butylmethylether to give 1,3-dioxo-2-[4-(trifluoromethoxy)phenyl]isoindoline-5-carboxylic acid (206 mg) as beige crystals.

LC-MS: $t_R$=1.51 min, m/z=350 [M−1].

$^1$H NMR (400 MHz, DMSO) δ ppm 7.55-7.65 (m, 4H) 8.11 (d, J=7.70 Hz, 1H) 8.32-8.33 (m, 1H) 8.43 (dd, J=7.70, 1.47 Hz, 1H) 13.76 (br. s., 1H).

Step D-2: Preparation of 5-(hydroxymethyl)-2-[4-(trifluoromethoxy)phenyl]isoindoline-1,3-dione

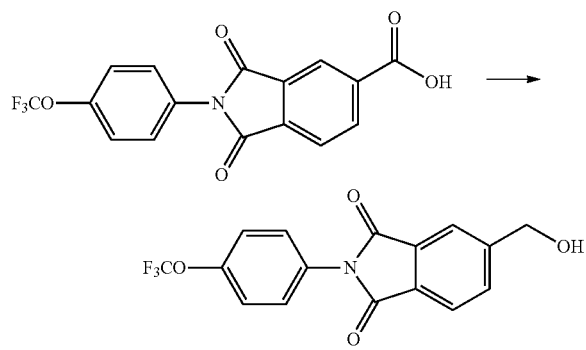

Under Argon a mixture of 1,3-dioxo-2-[4-(trifluoromethoxy)phenyl]isoindoline-5-carboxylic acid (190 mg, 0.541 mmol) in tetrahydrofuran (3 ml) was cooled to 0° C., then a solution of borane in tetrahydrofuran (0.65 ml, 1 M) was added. The mixture was stirred at ambient temperature overnight. After completion, the reaction mixture was diluted with a solution of hydrochloridric acid, extracted with ethyl acetate and washed with brine. The combined organic layers were dried over magnesium sulfate and evaporated under vacuo to give 5-(hydroxymethyl)-2-[4-(trifluoromethoxy)phenyl]isoindoline-1,3-dione (163 mg) as a beige solid.

LC-MS: $t_R$=1.43 min, m/z=338 [M+1].

$^1$H NMR (400 MHz, CDCl$_3$) δ ppm 4.79-4.97 (m, 2H) 7.34-7.38 (m, 2H) 7.50-7.53 (m, 2H) 7.78-7.82 (m, 1H) 7.92-7.99 (m, 2H).

Step D-3: Preparation of 1,3-dioxo-2-[4-(trifluoromethoxy)phenyl]isoindoline-5-carbaldehyde

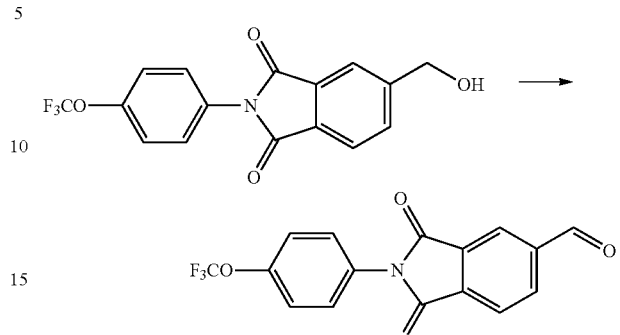

To a solution of 5-(hydroxymethyl)-2-[4-(trifluoromethoxy)phenyl]isoindoline-1,3-dione (0.3 g, 0.89 mmol) in dichloromethane (10 ml) was added manganese dioxide (0.85 g, 9.80 mmol) and the reaction mixture was stirred at ambient temperature overnight. It was then filtered through a pad of celite, and washed with dichloromethane, the combined filtrate and washing were concentrated under reduced pressure. The crude product was purified by flash chromatography to give 1,3-dioxo-2-[4-(trifluoromethoxy)phenyl]iso-indoline-5-carbaldehyde (246 mg) as beige crystals.

$^1$H NMR (400 MHz, CDCl$_3$) δ ppm 7.38 (dd, J=9.17, 0.73 Hz, 2H) 7.51-7.56 (m, 2H) 8.15 (d, J=7.70 Hz, 1H) 8.33-8.37 (m, 1H) 8.46 (d, J=0.73 Hz, 1H) 10.21 (s, 1H).

Step D-4: Preparation of 1-(2,6-dimethylphenyl)-3-[(E)-[1,3-dioxo-2-[4-(trifluoromethoxy)phenyl]isoindolin-5-yl]methyleneamino]thiourea

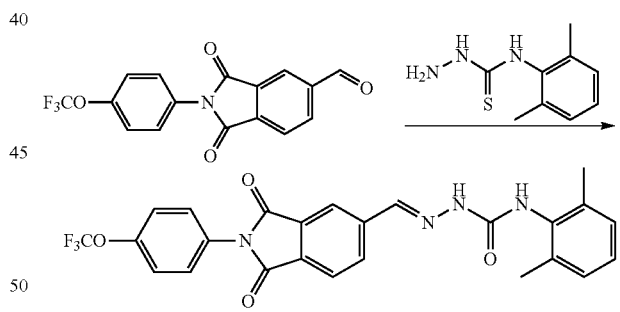

To a suspension of 1,3-dioxo-2-[4-(trifluoromethoxy)phenyl]isoindoline-5-carbaldehyde (85 mg, 0.253 mmol) in methanol (10 ml) was added at room temperature 1-amino-3-(2,6-dimethylphenyl)thiourea (849 mg, 0.253 mmol). This mixture was heated at reflux for 3 h. After complete conversion, the solution was concentrated under vacuum, and the crude product was purified by flash chromatography to give 1-(2,6-dimethylphenyl)-3-[(E)-[1,3-dioxo-2-[4-(trifluoromethoxy)phenyl]isoindolin-5-yl]methyleneamino]thiourea (77 mg) as a yellow solid.

LC-MS: $t_R$=2.02 min, m/z=511 [M−1], 513 [M+1].

$^1$H NMR (400 MHz, CDCl$_3$) δ ppm 2.34 (s, 6H) 7.18 (s, 1H) 7.18-7.18 (m, 1H) 7.37 (d, J=8.07 Hz, 2H) 7.51-7.54 (m, 2H) 8.01-8.04 (m, 3H) 8.31 (s, 1H) 8.69 (s, 1H) 10.01 (s, 1H).

Example P5: Preparation of 1-(2,6-dimethylphenyl)-3-[[1,3-dioxo-2-[4-(trifluoromethoxy)phenyl]isoindolin-5-yl]methyleneamino]urea (Compound P5)

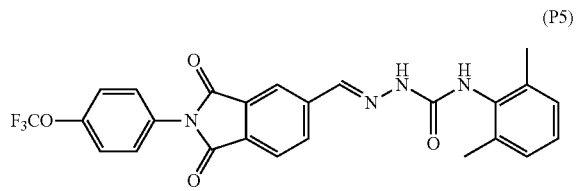 [SMILES: Cc1cccc(C)c1NC(=O)N/N=C/c1ccc2c(c1)C(=O)N(c1ccc(OC(F)(F)F)cc1)C2=O]
(P5)

Step E-1: Preparation of 1-(2,6-dimethylphenyl)-3-[(E)-[1,3-dioxo-2-[4-(trifluoromethoxy)phenyl]isoindolin-5-yl]methyleneamino]urea

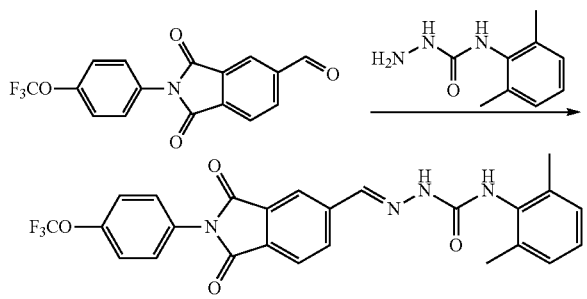

To a suspension of 1,3-dioxo-2-[4-(trifluoromethoxy)phenyl]isoindoline-5-carbaldehyde (200 mg, 0.596 mmol, example P4, step D-3) in methanol (10 ml) was added at room temperature 1-amino-3-(2,6-dimethylphenyl)urea (106 mg, 0.596 mmol). This mixture was heated at reflux for 3 h. After complete conversion, the solution was concentrated under vacuum, and the crude product was purified by crystallisation to give 1-(2,6-dimethylphenyl)-3-[(E)-[1,3-dioxo-2-[4-(trifluoromethoxy)phenyl]isoindolin-5-yl]methyleneamino]urea (244 mg) as a white solid.

LC-MS: $t_R$=1.92 min, m/z=495 [M−1], 497 [M+1].

$^1$H NMR (400 MHz, DMSO-d6) δ ppm 2.22 (s, 6H) 7.54-7.66 (m, 4H) 7.97 (d, J=7.70 Hz, 1H) 8.09 (s, 1H) 8.21 (dd, J=8.07, 1.10 Hz, 1H) 8.65 (s, 1H) 8.89 (s, 1H) 10.91 (s, 1H).

Example P7: Preparation of 1-(2,6-dimethylphenyl)-3-[(E)-[2-[4-(trifluoromethoxy)phenyl]-1,3-benzoxazol-5-yl]methyleneamino]thiourea (Compound P7)

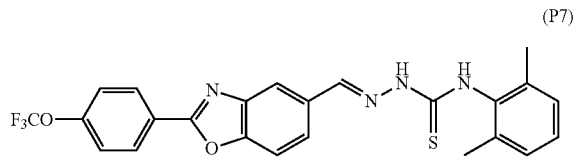 [SMILES: Cc1cccc(C)c1NC(=S)N/N=C/c1ccc2oc(-c3ccc(OC(F)(F)F)cc3)nc2c1]
(P7)

Step F-1: Preparation of 2-[4-(trifluoromethoxy)phenyl]-1,3-benzoxazole-5-carbonitrile

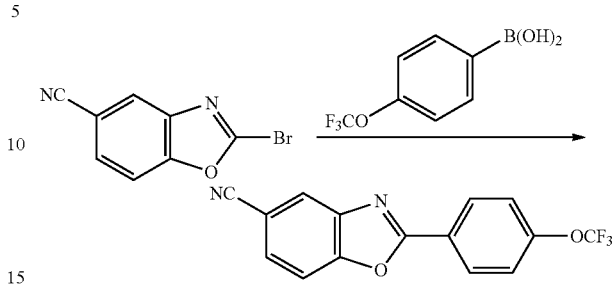

A three necked round bottom flask was charged with 2-bromo-1,3-benzoxazole-5-carbonitrile (0.700 g, 2.82 mmol), tripotassium phosphate (1.85 g, 8.47 mmol) and [4-(trifluoromethoxy)phenyl]boronic acid (0.712 g, 3.39 mmol), 1,4-dioxane (28.2 mL) and water (11.3 mL). The reaction mixture was purged with argon for 30 min. Subsequently, PdCl$_2$(dppf) (0.109 g, 0.141 mmol) was added and the reaction mixture was purged with argon again. The orange reaction mixture was stirred at 90° C. for 1 hour, then cooled to 0-10° C. and diluted with water (20 mL), filtered over celite and washed with ethyl acetate. The mother liquor was diluted in ethyl acetate (300 mL). The organic layer was extracted with water (2×150 mL), brine (150 mL), dried with magnesium sulfate anhydrous, filtered of and evaporated. The crude product was purified by flash-chromatography to give 2-[4-(trifluoromethoxy)phenyl]-1,3-benzoxazole-5-carbonitrile (453 mg) as a white solid.

LC-MS: $t_R$=1.12 min, m/z=305 [M+1].

$^1$H NMR (400 MHz, DMSO-d6) δ ppm 7.67 (d, J=8.44 Hz, 2H) 7.95 (dd, J=8.44, 1.47 Hz, 1H) 8.07 (d, J=8.44 Hz, 1H) 8.37 (d, J=8.80 Hz, 2H) 8.47 (s, 1H).

Step F-2: Preparation of 2-[4-(trifluoromethoxy)phenyl]-1,3-benzoxazole-5-carbaldehyde

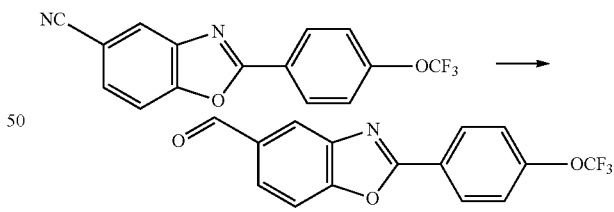

A solution of 2-[4-(trifluoromethoxy)phenyl]-1,3-benzoxazole-5-carbonitrile (0.100 g, 0.322 mmol) in dichloromethane (3.22 mL) was cooled to 0° C. under Argon. A solution of DIBAL-H in dichloromethane (1N, 0.436 g, 0.354 mmol, 0.354 mL) was added and the reaction mixture was stirred at 0° C. for 30 min. The reaction mixture was quenched by the dropwise addition of water at 0° C. It was then diluted in dichloromethane and the organic layer was washed with brine, dried with magnesium sulfate anhydrous, filtered of and evaporated to give 90 mg 2-[4-(trifluoromethoxy)phenyl]-1,3-benzoxazole-5-carbaldehyde.

LC-MS: $t_R$=1.16 min, m/z=308 [M+1].

Step F-3: Preparation of 1-(2,6-dimethylphenyl)-3-[(E)-[2-[4-(trifluoromethoxy)phenyl]-1,3-benzoxazol-5-yl]methyleneamino]thiourea

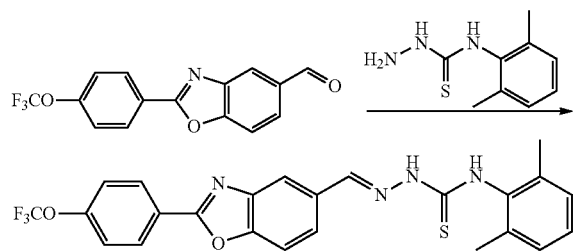

A 5 ml vial was charged with 2-[4-(trifluoromethoxy)phenyl]-1,3-benzoxazole-5-carbaldehyde (0.090 g, 0.26 mmol) and methanol (1.3 mL). 1-Amino-3-(2,6-dimethylphenyl)thiourea (0.051 g, 0.26 mmol) was added and the reaction mixture was stirred at room temperature overnight. The reaction mixture was filtered of, washed with methanol and twice with pentane. The crude product was purified by flash-chromatography to give 1-(2,6-dimethylphenyl)-3-[(E)-[2-[4-(trifluoromethoxy)phenyl]-1,3-benzoxazol-5-yl]methyleneamino]thiourea (30 mg) as a white solid.

LC-MS: $t_R$=1.25 min, m/z=483 [M−1], 485 [M+1].

$^1$H NMR (400 MHz, DMSO-d6) δ ppm 2.22 (s, 6H) 7.12-7.17 (m, 3H) 7.65 (d, J=8.80 Hz, 2H) 7.85 (d, J=8.44 Hz, 1H) 8.02 (d, J=8.80 Hz, 1H) 7.99-8.04 (m, 1H) 7.99-8.04 (m, 1H) 8.27 (s, 1H) 8.23-8.29 (m, 1H) 8.33 (d, J=8.80 Hz, 2H) 8.52 (s, 1H) 10.01 (s, 1H) 11.82 (s, 1H).

Example P10: Preparation of 1-(2,6-dimethylphenyl)-3-[(E)-[2-[4-(trifluoromethoxy)phenyl]-1,3-benzoxazol-5-yl]methyleneamino]urea (Compound P10)

(P10)

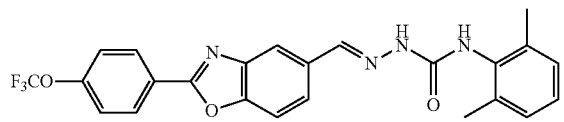

Step G-1: Preparation of 1-(2,6-dimethylphenyl)-3-[(E)-[2-[4-(trifluoromethoxy)phenyl]-1,3-benzoxazol-5-yl]methyleneamino]urea

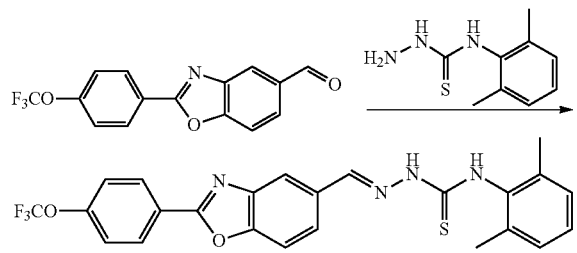

A vial was charged with 2-[4-(trifluoromethoxy)phenyl]-1,3-benzoxazole-5-carbaldehyde (0.070 g, 0.21 mmol, example P7, step F-2) and methanol (2.1 mL). 1-Amino-3-(2,6-dimethylphenyl)urea (0.035 g, 0.19 mmol) was added and the reaction mixture was stirred at room temperature overnight. The reaction mixture was filtered of, washed with methanol and twice with pentane to give 1-(2,6-dimethylphenyl)-3-[(E)-[2-[4-(trifluoromethoxy)phenyl]-1,3-benzoxazol-5-yl]methyleneamino]urea (830 mg) as a white solid.

LC-MS: $t_R$=1.23 min, m/z=467 [M−1], 469 [M+1].

$^1$H NMR (400 MHz, DMSO-d6) δ ppm 2.24 (s, 6H) 7.11 (s, 3H) 7.65 (d, J=8.07 Hz, 2H) 7.83 (d, J=8.80 Hz, 1H) 7.98 (d, J=8.80 Hz, 1H) 8.06 (s, 1H) 8.34 (d, J=8.44 Hz, 2H) 8.40 (s, 1H) 8.67 (s, 1H) 10.65 (s, 1H).

Example P13: Preparation of 1-(2,6-dimethylphenyl)-3-[(E)-[2-[4-(trifluoromethoxy)phenyl]-1,3-benzothiazol-5-yl]methyleneamino]thiourea (Compound P13)

(P13)

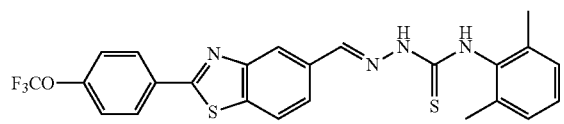

Step H-1: Preparation of 2-[4-(trifluoromethoxy)phenyl]-1,3-benzothiazole-5-carbaldehyde

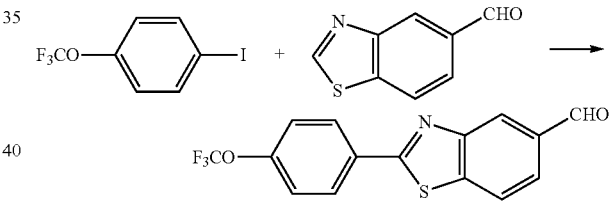

a) A dried vial was charged with copper(I) iodide (0.120 g, 0.630 mmol) and dichloromethane (7.93 g, 92.5 mmol, 5.99 mL). XANTPHOS (0.401 g, 0.693 mmol) was added and the reaction mixture was stirred at room temperature for 15 min. The solvent was removed by bubbling through with argon. The remaining solid was directly used for the next step.

b) A vial was set under argon and charged with Cu(Xantphos)I (0.0471 g, 0.0613 mmol) (procedure step a), dichloro-bis(tricyclohexylphosphine)palladium(II) (0.119 g, 0.153 mmol), cesium carbonate (2.50 g, 7.66 mmol) and toluene (6.13 mL). To the resulting mixture was added 1,3-benzothiazole-5-carbaldehyde (0.500 g, 3.06 mmol) and 1-bromo-4-(trifluoromethoxy)benzene (1.11 g, 4.60 mmol, 0.683 mL). The reaction mixture was stirred at 100° C. overnight. After cooling to room temperature, it was diluted with ethyl acetate and quenched with a solution of ammonium chloride saturated/water (1/1). The resulting suspension was filtered over celite and washed several times with ethyl acetate. The organic layer was separated and washed with water, brine, dried over anhydrous magnesium sulfate, filtered of and evaporated. The crude product was purified over flash-chromatography to give 2-[4-(trifluoromethoxy)phenyl]-1,3-benzothiazole-5-carbaldehyde (352 mg) as a white solid.
LC-MS: $t_R$=1.82 min, m/z=323 [M+1].
$^1$H NMR (400 MHz, DMSO-d6) δ ppm 7.62 (d, J=8.07 Hz, 2H) 8.00 (dd, J=8.25, 1.28 Hz, 1H) 8.30 (d, J=8.80 Hz, 2H) 8.42 (d, J=8.44 Hz, 1H) 8.63 (d, J=1.10 Hz, 1H) 10.18 (s, 1H).

Step H-2: Preparation of 1-(2,6-dimethylphenyl)-3-[(E)-[2-[4-(trifluoromethoxy)phenyl]-1,3-benzothiazol-5-yl]methyleneamino]thiourea

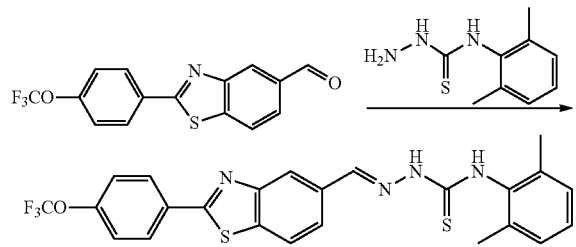

A vial was charged with 2-[4-(trifluoromethoxy)phenyl]-1,3-benzothiazole-5-carbaldehyde (0.060 g, 0.18 mmol) and methanol (1.8 mL). 1-Amino-3-(2,6-dimethylphenyl)thiourea (0.034 g, 0.17 mmol) was added and the reaction mixture was stirred at room temperature overnight. To improve the solubility of the reaction mixture acetonitrile/water (1:1, 1 ml) was added and reaction was further heated at 65° C. After cooling, the reaction mixture was filtered, the cake was washed with methanol and diethyl ether to give 1-(2,6-dimethylphenyl)-3-[(E)-[2-[4-(trifluoromethoxy)phenyl]-1,3-benzothiazol-5-yl]methyleneamino]thiourea (59 mg) as a yellow solid.
LC-MS: $t_R$=1.26 min, m/z=499 [M−1], 501 [M+1].
$^1$H NMR (400 MHz, DMSO-d6) δ ppm 2.22 (s, 6H) 7.13 (br. s., 3H) 7.59 (d, J=8.07 Hz, 2H) 8.04 (d, J=8.07 Hz, 1H) 8.14-8.33 (m, 4H) 8.70 (s, 1H) 10.06 (br. s., 1H) 11.85 (br. s., 1H).

Example P16: Preparation of 1-(2,6-dimethylphenyl)-3-[(E)-[2-[4-(trifluoromethoxy)phenyl]-1,3-benzothiazol-5-yl]methyleneamino]thiourea (Compound P16)

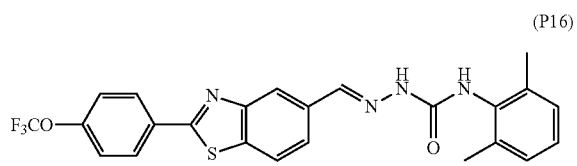 [SMILES: Cc1cccc(C)c1NC(=S)N/N=C/c1ccc2sc(-c3ccc(OC(F)(F)F)cc3)nc2c1]

Step 1-1: Preparation of 1-(2,6-dimethylphenyl)-3-[(E)-[2-[4-(trifluoromethoxy)phenyl]-1,3-benzothiazol-5-yl]methyleneamino]thiourea

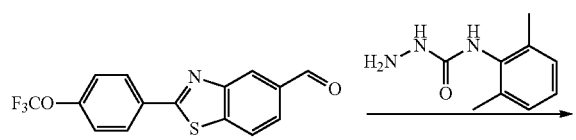

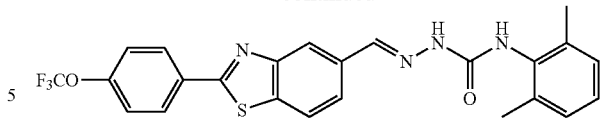

A vial was charged with 2-[4-(trifluoromethoxy)phenyl]-1,3-benzothiazole-5-carbaldehyde (0.060 g, 0.18 mmol, example P13, step H-1) and methanol (1.8 mL). 1-Amino-3-(2,6-dimethylphenyl)urea (0.031 g, 0.17 mmol) was added and the reaction mixture was stirred at room temperature overnight. In order to complete the conversion, the reaction mixture was further heated at 65° C. for 3 hours. The reaction mixture was filtered, the cake was washed with methanol to give 1-(2,6-dimethylphenyl)-3-[(E)-[2-[4-(trifluoromethoxy)phenyl]-1,3-benzothiazol-5-yl]methyleneamino]thiourea (69 mg) as a yellow solid.
LC-MS: $t_R$=1.21 min, m/z=483 [M−1], 485 [M+1].
$^1$H NMR (400 MHz, DMSO-d6) δ ppm 2.23 (s, 6H) 7.10 (s, 3H) 7.59 (d, J=8.07 Hz, 2H) 8.00-8.08 (m, 2H) 8.17-8.25 (m, 3H) 8.57 (s, 1H) 8.71 (s, 1H) 10.68 (s, 1H).

Example P17: Preparation of 1-(2,6-dimethylphenyl)-3-[(E)-[2-[4-(trifluoromethoxy)phenyl]imidazo[1,2-a]pyridin-6-yl]methyleneamino]thiourea (Compound P17)

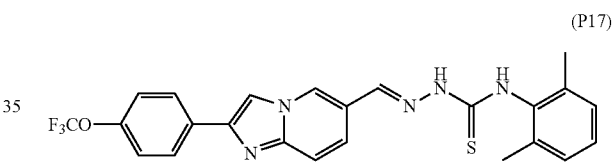

Step J-1: Preparation of 2-[4-(trifluoromethoxy)phenyl]imidazo[1,2-a]pyridine-6-carbonitrile

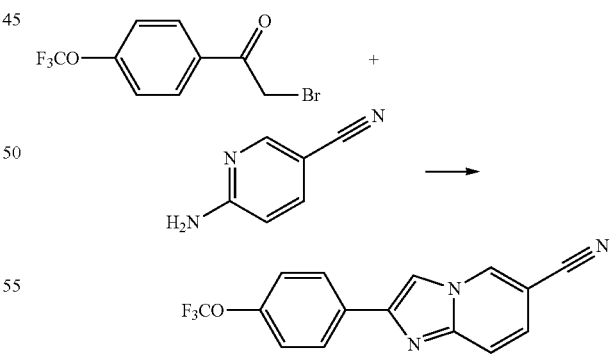

To a solution of 6-aminopyridine-3-carbonitrile (5.1 g, 42.0 mmol) in 190 ml of ethanol was added 2-bromo-1-[4-(trifluoromethoxy)phenyl]ethanone (12.1 g, 42.0 mmol) and the mixture was heated at reflux for 24 hours. After concentration to about 100 ml the precipitated salt was filtered, suspended in water and neutralized with an aqueous NaHCO$_3$ solution. The precipitated free base was filtered, and dried in vacuo. The crude solid was purified by flash-chromatography to give 2-[4-(trifluoromethoxy)phenyl]-imidazo[1,2-a]pyridine-6-carbonitrile (7.43 g) as a white solid.

LC-MS: $t_R$=1.05 min, m/z=304 [M+1].

$^1$H NMR (400 MHz, CDCl$_3$) δ ppm 7.29-7.34 (m, 3H) 7.71 (d, J=9.17 Hz, 1H) 7.95 (s, 1H) 7.97-8.01 (m, 2H) 8.59 (dd, J=1.65, 0.92 Hz, 1H).

Step J-2: Preparation of 2-[4-(trifluoromethoxy)phenyl]-1,3-benzothiazole-5-carbaldehyde

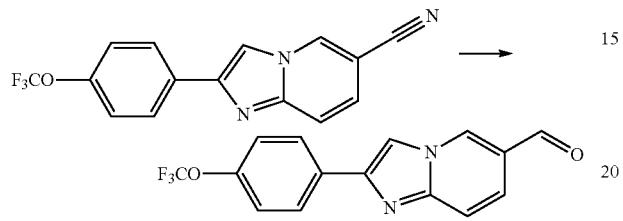

Under Argon, 2-[4-(trifluoromethoxy)phenyl]imidazo[1,2-a]pyridine-6-carbonitrile (1.0 g, 3.1 mmol) was solved in 10 ml tetrahydrofuran and 10 ml dichloromethane, and cooled to −20° C. using dry ice/EtOH. To this solution, a solution of DIBAL-H in toluene (1M, 4.7 ml, 4.7 mmol) was added dropwise at −20° C. and further stirred for 30 min. The mixture was allowed to warm to room temperature and was carefully quenched with 10 ml methanol/ethyl acetate 2:1 at 0° C. The reaction mixture was stirred for 30 min at 0° C. and 10 ml of water was added dropwise at 0° C. The organic phase was separated, and the water was extracted with 2×100 ml dichloromethane. The organic layer was washed with water, brine, dried over sodium sulfate, filtrated and evaporated. Crude product was purified by chromatography to give (2-[4-(trifluoromethoxy)phenyl]-1,3-benzothiazole-5-carbaldehyde (354 mg) as orange crystals.

LC-MS: $t_R$=1.00 min, m/z=307 [M+1].

$^1$H NMR (400 MHz, CDCl$_3$) δ ppm 7.31 (dd, J=8.80, 1.10 Hz, 2H) 7.68-7.74 (m, 2H) 7.97-8.03 (m, 3H) 8.69 (t, J=1.28 Hz, 1H) 9.97 (s, 1H).

Step J-3: Preparation of 1-(2,6-dimethylphenyl)-3-[(E)-[2-[4-(trifluoromethoxy)phenyl]imidazo[1,2-a]pyridin-6-yl]methyleneamino]thiourea

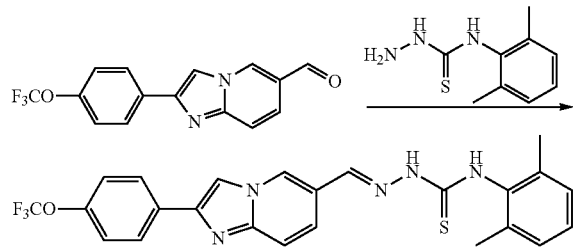

To a suspension of 2-[4-(trifluoromethoxy)phenyl]imidazo[1,2-a]pyridine-6-carbaldehyde (200 mg, 0.653 mmol) in 5 ml methanol was added at room temperature 1-amino-3-(2,6-dimethylphenyl)thiourea. The mixture was heated to reflux and stirred for 3 h. The reaction was almost complete and concentrated under vacuo.

The crude product was purified by flash chromatography to give 1-(2,6-dimethylphenyl)-3-[(E)-[2-[4-(trifluoromethoxy)phenyl]imidazo[1,2-a]pyridin-6-yl]methyleneamino]thiourea (84 mg) as a yellow solid.

LC-MS: $t_R$=1.82 min, m/z=483 [M−1], 484 [M+1].

$^1$H NMR (400 MHz, DMSO-d6) δ ppm 2.21 (s, 6H) 7.11-7.15 (m, 3H) 7.46 (d, J=8.07 Hz, 2H) 7.60 (d, J=9.54 Hz, 1H) 8.07-8.11 (m, 2H) 8.16 (s, 1H) 8.21 (dd, J=9.54, 1.83 Hz, 1H) 8.42 (s, 1H) 8.90 (s, 1H) 9.95 (s, 1H) 11.85 (s, 1H).

Example P18: Preparation of 1-(2,6-dimethylphenyl)-3-[(E)-[2-[4-(trifluoromethoxy)phenyl]imidazo[1,2-a]pyridin-6-yl]methyleneamino]urea (Compound P18)

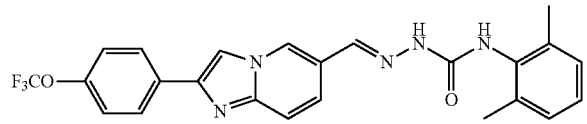

(P18)

Step K-1: Preparation of 1-(2,6-dimethylphenyl)-3-[(E)-[2-[4-(trifluoromethoxy)phenyl]imidazo[1,2-a]pyridin-6-yl]methyleneamino]urea

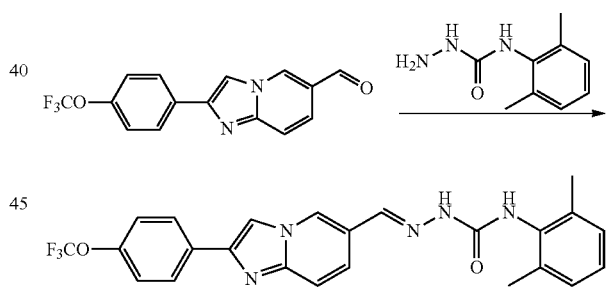

To a suspension of 2-[4-(trifluoromethoxy)phenyl]imidazo[1,2-a]pyridine-6-carbaldehyde (200 mg, 0.653 mmol, example P17, step J-2) in 5 ml methanol was added at room temperature 1-amino-3-(2,6-dimethylphenyl)urea (0.117 mg, 0.653 mmol). The mixture was heated at reflux for 3 hours. The mixture was concentrated under vacuo and purified by flash chromatography to give 1-(2,6-dimethylphenyl)-3-[(E)-[2-[4-(trifluoromethoxy)phenyl]imidazo[1,2-a]pyridin-6-yl]methyleneamino]urea (84 mg) as a yellow solid.

LC-MS: $t_R$=1.82 min, m/z=483 [M−1], 484 [M+1].

$^1$H NMR (400 MHz, DMSO-d6) δ ppm 2.23 (s, 6H) 7.11 (s, 3H) 7.45 (d, J=8.07 Hz, 2H) 7.60 (d, J=9.17 Hz, 1H) 7.96 (s, 1H) 8.08-8.16 (m, 3H) 8.42 (s, 1H) 8.62 (s, 1H) 8.82 (s, 1H) 10.69 (s, 1H).

Example P21: Preparation of 1-(2,6-dimethylphenyl)-3-[(E)-[1-[4-(trifluoromethoxy)phenyl]indazol-5-yl]methyleneamino]thiourea (Compound P21)

(P21)

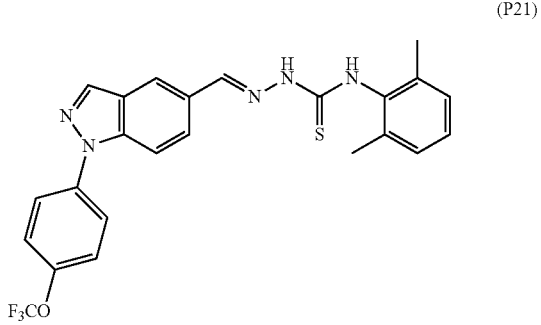 [SMILES: Cc1cccc(C)c1NC(=S)N/N=C/c1ccc2c(cnn2-c2ccc(OC(F)(F)F)cc2)c1]

Step L-1: Preparation of methyl 1-[4-(trifluoromethoxy)phenyl]indazole-5-carboxylate and methyl 2-[4-(trifluoromethoxy)phenyl]indazole-5-carboxylate

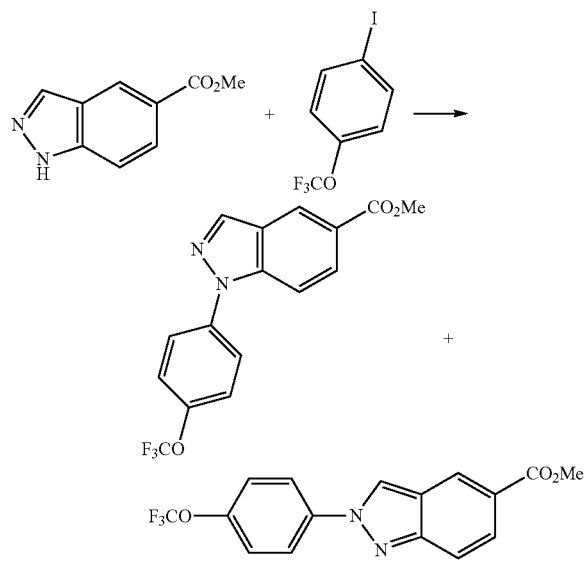

A dried vial was charged with methyl 1H-indazole-5-carboxylate (1.00 g, 5.68 mmol), copper(I) iodide (0.108 g, 0.568 mmol), cesium carbonate (1.85 g, 5.68 mmol) and 5.7 mL DMSO. The reaction mixture was evacuated and flushed with argon again. After addition of 1-iodo-4-(trifluoromethoxy)benzene (0.843 g, 2.84 mmol), the reaction mixture was heated at 100° C. After cooling, the reaction mixture was diluted with ethyl acetate. It was filtrated over celite and washed several times with ethyl acetate. The organic layer was extracted with water, brine, dried with anhydrous MgSO$_4$, filtered of and evaporated. The crude product was purified by flash-chromatography to give a mixture of methyl 1-[4-(trifluoromethoxy)-phenyl]indazole-5-carboxylate and methyl 2-[4-(trifluoromethoxy)phenyl]indazole-5-carboxylate (610 mg) as a yellow solid.

LC-MS: $t_R$=1.15 min, m/z=337 [M+1].

$^1$H NMR (400 MHz, DMSO-d6) δ ppm 3.91 (s, 3H) 7.63 (d, J=8.44 Hz, 2H) 7.92-7.99 (m, 3H) 8.07 (dd, J=8.80, 1.47 Hz, 1H) 8.61 (d, J=2.20 Hz, 2H).

Step L-2: Preparation of [1-[4-(trifluoromethoxy)phenyl]indazol-5-yl]methanol and [2-[4-(trifluoromethoxy)phenyl]indazol-5-yl]methanol

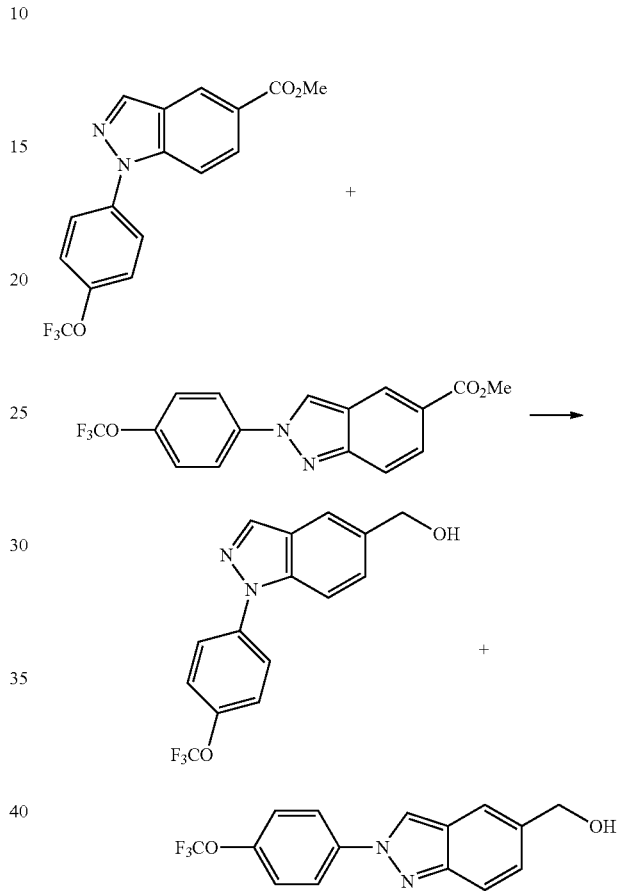

A vial under argon was charged with a mixture of methyl 1-[4-(trifluoromethoxy)phenyl]indazole-5-carboxylate and (methyl 2-[4-(trifluoromethoxy)phenyl]indazole-5-carboxylate (0.610 g, 1.72 mmol) and with diethyl ether (8.62 mL). The reaction mixture was cooled to −70° C. and a solution of DIBAL-H in dichloromethane (1N, 1.7 mL, 1.7 mmol) was added dropwise. After 1 h at this temperature, the reaction mixture was warmed to 0° C. and another 1 equivalent (1.7 mL) DIBAL-H in dichloromethane was added. The reaction mixture was stirred at 0° C. for another 30 min. After quenching at 0° C. with Rochelle salt (10 mL), the mixture was extracted twice with dichloromethane, dried over anhydrous MgSO$_4$, filtered and evaporated to give a mixture of [1-[4-(trifluoromethoxy)phenyl]indazol-5-yl]methanol and [2-[4-(trifluoro-methoxy)phenyl]indazol-5-yl]methanol (0.849 mg) as a yellow oil.

LC-MS: $t_R$=0.97 min, m/z=308 [M+1].

$^1$H NMR (400 MHz, DMSO-d6) δ ppm 4.64 (d, J=5.50 Hz, 2H) 7.49 (d, J=8.44 Hz, 1H) 7.59 (d, J=8.80 Hz, 2H) 7.81-7.88 (m, 2H) 7.93 (d, J=8.80 Hz, 2H) 8.39 (s, 1H).

Step L-3: Preparation of 1-[4-(trifluoromethoxy)phenyl]indazole-5-carbaldehyde and 2-[4-(trifluoromethoxy)phenyl]indazole-5-carbaldehyde Step L-4: Preparation of 1-(2,6-dimethylphenyl)-3-[(E)-[1-[4-(trifluoromethoxy)phenyl]indazol-5-yl]methyleneamino]thiourea

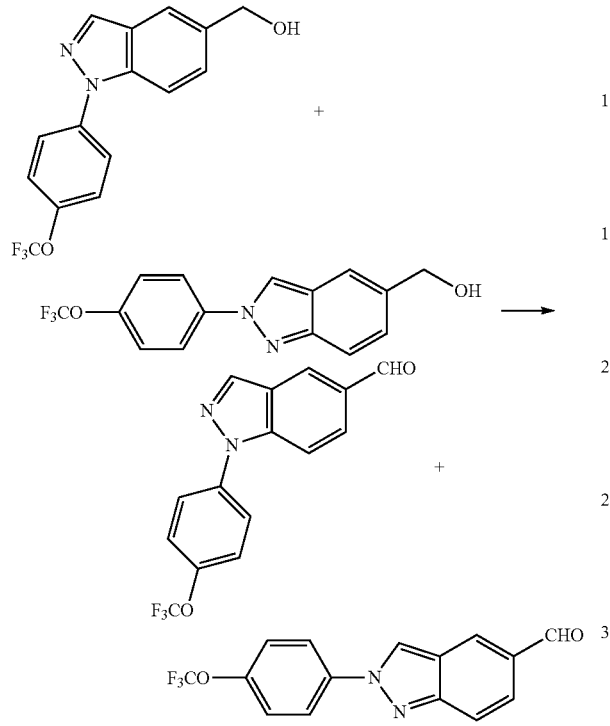

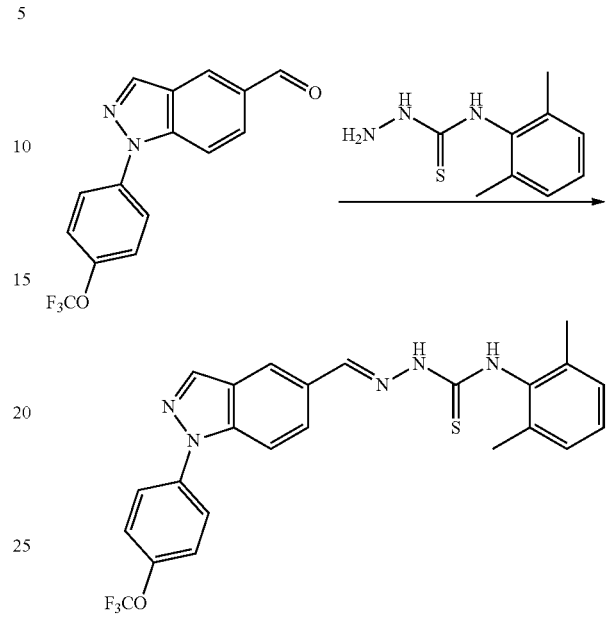

A 25 mL round bottom flask was set under argon and charged with Dess-Martin period inane (0.707 g, 1.67 mmol) suspended in dichloromethane (9.00 mL). A mixture of [1-[4-(trifluoromethoxy)phenyl]indazol-5-yl]methanol and [2-[4-(trifluoromethoxy)phenyl]indazol-5-yl]methanol (0.476 g, 1.39 mmol) in dichloromethane (4 mL) was added dropwise at room temperature. The reaction mixture was stirred at this temperature overnight. After dilution with 15 mL ethyl acetate, the mixture was poured into a mixture of saturated NaHCO$_3$ and saturated Na$_2$S$_2$O$_3$ (~40 mL, 1:1) and stirred for 10 min at 0° C. (pH~9). The solution was then extracted with ethyl acetate (100 mL), washed with saturated NaHCO$_3$ (80 mL), water (80 mL), brine (80 mL), dried over anhydrous MgSO$_4$, filtered and evaporated. The crude mixture was separated by flash-chromatography to give 1-[4-(trifluoromethoxy)phenyl]indazole-5-carbaldehyde (0.265 mg) and 2-[4-(trifluoromethoxy)phenyl]indazole-5-carbaldehyde (0.046 mg).

1-[4-(trifluoromethoxy)phenyl]indazole-5-carbaldehyde

LC-MS: t$_R$=1.07 min, m/z=307 [M+1].
$^1$H NMR (400 MHz, DMSO-d6) δ ppm 7.65 (d, J=8.44 Hz, 2H) 7.94-8.07 (m, 4H) 8.54-8.74 (m, 2H) 10.07-10.16 (m, 1H).

2-[4-(trifluoromethoxy)phenyl]indazole-5-carbaldehyde

LC-MS: tR=1.05 min, m/z=307 [M+1].
$^1$H NMR (400 MHz, DMSO-d6) δ ppm 7.67 (d, J=8.80 Hz, 2H) 7.74-7.79 (m, 1H) 7.84-7.89 (m, 1H) 8.29 (d, J=9.17 Hz, 2H) 8.57 (s, 1H) 9.52 (s, 1H) 10.05 (s, 1H).

To a solution of 1-[4-(trifluoromethoxy)phenyl]indazole-5-carbaldehyde (0.050 g, 0.16 mmol) in methanol (1.6 mL) was added 1-amino-3-(2,6-dimethylphenyl)thiourea (0.029 g, 0.15 mmol) and the reaction mixture was heated at 65° C. overnight. The reaction mixture was filtered, the solid was washed with methanol and diethyl ether to give 1-(2,6-dimethylphenyl)-3-[(E)-[1-[4-(trifluoromethoxy)phenyl]indazol-5-yl]methyleneamino]thiourea (49 mg) as a yellow solid.

LC-MS: t$_R$=1.24 min, m/z=482 [M−1], 484 [M+1].
$^1$H NMR (400 MHz, DMSO-d6) δ ppm 2.22 (s, 6H) 7.12-7.16 (m, 3H) 7.63 (d, J=8.44 Hz, 2H) 7.87 (d, J=8.80 Hz, 1H) 7.96 (d, J=9.17 Hz, 2H) 8.26-8.32 (m, 3H) 8.47 (s, 1H) 9.94 (s, 1H) 11.75 (s, 1H).

Example P24: Preparation of 1-(2,6-dimethylphenyl)-3-[(E)-[1-[4-(trifluoromethoxy)phenyl]indazol-5-yl]methyleneamino]urea (Compound P24)

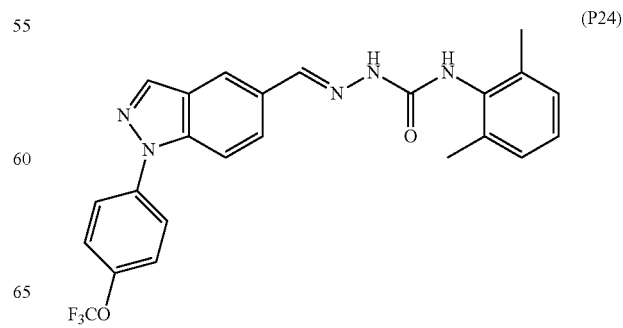

(P24)

Step M-1: Preparation of 1-(2,6-dimethylphenyl)-3-[(E)-[1-[4-(trifluoromethoxy)phenyl]indazol-5-yl]methyleneamino]urea

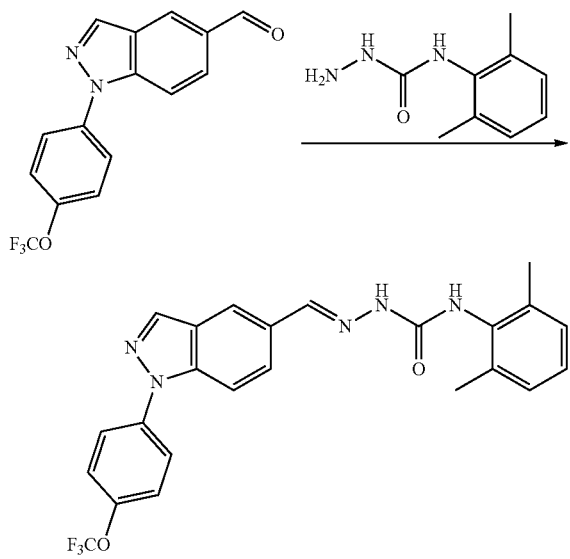

To a solution of 1-[4-(trifluoromethoxy)phenyl]indazole-5-carbaldehyde (0.050 g, 0.16 mmol, example P21, step L-3) in methanol (1.6 mL) was added 1-amino-3-(2,6-dimethylphenyl)urea (0.026 g, 0.15 mmol) and the reaction mixture was stirred 3 h at 65° C. The mixture was filtered of, washed with methanol and diethyl ether to give 1-(2,6-dimethylphenyl)-3-[(E)-[1-[4-(trifluoromethoxy)phenyl]indazol-5-yl]methyleneamino]urea (27 mg) as a white solid.

LC-MS: $t_R$=1.19 min, m/z=467 [M−1], 468 [M+1].

$^1$H NMR (400 MHz, DMSO-d6) δ ppm 2.23 (s, 6H) 7.10 (s, 3H) 7.61 (d, J=8.44 Hz, 2H) 7.87 (d, J=9.17 Hz, 1H) 7.92-7.97 (m, 2H) 8.08 (s, 1H) 8.18-8.22 (m, 2H) 8.45 (d, J=0.73 Hz, 1H) 8.57 (s, 1H) 10.57 (s, 1H).

Example P25: Preparation of 1-(2,6-dimethylphenyl)-3-[(E)-[2-[4-(trifluoromethoxy)phenyl]indazol-5-yl]methyleneamino]thiourea (Compound P25)

(P25)

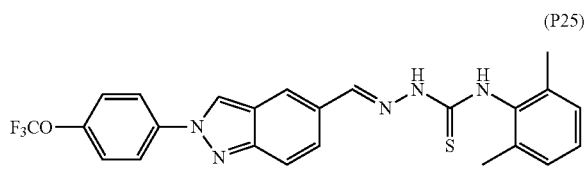 [SMILES: Cc1cccc(C)c1NC(=S)N/N=C/c1ccc2nn(-c3ccc(OC(F)(F)F)cc3)cc2c1]

Step N-1: Preparation of 1-(2,6-dimethylphenyl)-3-[(E)-[2-[4-(trifluoromethoxy)phenyl]indazol-5-yl]methyleneamino]thiourea

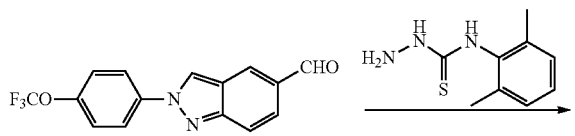

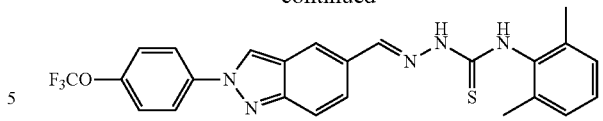

To a solution of 2-[4-(trifluoromethoxy)phenyl]indazole-5-carbaldehyde (0.023 g, 0.075 mmol, example P21, step L-3) in methanol (0.75 mL) was added 1-amino-3-(2,6-dimethylphenyl)thiourea (0.014 g, 0.071 mmol) and the reaction mixture was heated 3 h at 65° C. After cooling, it was filtered, washed with methanol and diethyl ether to give 1-(2,6-dimethylphenyl)-3-[(E)-[2-[4-(trifluoromethoxy)phenyl]indazol-5-yl]methyleneamino]thiourea (14 mg) as a yellow solid.

LC-MS: $t_R$=1.23 min, m/z=482 [M−1], 484 [M+1].

$^1$H NMR (400 MHz, DMSO-d6) δ ppm 2.22 (s, 6H) 7.10-7.15 (m, 3H) 7.63 (d, J=8.44 Hz, 2H) 7.71 (d, J=9.17 Hz, 1H) 8.00 (s, 1H) 8.22-8.30 (m, 4H) 9.19 (s, 1H) 9.91 (s, 1H) 11.72 (s, 1H).

Example P26: Preparation of 1-(2,6-dimethylphenyl)-3-[(E)-[2-[4-(trifluoromethoxy)phenyl]indazol-5-yl]methyleneamino]urea (Compound P26)

(P26)

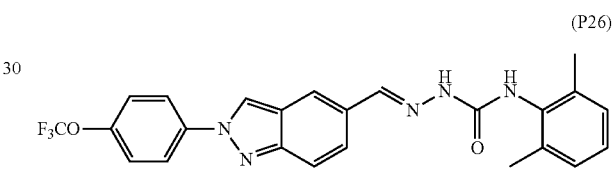

Step O-1: Preparation of 1-(2,6-dimethylphenyl)-3-[(E)-[2-[4-(trifluoromethoxy)phenyl]indazol-5-yl]methyleneamino]urea

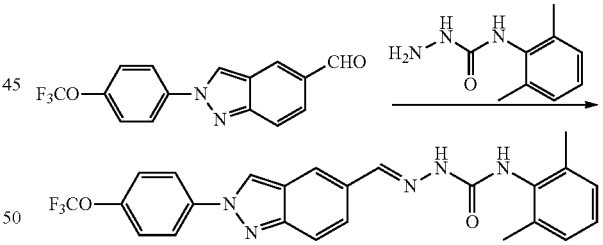

To a solution of 2-[4-(trifluoromethoxy)phenyl]indazole-5-carbaldehyde (0.023 g, 0.075 mmol, example P21, step L-3) in methanol (0.75 mL) was added 1-amino-3-(2,6-dimethylphenyl)urea (0.013 g, 0.071 mmol) and the reaction mixture was stirred at room temperature overnight. The reaction mixture was filtered and the cake was washed twice with methanol. The crude product was suspended in diethyl ether and filtered to give 1-(2,6-dimethylphenyl)-3-[(E)-[2-[4-(trifluoromethoxy)phenyl]indazol-5-yl]methyleneamino]urea (8.5 mg) as a white solid.

LC-MS: $t_R$=1.23 min, m/z=482 [M−1], 484 [M+1].

$^1$H NMR (400 MHz, DMSO-d6) δ ppm 2.24 (s, 6H) 7.11 (s, 3H) 7.63 (d, J=8.44 Hz, 2H) 7.72 (d, J=9.17 Hz, 1H) 7.94 (s, 1H) 8.04 (s, 1H) 8.17-8.30 (m, 4H) 8.57 (s, 1H) 9.18 (s, 1H) 10.56 (s, 1H).

Example P27 and P28

Preparation of 1-(2,6-dimethylphenyl)-3-[(E)-[2-[4-(trifluoromethoxy)phenyl]-indazol-5-yl]methyleneamino]urea (Compound P27) and 1-(2,6-dimethylphenyl)-3-[(E)-[3-methyl-2-[4-(trifluoromethoxy)phenyl]benzimidazol-5-yl]methyleneamino]urea (Compound P28)

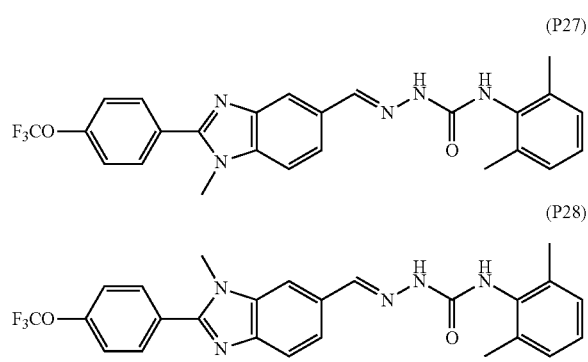

Step P-1: Preparation of methyl 3-amino-4-[[4-(trifluoromethoxy)benzoyl]amino]benzoate

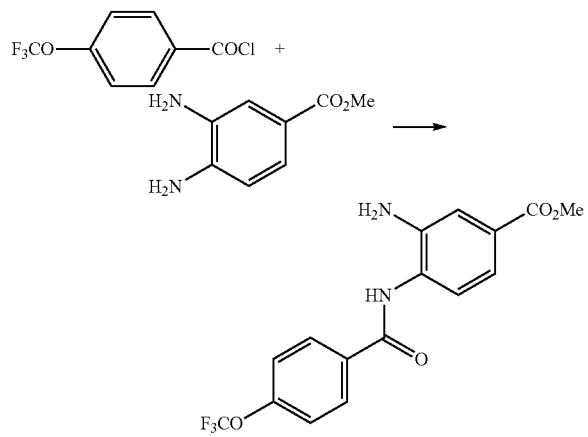

Under Argon, a solution of methyl 3,4-diaminobenzoate (5.0 g, 29.2 mmol), triethylamine (10.3 ml, 73.0 mmol) in 90 ml tetrahydrofuran was cooled to 0°-5° C. A solution of 4-(trifluoromethoxy)benzoyl chloride (4.98 ml, 30.6 mmol) in 60 ml tetrahydrofuran was added dropwise at 0°-5° C. The mixture was stirred for 2 h at 0°-5° C. and 1 h at RT. After completion of the reaction, the mixture was diluted with tert-butyl methyl ether, quenched with a saturated $NH_4Cl$-solution and extracted with 2×300 ml tert-butyl methyl ether. The combined organic layers were washed with brine and dried over $Na_2SO_4$, filtrated and evaporated to give methyl 3-amino-4-[[4-(trifluoromethoxy)benzoyl]amino]benzoate (11.2 g) as beige crystals.

LC-MS: $t_R$=0.95 min, m/z=353 [M−1], 355 [M+1].

$^1$H NMR (400 MHz, DMSO-d6) δ ppm 3.76 (s, 3H) 5.89 (s, 2H) 6.76-6.80 (m, 1H) 7.50-7.54 (m, 2H) 7.60 (dd, J=8.44, 1.83 Hz, 1H) 7.78 (d, J=1.83 Hz, 1H) 8.13 (d, J=8.80 Hz, 2H) 9.75 (s, 1H).

Step P-2: Preparation of methyl 3-amino-4-[[4-(trifluoromethoxy)benzoyl]amino]benzoate

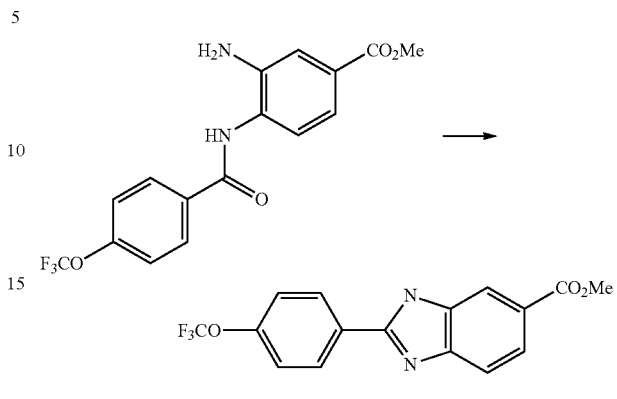

A solution of methyl 3-amino-4-[[4-(trifluoromethoxy)benzoyl]amino]benzoate (2.5 g, 6.7 mmol) in 15 ml acetic acid was irradiated in the microwave for 30 min at 140° C. The reaction mixture was then poured into water (30 mL) and the precipitate formed was filtered to give methyl 3-amino-4-[[4-(trifluoromethoxy)-benzoyl]amino]benzoate (2.7 g) as beige crystals.

LC-MS: $t_R$=1.01 min, m/z=335 [M−1], 337 [M+1].

$^1$H NMR (400 MHz, DMSO-d6) δ ppm 3.89 (s, 3H) 7.60 (d, J=8.07 Hz, 2H) 7.71 (d, J=8.44 Hz, 1H) 7.86-7.90 (m, 1H) 8.22 (s, 1H) 8.31-8.35 (m, 2H).

Step P-3: Preparation of methyl 1-methyl-2-[4-(trifluoromethoxy)phenyl]benzimidazole-5-carboxylate and methyl 3-methyl-2-[4-(trifluoromethoxy)phenyl]benzimidazole-5-carboxylate

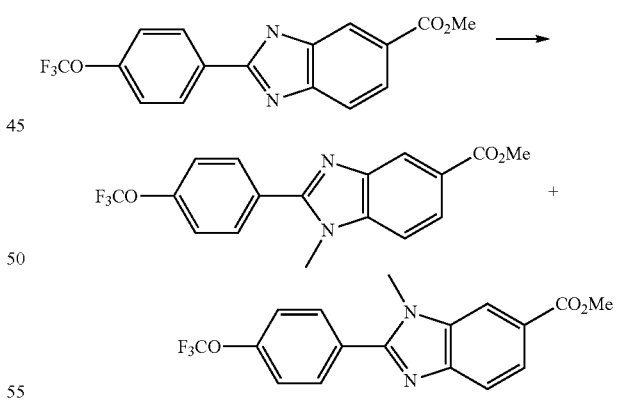

Under argon, sodium hydride (60 mg, 1.48 mmol) was suspended in 5 ml DMF and cooled to 5°-10° C. To this suspension, methyl 3-amino-4-[[4-(trifluoromethoxy)benzoyl]amino]benzoate (500 mg, 1.41 mmol) in 7 ml DMF was added dropwise at 5°-10° C. and further stirred 30 min at room temperature. Iodomethane (98 μl, 1.55 mmol) was then added dropwise at 25°-32° C. and the colourless solution was heated at 70° C. overnight. After cooling, the mixture was poured into 40 ml water, and extracted with 3×20 ml of tert-butyl methyl ether. The organic layer was washed with brine, dried over Na$_2$SO$_4$, filtrated and evaporated to give a mixture of methyl 1-methyl-2-[4-(trifluoromethoxy)phenyl]benzimidazole-5-carboxylate and methyl 3-methyl-2-[4-(trifluoromethoxy)phenyl]benzimidazole-5-carboxylate (400 mg) as a white solid.

Step P-4: Preparation of [1-methyl-2-[4-(trifluoromethoxy)phenyl]benzimidazol-5-yl]methanol and [3-methyl-2-[4-(trifluoromethoxy)phenyl]-1H-benzimidazol-5-yl]methanol

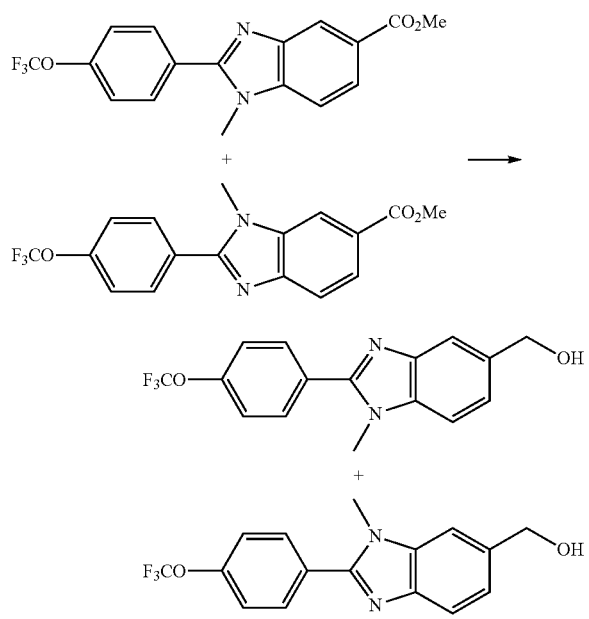

Under argon, a mixture of methyl 1-methyl-2-[4-(trifluoromethoxy)phenyl]benzimidazole-5-carboxylate and methyl 3-methyl-2-[4-(trifluoromethoxy)phenyl]benzimidazole-5-carboxylate (400 mg, 1.08 mmol) was dissolved in 8 ml tetrahydrofuran and 8 ml dichloromethane and cooled to −70° C. To this yellow solution, DIBAL-H in toluene (25%, 1.46 ml, 2.17 mmol) was added dropwise at −70°-65° C. The mixture was stirred at −70° C. for 3 hours and was allowed to warm to room temperature overnight. In order to complete the reaction, the mixture was cooled to −70° C. and additional DIBAL-H in toluene (25%, 1.46 ml, 2.17 mmol) was added dropwise at −70°-65° C. After carefully quenching with 3 ml methanol at −70° C. and 30 min stirring at −70° C., 3 ml water was added dropwise. The mixture was stirred for 30 min at −70° C. and then allowed to warm to room temperature. The organic phase was separated, and the water phase was extracted with 2×10 ml dichloromethane. The organic layer was washed with water, brine, dried over Na$_2$SO$_4$, filtrated and evaporated. The crude product was purified by flash-chromatography to give a mixture of [1-methyl-2-[4-(trifluoromethoxy)phenyl]benzimidazol-5-yl]methanol and [3-methyl-2-[4-(tri-fluoromethoxy)phenyl]-1H-benzimidazol-5-yl]methanol as an orange wax.

LC-MS: t$_R$=0.75 min, m/z=321 [M−1], 323 [M+1].

Step P-5: Preparation of 1-methyl-2-[4-(trifluoromethoxy)phenyl]benzimidazole-5-carbaldehyde and 3-methyl-2-[4-(trifluoromethoxy)phenyl]-1H-benzimidazole-5-carbaldehyde

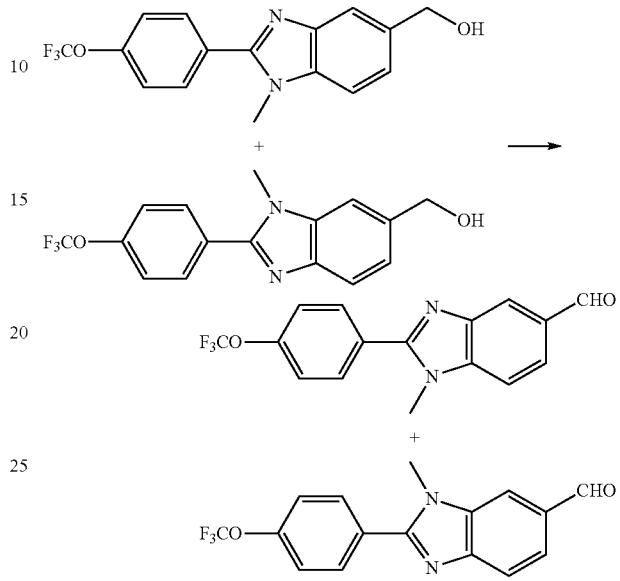

To a solution of [1-methyl-2-[4-(trifluoromethoxy)phenyl]benzimidazol-5-yl]methanol and [3-methyl-2-[4-(trifluoromethoxy)phenyl]-1H-benzimidazol-5-yl]methanol (1.97 g, 5.81 mmol) in 100 ml dichloromethane was added manganese dioxide (5.61 g, 58.1 mmol) and the mixture was stirred at rt overnight. The mixture was filtrated over a pad of celite, and the filtrate was evaporated to give a mixture of 1-methyl-2-[4-(trifluoromethoxy)phenyl]benzimidazole-5-carbaldehyde and 3-methyl-2-[4-(trifluoromethoxy)phenyl]-1H-benzimidazole-5-carbaldehyde (1.58 g).

LC-MS: t$_R$=0.98 min, m/z=321 [M−1].

$^1$H NMR (400 MHz, CDCl$_3$) δ ppm 3.96 (d, J=14.67 Hz, 6H) 7.26 (s, 2H) 7.40-7.45 (m, 4H) 7.50-7.54 (m, 1H) 7.82-7.98 (m, 7H) 8.01 (d, J=0.73 Hz, 1H) 8.31 (d, J=0.73 Hz, 1H) 10.12 (d, J=5.14 Hz, 2H).

Step P-6: Preparation of 1-(2,6-dimethylphenyl)-3-[(E)-[1-methyl-2-[4-(trifluoromethoxy)phenyl]benzimidazol-5-yl]methyleneamino]urea and 1-(2,6-dimethylphenyl)-3-[(E)-[3-methyl-2-[4-(trifluoromethoxy)phenyl]benzimidazol-5-yl]methyleneamino]urea

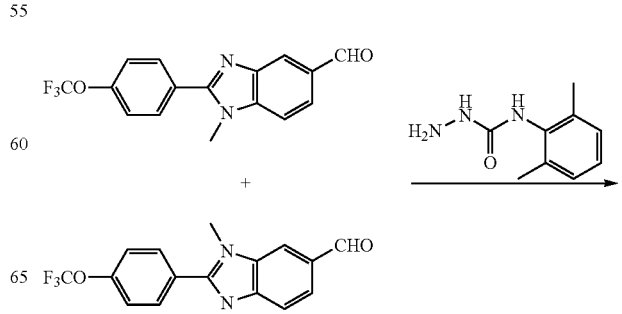

-continued

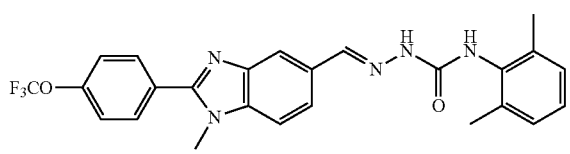

+

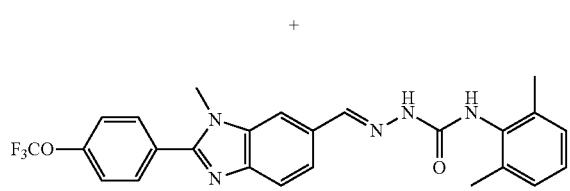

To a solution of a mixture of 1-methyl-2-[4-(trifluoromethoxy)phenyl]benzimidazole-5-carbaldehyde and 3-methyl-2-[4-(trifluoromethoxy)phenyl]-1H-benzimidazole-5-carbaldehyde (120 mg, 0.356 mmol) in 10 ml ethanol was added 1-amino-3-(2,6-dimethylphenyl)urea (71 mg, 0.374 mmol) and the reaction mixture was heated to 65° C. for 3 h. After evaporation, the crude product was purified by flash-chromatography to give 1-(2,6-dimethylphenyl)-3-[(E)-[1-methyl-2-[4-(trifluoromethoxy)phenyl]benzimidazol-5-yl]methyleneamino]urea (P27) (64 mg) and 1-(2,6-dimethylphenyl)-3-[(E)-[3-methyl-2-[4-(trifluoromethoxy)phenyl]-benzimidazol-5-yl]methyleneamino]urea (P28) (64 mg) as white crystals.

1-(2,6-dimethylphenyl)-3-[(E)-[1-methyl-2-[4-(trifluoromethoxy)phenyl]benzimidazol-5-yl]methyleneamino]urea (P27)

LC-MS: $t_R$=1.05 min, m/z=480 [M−1], 482 [M+1].
1H NMR (400 MHz, CDCl$_3$) δ ppm 2.36 (s, 6H) 3.90 (s, 3H) 7.13 (s, 3H) 7.26 (s, 1H) 7.41 (t, J=8.07 Hz, 3H) 7.62 (s, 1H) 7.74 (dd, J=8.44, 1.47 Hz, 1H) 7.81-7.86 (m, 2H) 7.94 (s, 1H) 8.01 (d, J=0.73 Hz, 1H) 9.02 (s, 1H).

1-(2,6-dimethylphenyl)-3-[(E)-[3-methyl-2-[4-(trifluoromethoxy)phenyl]benzimidazol-5-yl]methyleneamino]urea (P28)

LC-MS: $t_R$=1.05 min, m/z=480 [M−1], 482 [M+1].
$^1$H NMR (400 MHz, CDCl$_3$) δ ppm 2.37 (s, 6H) 3.93 (s, 3H) 7.14 (s, 3H) 7.26 (s, 2H) 7.41 (d, J=8.07 Hz, 2H) 7.58-7.69 (m, 3H) 7.82-7.89 (m, 3H) 7.94 (s, 1H) 8.96 (br. s., 1H).

The compounds listed in Table 14 are either prepared as disclosed herein or may be prepared in a similar manner as disclosed for the compounds above. Generally, the compounds may be prepared according to schemes 1 to 7 above or according to known methods.

TABLE 14

Examples of compounds of formula (I)

| Compound No. | Structures | Melting Point | MS/NMR |
|---|---|---|---|
| P1 | 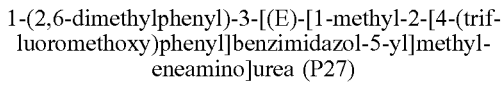 | 255-260 | MS: 484 (M + H)$^+$<br>$^1$H NMR (300 MHz, CDCl$_3$): δ 10.0 (s, 1H), 8.70 (s, 1H), 8.40 (s, 1H), 8.05 (s, 1H), 7.91-7.97 (m, 3H), 7.73 (d, 1H), 7.63 (dd, J 1H), 7.41(d, 2H), 7.15-7.26 (m, 3H), 2.35 (s, 6H). |
| P2 | 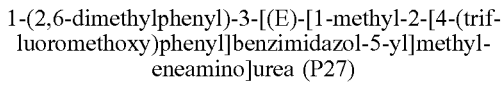 | 205-210 | MS: 525 (M + H)$^+$<br>$^1$H NMR (400 MHz, DMSO-d$_6$): δ 11.8 (s, 1H), 10.10 (s, 1H), 8.44-8.51 (m, 2H), 8.29 (s, 1H), 8.21 (d, J = 2.0 Hz, 1H), 7.62 (d, J = 12.0 Hz, 1H), 7.40-7.50 (m, 4H), 7.17-7.37 (m, 5H). |
| P3 | 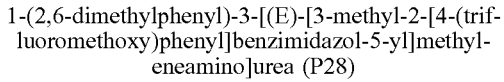 | 180-185 | MS: 531 (M + H)$^+$<br>$^1$H NMR (300 MHz, DMSO-d$_6$): δ 11.81 (s, 1H), 10.00 (s, 1H), 8.48 (s, 1H),8.19 (s, 1H), 8.04 (dd, J = 8.4Hz, J = 1.2Hz, 1H), 7.72 (d, J = 8.4Hz, 1H), 7.66-7.62 (m, 2H), 7.54 (d, J = 8.7Hz, 2H), 7.17-7.37(m, 4H). |

TABLE 14-continued

Examples of compounds of formula (I)

| Compound No. | Structures | Melting Point | MS/NMR |
|---|---|---|---|
| P4 | 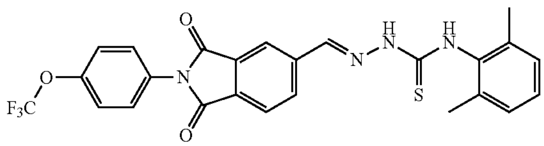 [SMILES: Cc1cccc(C)c1NC(=S)N/N=C/c1ccc2c(c1)C(=O)N(c1ccc(OC(F)(F)F)cc1)C2=O] | >240 | LC-MS: $t_R$ = 2.02 min, m/z = 511 [M − 1], 513 [M + 1]. <sup>1</sup>H NMR (400 MHz, CDCl<sub>3</sub>) δ ppm 2.34 (s, 6H) 7.18 (s, 1H) 7.18-7.18 (m, 1H) 7.37 (d, J = 8.07Hz, 2H) 7.51-7.54 (m, 2H) 8.01-8.04 (m, 3H) 8.31 (s, 1H) 8.69 (s, 1H) 10.01 (s, 1H). |
| P5 | 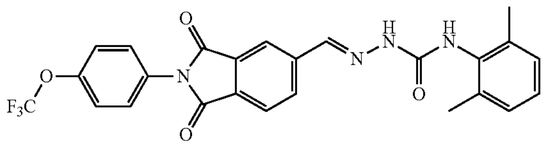 [SMILES: Cc1cccc(C)c1NC(=O)N/N=C/c1ccc2c(c1)C(=O)N(c1ccc(OC(F)(F)F)cc1)C2=O] | | <sup>1</sup>H NMR (400 MHz, DMSO-d6) δ ppm 2.22 (s, 6H) 7.54-7.66 (m, 4H) 7.97 (d, J = 7.70 Hz, 1H) 8.09 (s, 1H) 8.21 (dd, J = 8.07, 1.10Hz, 1H) 8.65 (s, 1H) 8.89 (s, 1H) 10.91 (s, 1H). |
| P6 | 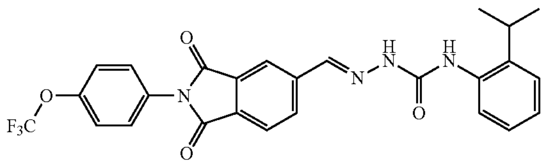 [SMILES: CC(C)c1ccccc1NC(=O)N/N=C/c1ccc2c(c1)C(=O)N(c1ccc(OC(F)(F)F)cc1)C2=O] | 239-240° C. | LC-MS: $t_R$ = 2.06 min, m/z = 509 [M − 1], 511 [M + 1]. <sup>1</sup>H NMR (400 MHz, DMSO-d6) δ ppm 1.22 (d, J = 6.97Hz, 6H) 3.15-3.25 (m, 1H) 7.18-7.22 (m, 2H) 7.31-7.35 (m, 1H) 7.39-7.44 (m, 1H) 7.54-7.58 (m, 2H) 7.60-7.64 (m, 2H) 8.00 (d, J = 7.70 Hz, 1H) 8.12 (s, 1H) 8.20 (dd, J = 7.89, 1.28Hz, 1H) 8.56 (s, 1H) 8.94 (s, 1H) 11.03 (s, 1H) |
| P7 | 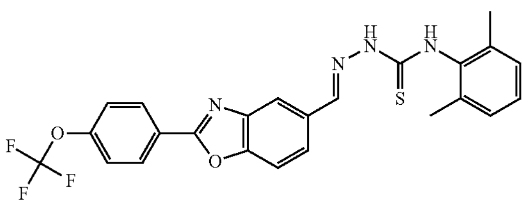 | | LC-MS: $t_R$ = 1.92 min, m/z = 495 [M − 1], 497 [M + 1]. <sup>1</sup>H NMR (400 MHz, DMSO-d6) δ ppm 2.22 (s, 6H) 7.54-7.66 (m, 4H) 7.97 (d, J = 7.70 Hz, 1H) 8.09 (s, 1H) 8.21 (dd, J = 8.07, 1.10Hz, 1H) 8.65 (s, 1H) 8.89 (s, 1H) 10.91 (s, 1H). |
| P8 | 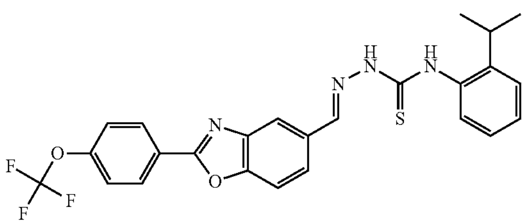 | | LC-MS: $t_R$ = 1.27 min, m/z = 4999 [M − 1], 500 [M + 1]. <sup>1</sup>H NMR (400 MHz, DMSO-d6) δ ppm 1.21 (d, J = 6.60 Hz, 7H) 3.14-3.21 (m, 1H) 7.20-7.40 (m, 4H) 7.65 (d, J = 8.07Hz, 2H) 7.86 (d, J = 8.80 Hz, 1H) 8.00 (d, J = 8.07Hz, 1H) 8.23-8.36 (m, 3H) 8.53 (s, 1H) 10.13 (s, 1H) 11.84 (s, 1H) |
| P9 | 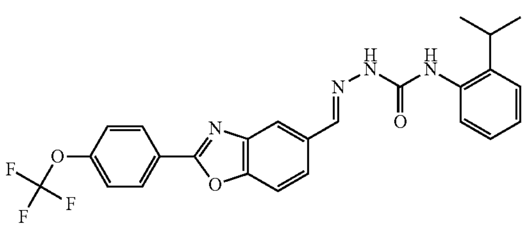 | | LC-MS: $t_R$ = 1.30 min, m/z = 481 [M − 1], 483 [M + 1]. <sup>1</sup>H NMR (400 MHz, DMSO-d6) δ ppm 1.25 (d, J = 6.97Hz, 6H) 3.20-3.27 (m, 1H) 7.17-7.24 (m, 2H) 7.31-7.37 (m, 1H) 7.47-7.52 (m, 1H) 7.65 (d, J = 8.07Hz, 2H) 7.84-7.96 (m, 2H) 8.10 (s, 1H) 8.32-8.37 (m, 3H) 8.74 (s, 1H) 10.79 (s, 1H) |
| P10 | 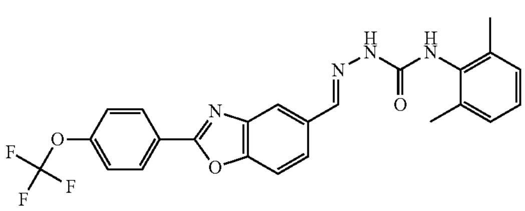 [SMILES: Cc1cccc(C)c1NC(=O)N/N=C/c1ccc2oc(-c3ccc(OC(F)(F)F)cc3)nc2c1] | | LC-MS: $t_R$ = 1.23 min, m/z = 467 [M − 1], 469 [M + 1]. <sup>1</sup>H NMR (400 MHz, DMSO-d6) δ ppm 2.24 (s, 6H) 7.11 (s, 3H) 7.65 (d, J = 8.07Hz, 2H) 7.83 (d, J = 8.80 Hz, 1H) 7.98 (d, J = 8.80 Hz, 1H) 8.06 (s, 1H) 8.34 (d, J = 8.44Hz, 2H) 8.40 (s, 1H) 8.67 (s, 1H) 10.65 (s, 1H). |
| P11 | 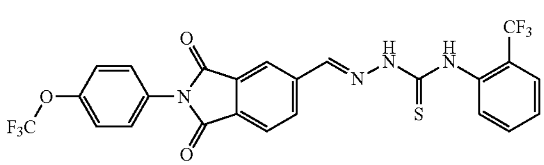 [SMILES: O=C1c2ccc(/C=N/NC(=S)Nc3ccccc3C(F)(F)F)cc2C(=O)N1c1ccc(OC(F)(F)F)cc1] | 235-236° C. | LC-MS: $t_R$ = 2,04 min, m/z = 551 [M − 1], 553 [M + 1]. <sup>1</sup>H NMR (400 MHz, CDCl<sub>3</sub>) δ ppm 7.32-7.42 (m, 3H) 7.51-7.56 (m, 2H) 7.66 (t, J = 7.89Hz, 1H) 7.73 (d, J = 7.70 Hz, 1H) 7.99-8.04 (m, 2H) 8.06-8.10 (m, 1H) 8.23-8.31 (m, 2H) 9.56 (s, 1H) 9.73-9.77 (m, 1H) 9.73-9.77 (m, 1H) 9.73-9.77 (m, 1H) 9.74 (s, 1H). |

TABLE 14-continued

Examples of compounds of formula (I)

| Compound No. | Structures | Melting Point | MS/NMR |
|---|---|---|---|
| P12 | 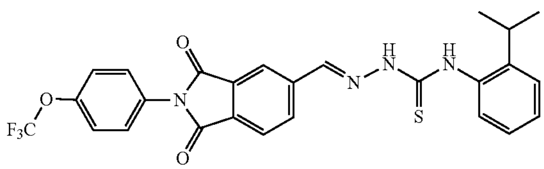 [SMILES: CC(C)c1ccccc1NC(=S)N/N=C/c1ccc2c(c1)C(=O)N(c1ccc(OC(F)(F)F)cc1)C2=O] | | LC-MS: $t_R$ = 2.11 min, m/z = 525 [M − 1], 527 [M + 1]. $^1$H NMR (400 MHz, CDCl$_3$) δ ppm 1.32 (d, J = 6.97 Hz, 6H) 3.18 (quin, J = 6.88Hz, 1H) 7.31 (dd, J = 7.70, 1.83Hz, 1H) 7.35-7.43 (m, 4H) 7.50-7.54 (m, 2H) 7.61 (d, J = 6.60 Hz, 1H) 8.00-8.06 (m, 3H) 8.31 (s, 1H) 9.02 (s, 1H) 10.03 (s, 1H). |
| P13 | 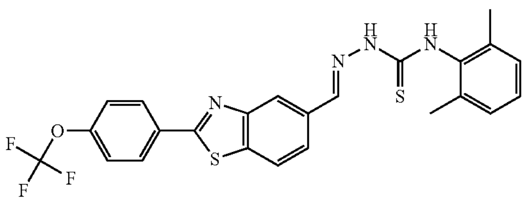 [SMILES: Cc1cccc(C)c1NC(=S)N/N=C/c1ccc2sc(-c3ccc(OC(F)(F)F)cc3)nc2c1] | | LC-MS: $t_R$ = 1.26 min, m/z = 499 [M − 1], 501 [M + 1]. $^1$H NMR (400 MHz, DMSO-d6) δ ppm 2.22 (s, 6H) 7.13 (br. s., 3H) 7.59 (d, J = 8.07Hz, 2H) 8.04 (d, J = 8.07Hz, 1H) 8.14-8.33 (m, 4H) 8.70 (s, 1H) 10.06 (br. s., 1H) 11.85 (br. s., 1H). |
| P14 | 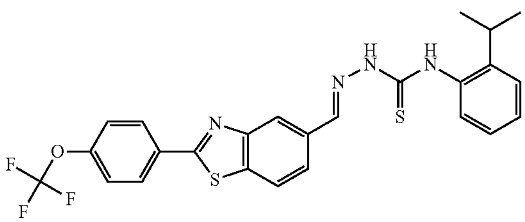 | | LC-MS: $t_R$ = 1.35 min, m/z = 513 [M − 1], 515 [M + 1]. $^1$H NMR (400 MHz, DMSO-d6) δ ppm 1.20 (d, J = 6.60 Hz, 6H) 3.13-3.20 (m, 1H) 7.17-7.26 (m, 2H) 7.29-7.39 (m, 2H) 7.59 (d, J = 8.44Hz, 2H) 8.03 (d, J = 8.44Hz, 1H) 8.21 (t, J = 4.22Hz, 2H) 8.29 (s, 1H) 8.70 (s, 1H) 10.18 (s, 1H) 11.86 (s, 1H) |
| P15 | 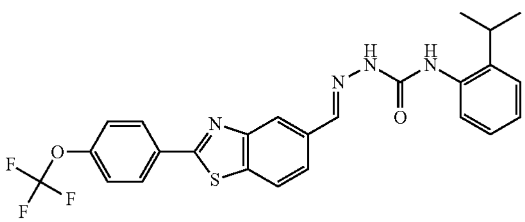 | | LC-MS: $t_R$ = 1.29 min, m/z = 497 [M − 1], 499 [M + 1]. $^1$H NMR (400 MHz, DMSO-d6) δ ppm 1.23 (d, J = 6.97Hz, 6H) 3.20-3.26 (m, 1H) 7.16-7.23 (m, 2H) 7.31-7.36 (m, 1H) 7.44-7.51 (m, 1H) 7.59 (d, J = 8.07Hz, 2H) 7.95-8.01 (m, 1H) 8.11 (s, 1H) 8.19-8.27 (m, 3H) 8.51 (s, 1H) 8.78 (s, 1H) 10.82 (s, 1H) |
| P16 | 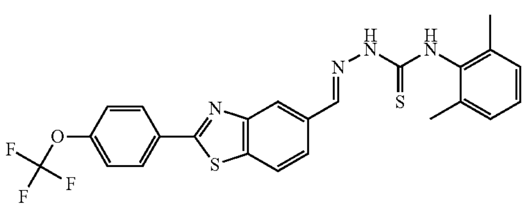 | | LC-MS: $t_R$ = 1.21 min, m/z = 483 [M − 1], 485 [M + 1]. $^1$H NMR (400 MHz, DMSO-d6) δ ppm 2.23 (s, 6H) 7.10 (s, 3H) 7.59 (d, J = 8.07Hz, 2H) 8.00-8.08 (m, 2H) 8.17-8.25 (m, 3H) 8.57 (s, 1H) 8.71 (s, 1H) 10.68 (s, 1H). |
| P17 | 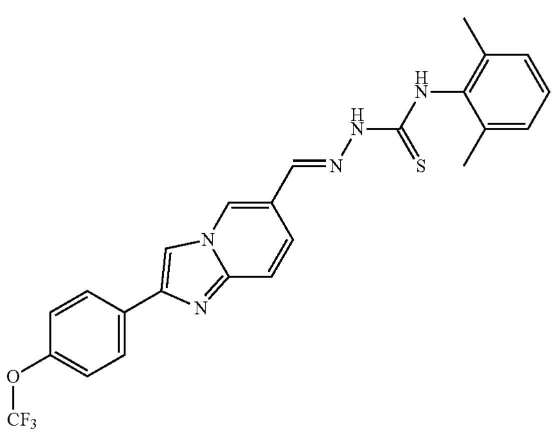 | | LC-MS: $t_R$ = 1.82 min, m/z = 483 [M − 1], 484 [M + 1]. $^1$H NMR (400 MHz, DMSO-d6) δ ppm 2.21 (s, 6H) 7.11-7.15 (m, 3H) 7.46 (d, J = 8.07Hz, 2H) 7.60 (d, J = 9.54Hz, 1H) 8.07-8.11 (m, 2H) 8.16 (s, 1H) 8.21 (dd, J = 9.54, 1.83Hz, 1H) 8.42 (s, 1H) 8.90 (s, 1H) 9.95 (s, 1H) 11.85 (s, 1H). |

TABLE 14-continued

Examples of compounds of formula (I)

| Compound No. | Structures | Melting Point | MS/NMR |
|---|---|---|---|
| P18 | 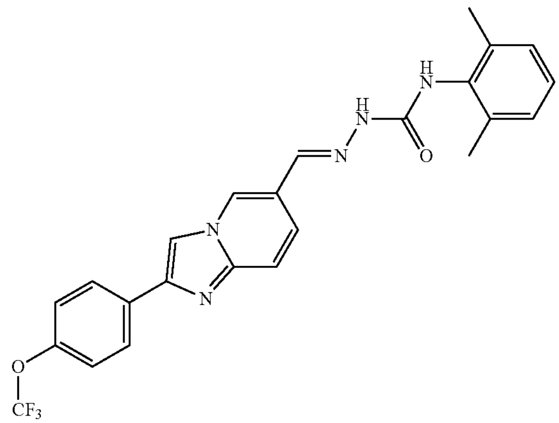 | | LC-MS: $t_R$ = 1.82 min, m/z = 483 [M − 1], 484 [M + 1]. $^1$H NMR (400 MHz, DMSO-d6) δ ppm 2.23 (s, 6H) 7.11 (s, 3H) 7.45 (d, J = 8.07Hz, 2H) 7.60 (d, J = 9.17Hz, 1H) 7.96 (s, 1H) 8.08-8.16 (m, 3H) 8.42 (s,1H) 8.62 (s, 1H) 8.82 (s, 1H) 10.69 (s, 1 H). |
| P19 | 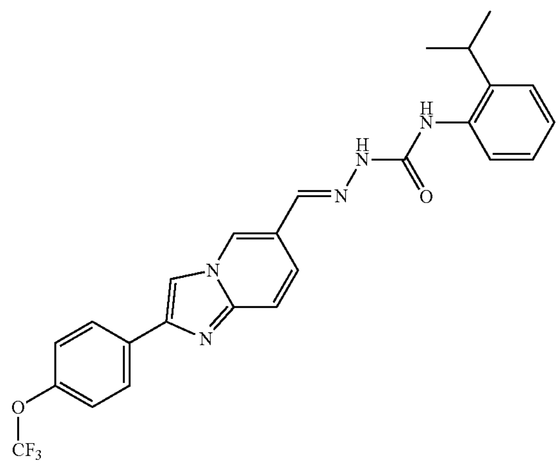 [SMILES: CC(C)c1ccccc1NC(=O)N/N=C/c1ccc2nc(-c3ccc(OC(F)(F)F)cc3)cn2c1] | | LC-MS: $t_R$ = 1.83 min, m/z = 480 [M − 1], 482 [M + 1]. $^1$H NMR (400 MHz, DMSO-d6) δ ppm 1.23 (d, J = 6.97Hz, 6H) 3.21 (quin, J = 6.88Hz, 1H) 7.17-7.22 (m, 2H) 7.31-7.36 (m, 1H) 7.43-7.48 (m, 3 H) 7.64 (d, J = 9.54Hz, 1H) 7.98-8.02 (m, 2H) 8.09-8.14 (m, 2H) 8.44 (s, 1H) 8.68 (s, 1H) 8.83 (s, 1H) 10.81 (s, 1H) |
| P20 | 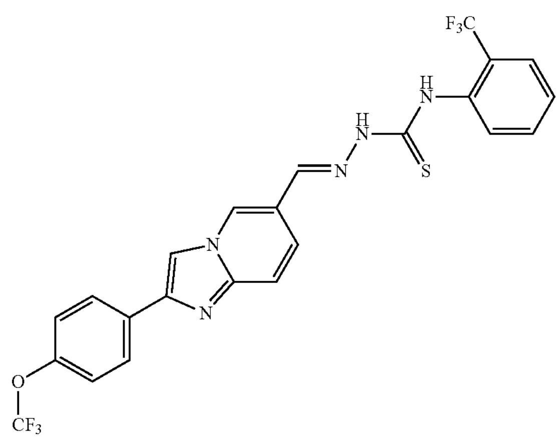 [SMILES: FC(F)(F)Oc1ccc(-c2cn3cc(/C=N/NC(=S)Nc4ccccc4C(F)(F)F)ccc3n2)cc1] | | LC-MS: $t_R$ = 1.87 min, m/z = 522 [M − 1], 524 [M + 1]. $^1$H NMR (400 MHz, DMSO-d6) δ ppm 7.46 (d, J = 8.07Hz, 2H) 7.50-7.58 (m, 1H) 7.62-7.68 (m, 2H) 7.72-7.82 (m, 2H) 8.07-8.14 (m, 3H) 8.20 (s, 1 H) 8.45 (s, 1H) 8.91 (s, 1H) 10.09 (s, 1H) 12.11 (s, 1H) |
| P21 | 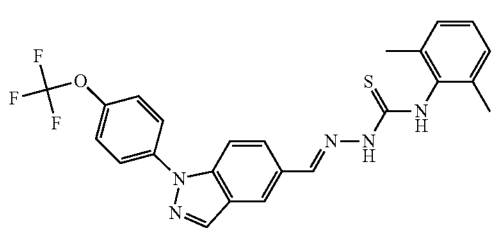 [SMILES: Cc1cccc(C)c1NC(=S)N/N=C/c1ccc2c(cnn2-c2ccc(OC(F)(F)F)cc2)c1] | 233-239° C. | LC-MS: $t_R$ = 1.24 min, m/z = 482 [M − 1], 484 [M + 1]. $^1$H NMR (400 MHz, DMSO-d6) δ ppm 2.22 (s, 6H) 7.12-7.16 (m, 3H) 7.63 (d, J = 8.44Hz, 2H) 7.87 (d, J = 8.80 Hz, 1H) 7.96 (d, J = 9.17Hz, 2H) 8.26-8.32 (m, 3H) 8.47 (s, 1H) 9.94 (s, 1H) 11.75 (s, 1 H). |

TABLE 14-continued

Examples of compounds of formula (I)

| Compound No. | Structures | Melting Point | MS/NMR |
|---|---|---|---|
| P22 | 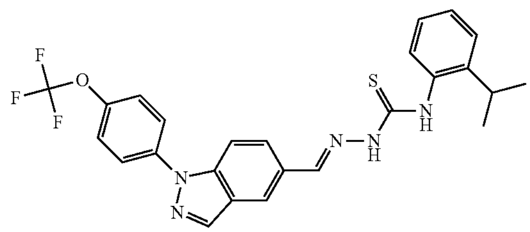 [SMILES: CC(C)c1ccccc1NC(=S)N/N=C/c1ccc2c(cnn2-c2ccc(OC(F)(F)F)cc2)c1] | 214-222° C. | LC-MS: $t_R$ = 1.24 min, m/z = 496 [M − 1], 498 [M + 1]. $^1$H NMR (400 MHz, DMSO-d6) δ ppm 1.11-1.27 (m, 6H) 3.16 (dt, J = 13.57, 6.79Hz, 1H) 7.20-7.41 (m, 4H) 7.62 (d, J = 8.80 Hz, 2H) 7.89 (d, J = 9.17 Hz,1H) 7.96 (d, J = 8.80 Hz, 2H) 8.23-8.34 (m, 3 H) 8.48 (s, 1H) 10.04 (s, 1H) 11.79 (s, 1H) |
| P23 | 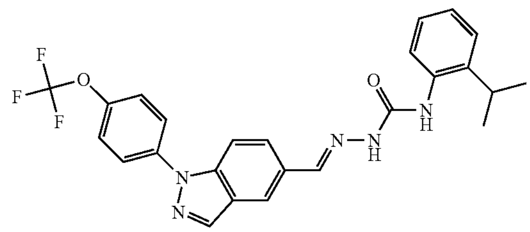 [SMILES: CC(C)c1ccccc1NC(=O)N/N=C/c1ccc2c(cnn2-c2ccc(OC(F)(F)F)cc2)c1] | 207-213° C. | LC-MS: $t_R$ = 1.23 min, m/z = 480 [M − 1], 482 [M + 1]. $^1$H NMR (400 MHz, DMSO-d6) δ ppm 1.27 (d, J = 6.60 Hz, 6H) 3.21 (quin, J = 6.79 Hz, 1H) 7.15-7.24 (m, 2H) 7.34 (dd, J = 7.52, 2.02Hz, 1H) 7.58-7.66 (m, 3H) 7.93-8.00 (m, 3H) 8.10-8.21 (m, 3 H) 8.49 (s, 1H) 8.67 (s, 1H) 10.78 (s, 1H). |
| P24 | 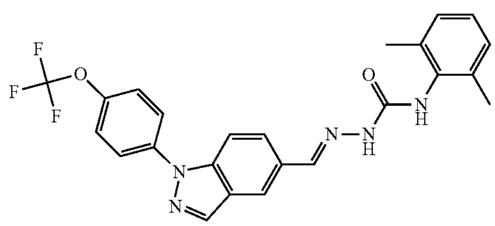 [SMILES: Cc1cccc(C)c1NC(=O)N/N=C/c1ccc2c(cnn2-c2ccc(OC(F)(F)F)cc2)c1] | 227-233° C. | LC-MS: $t_R$ = 1.19 min, m/z = 467 [M − 1], 468 [M + 1]. $^1$H NMR (400 MHz, DMSO-d6) δ ppm 2.23 (s, 6H) 7.10 (s, 3H) 7.61 (d, J = 8.44Hz, 2H) 7.87 (d, J = 9.17Hz, 1H) 7.92-7.97 (m, 2H) 8.08 (s, 1H) 8.18-8.22 (m, 2H) 8.45 (d, J = 0.73Hz, 1H) 8.57 (s, 1H) 10.57 (s, 1H). |
| P25 | 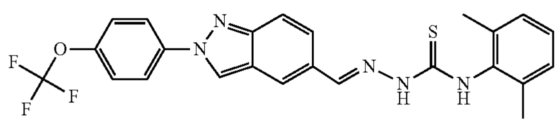 [SMILES: Cc1cccc(C)c1NC(=S)N/N=C/c1ccc2nn(-c3ccc(OC(F)(F)F)cc3)cc2c1] | 225-234° C. | LC-MS: $t_R$ = 1.23 min, m/z = 482 [M − 1], 484 [M + 1]. $^1$H NMR (400 MHz, DMSO-d6) δ ppm 2.22 (s, 6H) 7.10-7.15 (m, 3H) 7.63 (d, J = 8.44Hz, 2H) 7.71 (d, J = 9.17Hz, 1H) 8.00 (s, 1H) 8.22-8.30 (m, 4 H) 9.19(s, 1H) 9.91 (s, 1H) 11.72 (s, 1H). |
| P26 | 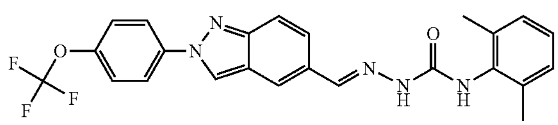 | 244-250° C. | LC-MS: $t_R$ = 1.23 min, m/z = 482 [M − 1], 484 [M + 1]. $^1$H NMR (400 MHz, DMSO-d6) δ ppm 2.24 (s, 6H) 7.11 (s, 3H) 7.63 (d, J = 8.44Hz, 2H) 7.72 (d, J = 9.17Hz, 1H) 7.94 (s, 1H) 8.04 (s, 1H) 8.17-8.30 (m,4H) 8.57 (s, 1H) 9.18 (s, 1H) 10.56 (s, 1 H). |
| P27 | 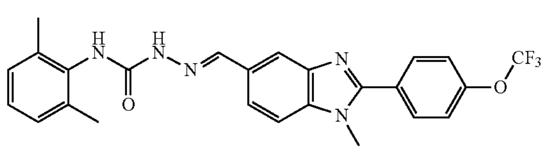 | >245° C. | LC-MS: $t_R$ = 1.05 min, m/z = 480 [M − 1], 482 [M + 1]. $^1$H NMR (400 MHz, CDCl$_3$) δ ppm 2.36 (s, 6H) 3.90 (s, 3H) 7.13 (s, 3H) 7.26 (s, 1H) 7.41 (t, J = 8.07Hz, 3H) 7.62 (s, 1H) 7.74 (dd, J = 8.44, 1.47Hz, 1H) 7.81-7.86 (m, 2H) 7.94 (s, 1H) 8.01 (d, J = 0.73Hz, 1H) 9.02 (s, 1H). |
| P28 | 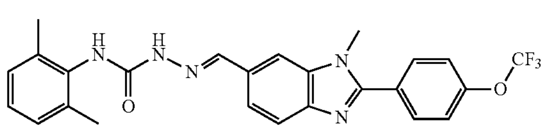 [SMILES: Cc1cccc(C)c1NC(=O)N/N=C/c1ccc2nc(-c3ccc(OC(F)(F)F)cc3)n(C)c2c1] | 218-219° C. | LC-MS: $t_R$ = 1.05 min, m/z = 480 [M − 1], 482 [M + 1]. $^1$H NMR (400 MHz, CDCl$_3$) δ ppm 2.37 (s, 6H) 3.93 (s, 3H) 7.14 (s, 3H) 7.26 (s, 2H) 7.41 (d, J = 8.07 Hz, 2H) 7.58-7.69 (m, 3H) 7.82-7.89 (m, 3H) 7.94 (s, 1H) 8.96 (br. s., 1H) |
| P29 | 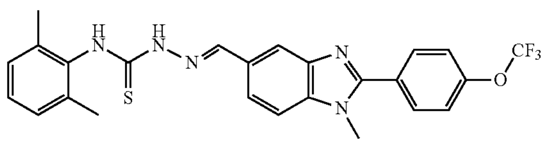 [SMILES: Cc1cccc(C)c1NC(=S)N/N=C/c1ccc2c(c1)nc(-c1ccc(OC(F)(F)F)cc1)n2C] | 219-221° C. | LC-MS: $t_R$ = 1.11 min, m/z = 496 [M − 1], 498 [M + 1]. $^1$H NMR (400 MHz, CDCl$_3$) δ ppm 2.33-2.37 (m, 6 H) 3.92-3.96 (m, 3H) 7.12-7.22 (m, 3H) 7.37-7.48 (m, 3H) 7.78 (d, J = 8.80 Hz, 1H) 7.88 (d, J = 8.80 Hz, 2H) 8.02 (s, 1H) 8.10 (s, 1H) 8.70 (s, 1H) 9.44 (br. s., 1H) |

TABLE 14-continued

Examples of compounds of formula (I)

| Compound No. | Structures | Melting Point | MS/NMR |
|---|---|---|---|
| P30 | 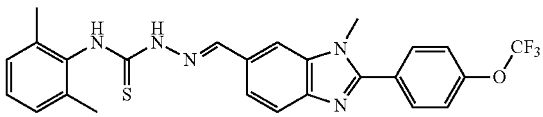 [SMILES: Cc1cccc(C)c1NC(=S)N/N=C/c1ccc2nc(-c3ccc(OC(F)(F)F)cc3)n(C)c2c1] | 230-259° C. | LC-MS: $t_R$ = 1.10 min, m/z = 496 [M − 1], 498 [M + 1]. $^1$H NMR (400 MHz, MeOH-d4) δ ppm 2.32-2.35 (m, 6H) 3.97 (s, 3H) 7.12-7.18 (m, 3H) 7.55 (d, J = 8.07Hz, 2H) 7.72-7.76 (m, 1H) 7.80-7.83 (m, 1H) 7.94-7.98 (m, 2H) 8.20 (s, 1H) 8.24 (s, 1 H) |
| P31 | 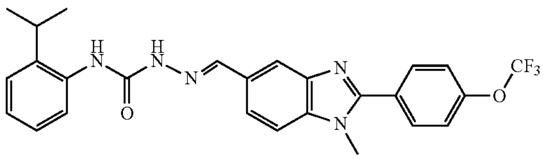 [SMILES: CC(C)c1ccccc1NC(=O)N/N=C/c1ccc2c(c1)nc(-c1ccc(OC(F)(F)F)cc1)n2C] | 216-217° C. | LC-MS: $t_R$ = 1.13 min, m/z = 494 [M − 1], 496 [M + 1]. $^1$H NMR (400 MHz, CDCl$_3$) δ ppm 1.35-1.40 (m, 6 H) 3.19 (quin, J = 6.88Hz, 1H) 3.93 (s, 3H) 7.12-7.18 (m, 1H) 7.22-7.26 (m, 2H) 7.31 (dd, J = 7.70, 1.47Hz, 1H) 7.44 (dd, J = 14.86, 8.25 Hz, 3H) 7.76 (dd, J = 8.44, 1.47Hz, 1H) 7.85-7.96 (m, 4H) 8.03 (s, 1H) 8.22 (s, 1H) |
| P32 | 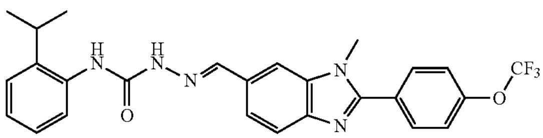 [SMILES: CC(C)c1ccccc1NC(=O)N/N=C/c1ccc2nc(-c3ccc(OC(F)(F)F)cc3)n(C)c2c1] | 237-239° C. | LC-MS: $t_R$ = 1.12 min, m/z = 494 [M − 1], 496 [M + 1]. $^1$H NMR (400 MHz, CDCl$_3$) δ ppm 1.36-1.40 (m, 7 H) 3.23 (quin, J = 6.88Hz, 1H) 3.94 (s, 3H) 7.14-7.19 (m, 1H) 7.33 (dd, J = 7.70, 1.47Hz, 1H) 7.42 (d, J = 8.07Hz, 2H) 7.65-7.70 (m, 2H) 7.87 (d, J = 8.80 Hz, 3H) 7.92-7.97 (m, 2H) 8.28 (s, 1H) 8.77 (br. s., 1H) |
| P33 | 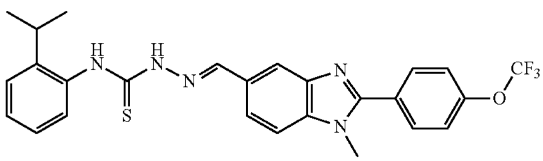 [SMILES: CC(C)c1ccccc1NC(=S)N/N=C/c1ccc2c(c1)nc(-c1ccc(OC(F)(F)F)cc1)n2C] | | LC-MS: $t_R$ = 1.16 min, m/z = 510 [M − 1], 512 [M + 1]. $^1$H NMR (400 MHz, CDCl$_3$) δ ppm 1.27-1.34 (m, 6 H) 3.16-3.25 (m, 1H) 7.27-7.36 (m, 2H) 7.36-7.47 (m, 4H) 7.65 (dd, J = 7.70, 1.47Hz, 1H) 7.74 (dd, J = 8.44, 1.47Hz, 1H) 7.81-7.86 (m, 2H) 8.03-8.08 (m, 2H) 9.04 (s, 1H) 9.63 (br. s., 1 H). |
| P34 | 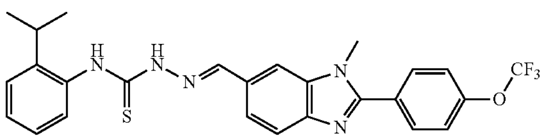 | 205-207° C. | LC-MS: $t_R$ = 1.16 min, m/z = 510 [M − 1], 512 [M + 1]. $^1$H NMR (400 MHz, CDCl$_3$) δ ppm 1.33 (d, J = 6.97 Hz, 6H) 3.18-3.26 (m, 1H) 7.27-7.37 (m, 2H) 7.37-7.43 (m, 3H) 7.64-7.72 (m, 3H) 7.82-7.87 (m, 3H) 8.06 (s, 1H) 9.06 (s, 1H) 9.67 (s, 1H) |
| P35 | 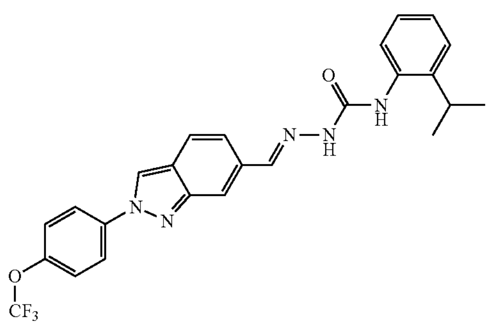 [SMILES: CC(C)c1ccccc1NC(=O)N/N=C/c1ccc2cn(-c3ccc(OC(F)(F)F)cc3)nc2c1] | | LC-MS: $t_R$ = 2.11 min, m/z = 480 [M − 1], 482 [M + 1]. $^1$H NMR (400 MHz, CDCl$_3$) δ ppm 1.38 (d, J = 6.97 Hz, 6H) 3.16-3.26 (m, 1H) 7.14-7.20 (m, 1H) 7.32 (dd, J = 7.70, 1.47Hz, 1H) 7.41 (d, J = 8.44Hz, 2H) 7.64 (dd, J = 8.80, 1.10Hz, 1H) 7.75 (d, J = 9.17Hz, 1H) 7.84 (s, 1H) 7.89-7.99 (m, 4H) 8.24 (s, 1H) 8.39-8.45 (m, 2H) |
| P36 | 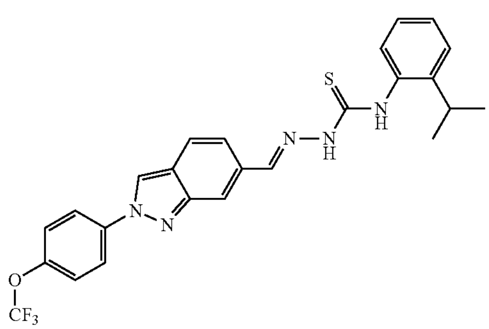 | | LC-MS: $t_R$ = 2.15 min, m/z = 496 [M − 1], 498 [M + 1]. $^1$H NMR (400 MHz, CDCl$_3$) δ ppm 1.32 (d, J = 6.97 Hz, 6H) 3.20 (dt, J = 13.66, 6.92Hz, 1H) 7.28-7.36 (m, 2H) 7.37-7.43 (m, 3H) 7.64 (ddd, J = 10.09, 8.44, 1.28Hz, 2H) 7.74 (d, J = 8.80 Hz, 1 H) 7.92 (s, 1H) 7.93-7.99 (m, 3H) 8.41 (d, J = 0.73 Hz, 1H) 9.03 (s, 1H) 9.33 (s, 1H) |

Formulation Examples (%=Percent by Weight)

Example F1: Emulsion concentrates

|  | a) | b) | c) |
|---|---|---|---|
| Active ingredient | 25% | 40% | 50% |
| Calcium dodecylbenzenesulfonate | 5% | 8% | 6% |
| Castor oil polyethylene glycol ether (36 mol of EO) | 5% | — | — |
| Tributylphenoxypolyethylene glycol ether (30 mol of EO) | — | 12% | 4% |
| Cyclohexanone | — | 15% | 20% |
| Xylene mixture | 65% | 25% | 20% |

Emulsions of any desired concentration can be prepared from such concentrates by dilution with water.

Example F2: Solutions

|  | a) | b) | c) | d) |
|---|---|---|---|---|
| Active ingredient | 80% | 10% | 5% | 95% |
| Ethylene glycol monomethyl ether | 20% | — | — | — |
| Polyethylene glycol MW 400 | — | 70% | — | — |
| N-Methylpyrrolid-2-one | — | 20% | — | — |
| Epoxidized coconut oil | — | — | 1% | 5% |
| Petroleum ether (boiling range: 160-190°) | — | — | 94% | — |

The solutions are suitable for use in the form of microdrops.

Example F3: Granules

|  | a) | b) | c) | d) |
|---|---|---|---|---|
| Active ingredient | 5% | 10% | 8% | 21% |
| Kaolin | 94% | — | 79% | 54% |
| Highly disperse silica | 1% | — | 13% | 7% |
| Attapulgite | — | 90% | — | 18% |

The active ingredient is dissolved in dichloromethane, the solution is sprayed onto the carrier(s), and the solvent is subsequently evaporated in vacuo.

Example F4: Dusts

|  | a) | b) |
|---|---|---|
| Active ingredient | 2% | 5% |
| Highly disperse silica | 1% | 5% |
| Talc | 97% | — |
| Kaolin | — | 90% |

Ready-to-use dusts are obtained by intimately mixing the carriers and the active ingredient.

Example F5: Wettable powders

|  | a) | b) | c) |
|---|---|---|---|
| Active ingredient | 25% | 50% | 75% |
| Sodium lignosulfonate | 5% | 5% | — |
| Sodium lauryl sulfate | 3% | — | 5% |
| Sodium diisobutyl-naphthalenesulfonate | — | 6% | 10% |
| Octylphenoxypolyethylene glycol ether (7-8 mol of EO) | — | 2% | — |
| Highly disperse silica | 5% | 10% | 10% |
| Kaolin | 62% | 27% | — |

The active ingredient is mixed with the additives and the mixture is ground thoroughly in a suitable mill. This gives wettable powders, which can be diluted with water to give suspensions of any desired concentration.

Example F6: Extruder granules

| Active ingredient | 10% |
|---|---|
| Sodium lignosulfonate | 2% |
| Carboxymethylcellulose | 1% |
| Kaolin | 87% |

The active ingredient is mixed with the additives, and the mixture is ground, moistened with water, extruded, granulated and dried in a stream of air.

Example F7: Coated granules

| Active ingredient | 3% |
|---|---|
| Polyethylene glycol (MW 200) | 3% |
| Kaolin | 94% |

In a mixer, the finely ground active ingredient is applied uniformly to the kaolin, which has been moistened with the polyethylene glycol. This gives dust-free coated granules.

Example F8: Suspension concentrate

| Active ingredient | 40% |
|---|---|
| Ethylene glycol | 10% |
| Nonylphenoxypolyethylene glycol ether (15 mol of EO) | 6% |
| Sodium lignosulfonate | 10% |
| Carboxymethylcellulose | 1% |
| 37% aqueous formaldehyde solution | 0.2% |
| Silicone oil (75% aqueous emulsion) | 0.8% |
| Water | 32 |

The finely ground active ingredient is mixed intimately with the additives. Suspensions of any desired concentration can be prepared from the thus resulting suspension concentrate by dilution with water.

Example F9: Powders for dry seed treatment

|  | a) | b) | c) |
|---|---|---|---|
| active ingredient | 25% | 50% | 75% |
| light mineral oil | 5% | 5% | 5% |
| highly dispersed silicic acid | 5% | 5% | — |
| Kaolin | 65% | 40% | — |
| Talcum | — | — | 20% |

The combination is thoroughly mixed with the adjuvants and the mixture is thoroughly ground in a suitable mill, affording powders that can be used directly for seed treatment.

| Example F10: Emulsifiable concentrate | |
| --- | --- |
| active ingredient | 10% |
| octylphenol polyethylene glycol ether (4-5 mol of ethylene oxide) | 3% |
| calcium dodecylbenzenesulfonate | 3% |
| castor oil polyglycol ether (35 mol of ethylene oxide) | 4% |
| Cyclohexanone | 30% |
| xylene mixture | 50% |

Emulsions of any required dilution, which can be used in plant protection, can be obtained from this concentrate by dilution with water.

| Example F11: Flowable concentrate for seed treatment | |
| --- | --- |
| active ingredients | 40% |
| propylene glycol | 5% |
| copolymer butanol PO/EO | 2% |
| Tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground combination is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

The activity of compositions comprising compounds according to the invention can be broadened considerably, and adapted to prevailing circumstances, by including other active substances. The active substances can be of chemical or biological in type, and in the case of biological could be further modified from the biological species derived in nature. Active substances include substances that control, repel or attract pests that damage or harm useful plants in general, but also substances that improve the growth of a useful plant, such as plant growth regulators, and substances that improve the performance of the active substance, such as synergists. Examples are insecticides, acaricides, nematicides, molluscicides, aligicides, virusicides, rodenticide, bactericides, fungicides, chemosterilants, anthelmintics. Examples of a biological active substance include baculovirus, plant extract, and bacteria.

The mixtures of the compounds of formula I with other active substances may also have further surprising advantages which can also be described, in a wider sense, as synergistic activity. For example, better tolerance by plants, reduced phytotoxicity, insects can be controlled in their different development stages, or better behaviour relating to production, for example grinding or mixing, storage or use.

Individual active substances can occur in more than one group or class, and at more than one place within a group or class: information about the active substances, their spectrum, sources and classifications can be found from Compendium of Pesticide Common Names (see http://www.alanwood.net/pesticides/index.html) or from the Pesticide Manual created by the British Crop Production Counci (see http://bcpcdata.com/pesticide-manual.html).

Preferred mixtures are indicated below where a compound of formula I according to the invention is indicated as "I".

Compositions comprising an adjuvant include I+compounds selected from the group of substances consisting of petroleum oils;

Compositions comprising an acaricide include I+1,1-bis (4-chlorophenyl)-2-ethoxyethanol, I+2,4-dichlorophenyl benzenesulfonate, I+2-fluoro-N-methyl-N-1-naphthylacetamide, I+4-chlorophenyl phenyl sulfone, I+abamectin, I+acequinocyl, I+acetoprole, I+acrinathrin, I+aldicarb, I+aldoxycarb, I+alpha-cyperrneihrin, I+amidithion, I+amidoflumet, I+amidothioate, I+amiton, I+amiton hydrogen oxalate, I+amitraz, I+aramite, I+arsenous oxide, I+AVI 382, I+AZ 60541, I+azinphos-ethyl, I+azinphos-methyl, I+azobenzene, I+azocyclotin, I+azothoate, I+benomyl, I+benoxafos, I+benzoximate, I+benzyl benzoate, I+bifenazate, I+bifenthrin, I+binapacryl, I+brofenvalerate, I+bromocyclen, I+bromophos, I+bromophos-ethyl, I+bromopropylate, I+buprofezin, I+butocarboxim, I+butoxycarboxim, I+butylpyridaben, I+calcium polysulfide, I+camphechlor, I+carbanolate, I+carbaryl, I+carbofuran, I+carbophenothion, I+CGA 50'439, I+chinomethionat, I+chlorbenside, I+chlordimeform, I+chlordimeform hydrochloride, I+chlorfenapyr, I+chlorfenethol, I+chlorfenson, I+chlorfensulfide, I+chlorfenvinphos, I+chlorobenzilate, I+chloromebuform, I+chloromethiuron, I+chloropropylate, I+chlorpyrifos, I+chlorpyrifos-methyl, I+chlorthiophos, I+cinerin I, I+cinerin II, I+cinerins, I+clofentezine, I+closantel, I+coumaphos, I+crotamiton, I+crotoxyphos, I+cufraneb, I+cyanthoate, I+cyflumetofen, I+cyhalothrin, I+cyhexatin, I+cypermethrin, I+DCPM, I+DDT, I+demephion, I+demephion-O, I+demephion-S, I+demeton, I+demeton-methyl, I+demeton-O, I+demeton-O-methyl, I+demeton-S, I+demeton-S-methyl, I+demeton-S-methylsulfon, I+diafenthiuron, I+dialifos, I+diazinon, I+dichlofluanid, I+dichlorvos, I+dicliphos, I+dicofol, I+dicrotophos, I+dienochlor, I+dimefox, I+dimethoate, I+dinactin, I+dinex, I+dinex-diclexine, I+dinobuton, I+dinocap, I+dinocap-4, I+dinocap-6, I+dinocton, I+dinopenton, I+dinosulfon, I+dinoterbon, I+dioxathion, I+diphenyl sulfone, I+disulfiram, I+disulfoton, I+DNOC, I+dofenapyn, I+doramectin, I+endosulfan, I+endothion, I+EPN, I+eprinomectin, I+ethion, I+ethoate-methyl, I+etoxazole, I+etrimfos, I+fenazaflor, I+fenazaquin, I+fenbutatin oxide, I+fenothiocarb, I+fenpropathrin, I+fenpyrad, I+fenpyroximate, I+fenson, I+fentrifanil, I+fenvalerate, I+fipronil, I+fluacrypyrim, I+fluazuron, I+flubenzimine, I+flucycloxuron, I+flucythrinate, I+fluenetil, I+flufenoxuron, I+flumethrin, I+fluorbenside, I+fluvalinate, I+FMC 1137, I+formetanate, I+formetanate hydrochloride, I+formothion, I+formparanate, I+gamma-HCH, I+glyodin, I+halfenprox, I+heptenophos, I+hexadecyl cyclopropanecarboxylate, I+hexythiazox, I+iodomethane, I+isocarbophos, I+isopropyl O-(methoxyaminothiophosphoryl)salicylate, I+ivermectin, I+jasmolin I, I+jasmolin II, I+jodfenphos, I+lindane, I+lufenuron, I+malathion, I+malonoben, I+mecarbam, I+mephosfolan, I+mesulfen, I+methacrifos, I+methamidophos, I+methidathion, I+methiocarb, I+methomyl, I+methyl bromide, I+metolcarb, I+mevinphos, I+mexacarbate, I+milbemectin, I+milbemycin oxime, I+mipafox, I+monocrotophos, I+morphothion, I+moxidectin, I+naled, I+NC-184, I+NC-512, I+nifluridide, I+nikkomycins, I+nitrilacarb, I+nitrilacarb 1:1 zinc chloride complex, I+NNI-0101, I+NNI-0250, I+ometohate, I+oxamyl, I+oxydeprofos, I+oxydisulfoton, I+pp'-DDT, I+parathion, I+permethrin, I+petroleum oils, I+phenkapton, I+phenthoate, I+phorate, I+phosalone, I+phosfolan, I+phosmet, I+phosphamidon, I+phoxim, I+pirimiphos-methyl, I+polychloroterpenes, I+polynactins, I+proclonol, I+profenofos, I+promacyl, I+propargite, I+propetamphos, I+propoxur, I+prothidathion, I+prothoate, I+pyrethrin I, I+pyrethrin II, I+pyrethrins, I+pyridaben, I+pyridaphenthion, I+pyrimidifen, I+pyrimitate, I+quinalphos, I+quintiofos, I+R-1492, I+RA-17, I+rotenone, I+schradan, I+sebufos, I+selamectin, I+SI-0009, I+sophamide, I+spirodiclofen, I+spiromesifen, I+SSI-121, I+sulfiram, I+sulfluramid, I+sulfotep, I+sulfur, I+SZI-121, I+tau-fluvalinate, I+tebufenpyrad, I+TEPP, I+terbam, I+tetrachlorvinphos, I+tetradifon, I+tetranactin, I+tetrasul, I+thiafenox, I+thiocarboxime, I+thiofanox, I+thiometon, I+thioquinox, I+thuringiensin, I+triamiphos, I+triarathene, I+triazophos, I+triazuron, I+trichlorfon, I+trifenofos, I+trinactin, I+vamidothion, I+vaniliprole and I+YI-5302;

Compositions comprising an anthelmintic include I+abamectin, I+crufomate, I+doramectin, I+emamectin, I+emamectin benzoate, I+eprinomectin, I+ivermectin, I+milbemycin oxime, I+moxidectin, I+piperazine, I+selamectin, I+spinosad and I+thiophanate;

Compositions comprising an avicide include I+chloralose, I+endrin, I+fenthion, I+pyridin-4-amine and I+strychnine;

Compositions comprising a biological control agent include I+*Adoxophyes orana* GV, I+*Agrobacterium radiobacter*, I+*Amblyseius* spp., I+*Anagrapha falcifera* NPV, I+*Anagrus atomus*, I+*Aphelinus abdominalis*, I+*Aphidius colemani*, I+*Aphidoletes aphidimyza*, I+*Autographa californica* NPV, I+*Bacillus firmus*, I+*Bacillus sphaericus* Neide, I+*Bacillus thuringiensis* Berliner, I+*Bacillus thuringiensis* subsp. *aizawai*, I+*Bacillus thuringiensis* subsp. *israelensis*, I+*Bacillus thuringiensis* subsp. *japonensis*, I+*Bacillus thuringiensis* subsp. *kurstaki*, I+*Bacillus thuringiensis* subsp. *tenebrionis*, I+*Beauveria bassiana*, I+*Beauveria brongniartii*, I+*Chlysoperla carnea*, I+*Cryptolaemus montrouzieri*, I+*Cydia pomonella* GV, I+*Dacnusa sibirica*, I+*Diglyphus isaea*, I+*Encarsia formosa*, I+*Eretmocerus eremicus*, I+*Helicoverpa zea* NPV, I+*Heterorhabditis bacteriophora* and *H. megidis*, I+*Hippodamia convergens*, I+*Leptomastix dactylopii*, I+*Macrolophus caliginosus*, I+*Mamestra brassicae* NPV, I+*Metaphycus helvolus*, I+*Metarhizium anisopliae* var. *acridum*, I+*Metarhizium anisopliae* var. *anisopliae*, I+*Neodiprion sertifer* NPV and *N. lecontei* NPV, I+*Orius* spp., I+*Paecilomyces fumosoroseus*, I+*Phytoseiulus persimilis*, I+*Spodoptera exigua* multicapsid nuclear polyhedrosis virus, I+*Steinernema bibionis*, I+*Steinernema carpocapsae*, I+*Steinernema feltiae*, I+*Steinernema glaseri*, I+*Steinernema riobrave*, I+*Steinernema riobravis*, I+*Steinernema scapterisci*, I+*Steinernema* spp., I+*Trichogramma* spp., I+*Typhlodromus occidentalis* and I+*Verticillium lecanii*;

Compositions comprising a soil sterilant include I+iodomethane and methyl bromide;

Compositions comprising a chemosterilant include I+apholate, I+bisazir, I+busulfan, I+diflubenzuron, I+dimatif, I+hemel, I+hempa, I+metepa, I+methiotepa, I+methyl apholate, I+morzid, I+penfluron, I+tepa, I+thiohempa, I+thiotepa, I+tretamine and I+uredepa;

Compositions comprising an insect pheromone include I+(E)-dec-5-en-1-yl acetate with (E)-dec-5-en-1-ol, I+(E)-tridec-4-en-1-yl acetate, I+(E)-6-methylhept-2-en-4-ol, I+(E,Z)-tetradeca-4,10-dien-1-yl acetate, I+(Z)-dodec-7-en-1-yl acetate, I+(Z)-hexadec-11-enal, I+(Z)-hexadec-11-en-1-yl acetate, I+(Z)-hexadec-13-en-11-yn-1-yl acetate, I+(Z)-icos-13-en-10-one, I+(Z)-tetradec-7-en-1-al, I+(Z)-tetradec-9-en-1-ol, I+(Z)-tetradec-9-en-1-yl acetate, I+(7E,9Z)-dodeca-7,9-dien-1-yl acetate, I+(9Z,11E)-tetradeca-9,11-dien-1-yl acetate, I+(9Z,12E)-tetradeca-9,12-dien-1-yl acetate, I+14-methyloctadec-1-ene, I+4-methylnonan-5-ol with 4-methylnonan-5-one, I+alpha-multistriatin, I+brevicomin, I+codlelure, I+codlemone, I+cuelure, I+disparlure, I+dodec-8-en-1-yl acetate, I+dodec-9-en-1-yl acetate, I+dodeca-8, I+10-dien-1-yl acetate, I+dominicalure, I+ethyl 4-methyloctanoate, I+eugenol, I+frontalin, I+gossyplure, I+grandlure, I+grandlure I, I+grandlure II, I+grandlure III, I+grandlure IV, I+hexalure, I+ipsdienol, I+ipsenol, I+japonilure, I+lineatin, I+litlure, I+looplure, I+medlure, I+megatomoic acid, I+methyl eugenol, I+muscalure, I+octadeca-2, 13-dien-1-yl acetate, I+octadeca-3,13-dien-1-yl acetate, I+orfralure, I+oryctalure, I+ostramone, I+siglure, I+sordidin, I+sulcatol, I+tetradec-11-en-1-yl acetate, I+trimedlure, I+trimedlure A, I+trimedlure $B_1$, I+trimedlure $B_2$, I+trimedlure C and I+trunc-call;

Compositions comprising an insect repellent include I+2-(octylthio)ethanol, I+butopyronoxyl, I+butoxy(polypropylene glycol), I+dibutyl adipate, I+dibutyl phthalate, I+dibutyl succinate, I+diethyltoluamide, I+dimethyl carbate, I+dimethyl phthalate, I+ethyl hexanediol, I+hexamide, I+methoquin-butyl, I+methylneodecanamide, I+oxamate and I+picaridin;

Compositions comprising an insecticide include I+1-dichloro-1-nitroethane, I+1,1-dichloro-2,2-bis(4-ethylphenyl) ethane, I+, I+1,2-dichloropropane, I+1,2-dichloropropane with 1,3-dichloropropene, I+1-bromo-2-chloroethane, I+2, 2,2-trichloro-1-(3,4-dichlorophenyl)ethyl acetate, I+2,2-dichlorovinyl 2-ethylsulfinylethyl methyl phosphate, I+2-(1, 3-dithiolan-2-yl)phenyl dimethylcarbamate, I+2-(2-butoxyethoxy)ethyl thiocyanate, I+2-(4,5-dimethyl-1,3-dioxolan-2-yl)phenyl methylcarbamate, I+2-(4-chloro-3,5-xylyloxy)ethanol, I+2-chlorovinyl diethyl phosphate, I+2-imidazolidone, I+2-isovalerylindan-1,3-dione, I+2-methyl (prop-2-ynyl)aminophenyl methylcarbamate, I+2-thiocyanatoethyl laurate, I+3-bromo-1-chloroprop-1-ene, I+3-methyl-1-phenylpyrazol-5-yldimethylcarbamate, I+4-methyl(prop-2-ynyl)amino-3,5-xylylmethylcarbamate, I+5, 5-dimethyl-3-oxocyclohex-1-enyl dimethylcarbamate, I+abamectin, I+acephate, I+acetamiprid, I+acethion, I+acetoprole, I+acrinathrin, I+acrylonitrile, I+alanycarb, I+aldicarb, I+aldoxycarb, I+aldrin, I+allethrin, I+allosamidin, I+allyxycarb, I+alpha-cypermethrin, I+alpha-ecdysone, I+aluminium phosphide, I+amidithion, I+amidothioate, I+aminocarb, I+amiton, I+amiton hydrogen oxalate, I+amitraz, I+anabasine, I+athidathion, I+AVI 382, I+AZ 60541, I+azadirachtin, I+azamethiphos, I+azinphos-ethyl, I+azinphos-methyl, I+azothoate, I+*Bacillus thuringiensis* delta endotoxins, I+barium hexafluorosilicate, I+barium polysulfide, I+barthrin, I+Bayer 22/190, I+Bayer 22408, I+bendiocarb, I+benfuracarb, I+bensultap, I+beta-cyfluthrin, I+beta-cypermethrin, I+bifenthrin, I+bioallethrin, I+bioallethrin S-cyclopentenyl isomer, I+bioethanomethrin, I+biopermethrin, I+bioresmethrin, I+bis(2-chloroethyl) ether, I+bistrifluron, I+borax, I+brofenvalerate, I+bromfenvinfos, I+bromocyclen, I+bromo-DDT, I+bromophos, I+bromophos-ethyl, I+bufencarb, I+buprofezin, I+butacarb, I+butathiofos, I+butocarboxim, I+butonate, I+butoxycarboxim, I+butylpyridaben, I+cadusafos, I+calcium arsenate, I+calcium cyanide, I+calcium polysulfide, I+camphechlor, I+carbanolate, I+carbaryl, I+carbofuran, I+carbon disulfide, I+carbon tetrachloride, I+carbophenolhion, I+carbosulfan, I+cartap, I+cartap hydrochloride, I+cevadine, I+chlorbicyclen, I+chlordane, I+chlordecone, I+chlordimeform, I+chlordimeform hydrochloride, I+chlorethoxyfos, I+chlorfenapyr, I+chlorfenvinphos, I+chlorfluazuron, I+chlormephos, I+chloroform, I+chloropicrin, I+chlorphoxim, I+chlorprazophos, I+chlorpyrifos, I+chlorpyrifos-methyl, I+chlorthiophos, I+chromafenozide, I+cinerin I,I+cinerin II, I+cinerins, I+cis-resmethrin, I+cismethrin, I+clocythrin, I+cloethocarb, I+closantel, I+clothianidin, I+copper acetoarsenite, I+copper arsenate, I+copper oleate, I+coumaphos, I+coumithoate, I+crotamiton, I+crotoxyphos, I+crufomate, I+cryolite, I+CS 708, I+cyanofenphos, I+cyanophos, I+cyanthoate, I+cyclethrin, I+cycloprothrin, I+cyfluthrin, I+cyhalothrin, I+cypermethrin, I+cyphenothrin, I+cyromazine, I+cythioate, I+d-limonene, I+d-tetramethrin, I+DAEP, I+dazomet, I+DDT, I+decarbofuran, I+deltamethrin, I+demephion, I+demephion-O, I+demephion-S, I+demeton, I+demeton-methyl, I+demeton-O, I+demeton-O-methyl, I+demeton-S, I+demeton-S-methyl, I+demeton-S-methylsulphon, I+diafenthiuron, I+dialifos, I+diamidafos, I+diazinon, I+dicapthon, I+dichlofenthion, I+dichlorvos, I+dicliphos, I+dicresyl, I+dicrotophos, I+dicyclanil, I+dieldrin, I+diethyl 5-methylpyrazol-3-yl phosphate, I+diflubenzuron, I+dilor, I+dimefluthrin, I+dimefox, I+dimetan, I+dimethoate, I+dimethrin, I+dimethylvinphos, I+dimetilan, I+dinex, I+dinex-diclexine, I+dinoprop, I+dinosam, I+dinoseb, I+dinotefuran, I+diofenolan, I+dioxabenzofos, I+dioxacarb, I+dioxathion, I+disulfoton, I+dithicrofos, I+DNOC, I+doramectin, I+DSP, I+ecdysterone, I+EI 1642, I+emamectin, I+emamectin benzoate, I+EMPC, I+empenthrin, I+endosulfan, I+endothion, I+endrin, I+EPBP, I+EPN, I+epofenonane, I+eprinomectin, I+esfenvalerate, I+etaphos, I+ethiofencarb, I+ethion, I+ethiprole, I+ethoate-methyl, I+ethoprophos, I+ethyl formate, I+ethyl-DDD, I+ethylene dibromide, I+ethylene dichloride, I+ethylene oxide, I+etofenprox, I+etrimfos, I+EXD, I+famphur, I+fenamiphos, I+fenazaflor, I+fenchlorphos, I+fenethacarb, I+fenfluthrin, I+fenitrothion, I+fenobucarb, I+fenoxacrim, I+fenoxycarb, I+fenpirithrin, I+fenpropathrin, I+fenpyrad, I+fensulfothion, I+fenthion, I+fenthion-ethyl, I+fenvalerate, I+fipronil, I+flonicamid, I+flubendiamide, I+flucofuron, I+flucycloxuron, I+flucythrinate, I+fluenetil, I+flufenerim, I+flufenoxuron, I+flufenprox, I+flumethrin, I+fluvalinate, I+FMC 1137, I+fonofos, I+formetanate, I+formetanate hydrochloride, I+formothion, I+formparanate, I+fosmethilan, I+fospirate, I+fosthiazate, I+fosthietan, I+furathiocarb, I+furethrin, I+gamma-cyhalothrin, I+gamma-HCH, I+guazatine, I+guazatine acetates, I+GY-81, I+halfenprox, I+halofenozide, I+HCH, I+HEOD, I+heptachlor, I+heptenophos, I+heterophos, I+hexaflumuron, I+HHDN, I+hydramethylnon, I+hydrogen cyanide, I+hydroprene, I+hyquincarb, I+imidacloprid, I+imiprothrin, I+indoxacarb, I+iodomethane, I+IPSP, I+isazofos, I+isobenzan, I+isocarbophos, I+isodrin, I+isofenphos, I+isolane, I+isoprocarb, I+isopropyl O-(methoxy-aminothiophosphoryl)salicylate, I+isoprothiolane, I+isothioate, I+isoxathion, I+ivermectin, I+jasmolin I, I+jasmolin II, I+jodfenphos, I+juvenile hormone I, I+juvenile hormone II, I+juvenile hormone III, I+kelevan, I+kinoprene, I+lambda-cyhalothrin, I+lead arsenate, I+lepimectin, I+leptophos, I+lindane, I+lirimfos, I+lufenuron, I+lythidathion, I+m-cumenyl methylcarbamate, I+magnesium phosphide, I+malathion, I+malonoben, I+mazidox, I+mecarbam, I+mecarphon, I+menazon, I+mephosfolan, I+mercurous chloride, I+mesulfenfos, I+metaflumizone, I+metam, I+metam-potassium, I+metam-sodium, I+methacrifos, I+methamidophos, I+methanesulfonyl fluoride, I+methidathion, I+methiocarb, I+methocrotophos, I+methomyl, I+methoprene, I+methoquin-butyl, I+methothrin, I+methoxychlor, I+methoxyfenozide, I+methyl bromide, I+methyl isothiocyanate, I+methylchloroform, I+methylene chloride, I+metofluthrin, I+metolcarb, I+metoxadiazone, I+mevinphos, I+mexacarbate, I+milbemectin, I+milbemycin oxime, I+mipafox, I+mirex, I+monocrotophos, I+morphothion, I+moxidectin, I+naftalofos, I+naled, I+naphthalene, I+NC-170, I+NC-184, I+nicotine, I+nicotine sulfate, I+nifluridide, I+nitenpyram, I+nithiazine, I+nitrilacarb, I+nitrilacarb 1:1 zinc chloride complex, I+NNI-0101, I+NNI-0250, I+nornicotine, I+novaluron, I+noviflumuron, I+O-5-dichloro-4-iodophenyl O-ethyl ethylphosphonothioate, I+O,O-diethyl O-4-methyl-2-oxo-2H-chromen-7-yl phosphorothioate, I+O,O-diethyl O-6-methyl-2-propylpyrimidin-4-yl phosphorothioate, I+O,O,O',O'-tetrapropyl dithiopyrophosphate, I+oleic acid, I+omethoate, I+oxamyl, I+oxydemeton-methyl, I+oxydeprofos, I+oxydisulfoton, I+pp'-DDT, I+para-dichlorobenzene, I+parathion, I+parathion-methyl, I+penfluron, I+pentachlorophenol, I+pentachlorophenyl laurate, I+permethrin, I+petroleum oils, I+PH 60-38, I+phenkapton, I+phenothrin, I+phenthoate, I+phorate+TX, I+phosalone, I+phosfolan, I+phosmet, I+phosnichlor, I+phosphamidon, I+phosphine, I+phoxim, I+phoxim-methyl, I+pirimetaphos, I+pirimicarb, I+pirimiphos-ethyl, I+pirimiphos-methyl, I+polychlorodicyclopentadiene isomers, I+polychloroterpenes, I+potassium arsenite, I+potassium thiocyanate, I+prallethrin, I+precocene I, I+precocene II, I+precocene III, I+primidophos, I+profenofos, I+profluthrin, I+promacyl, I+promecarb, I+propaphos, I+propetamphos, I+propoxur, I+prothidathion, I+prothiofos, I+prothoate, I+protrifenbute, I+pymetrozine, I+pyraclofos, I+pyrazophos, I+pyresmethrin, I+pyrethrin I, I+pyrethrin II, I+pyrethrins, I+pyridaben, I+pyridalyl, I+pyridaphenthion, I+pyrimidifen, I+pyrimitate, I+pyriproxyfen, I+quassia, I+quinalphos, I+quinalphos-methyl, I+quinothion, I+quintiofos, I+R-1492, I+rafoxanide, I+resmethrin, I+rotenone, I+RU 15525, I+RU 25475, I+ryania, I+ryanodine, I+sabadilla, I+schradan, I+sebufos, I+selamectin, I+SI-0009, I+SI-0205, I+SI-0404, I+SI-0405, I+silafluofen, I+SN 72129, I+sodium arsenite, I+sodium cyanide, I+sodium fluoride, I+sodium hexafluorosilicate, I+sodium pentachlorophenoxide, I+sodium selenate, I+sodium thiocyanate, I+sophamide, I+spinosad, I+spiromesifen, I+spirotetrmat, I+sulcofuron, I+sulcofuron-sodium, I+sulfluramid, I+sulfotep, I+sulfuryl fluoride, I+sulprofos, I+tar oils, I+tau-fluvalinate, I+tazimcarb, I+TDE, I+tebufenozide, I+tebufenpyrad, I+tebupirimfos, I+teflubenzuron, I+tefluthrin, I+temephos, I+TEPP, I+terallethrin, I+terbam, I+terbufos, I+tetrachloroethane, I+tetrachlorvinphos, I+tetramethrin, I+theta-cypermethrin, I+thiacloprid, I+thiafenox, I+thiamethoxam, I+thicrofos, I+thiocarboxime, I+thiocyclam, I+thiocyclam hydrogen oxalate, I+thiodicarb, I+thiofanox, I+thiometon, I+thionazin, I+thiosultap, I+thiosultap-sodium, I+thuringiensin, I+tolfenpyrad, I+tralomethrin, I+transfluthrin, I+transpermethrin, I+triamiphos, I+triazamate, I+triazophos, I+triazuron, I+trichlorfon, I+trichlormetaphos-3, I+trichloronat, I+trifenofos, I+triflumuron, I+trimethacarb, I+triprene, I+vamidothion, I+vaniliprole, I+veratridine, I+veratrine, I+XMC, I+xylylcarb, I+YI-5302, I+zeta-cypermethrin, I+zetamethrin, I+zinc phosphide, I+zolaprofos and ZXI 8901, I+cyantraniliprole, I+chlorantraniliprole, I+cyenopyrafen, I+cyflumetofen, I+pyrifluquinazon, I+spinetoram, I+spirotetramat, I+sulfoxaflor, I+flufiprole, I+meperfluthrin, I+tetramethylfluthrin, I+triflumezopyrim;

Compositions comprising a molluscicide include I+bis(tributyltin) oxide, I+bromoacetamide, I+calcium arsenate, I+cloethocarb, I+copper acetoarsenite, I+copper sulfate, I+fentin, I+ferric phosphate, I+metaldehyde, I+methiocarb, I+niclosamide, I+niclosamide-olamine, I+pentachlorophenol, I+sodium pentachlorophenoxide, I+tazimcarb, I+thiodicarb, I+tributyltin oxide, I+trifenmorph, I+trimethacarb, I+triphenyltin acetate and triphenyltin hydroxide, I+pyriprole;

Compositions comprising a nematicide include I+AKD-3088, I+1,2-dibromo-3-chloropropane, I+1,2-dichloropropane, I+1,2-dichloropropane with 1,3-dichloropropene, I+1,3-dichloropropene, I+3,4-dichlorotetrahydrothiophene 1,1-dioxide, I+3-(4-chlorophenyl)-5-methylrhodanine, I+5-methyl-6-thioxo-1,3,5-thiadiazinan-3-ylacetic acid, I+6-isopentenylaminopurine, I+abamectin, I+acetoprole, I+alanycarb, I+aldicarb, I+aldoxycarb, I+AZ 60541, I+benclothiaz, I+benomyl, I+butylpyridaben, I+cadusafos, I+carbofuran, I+carbon disulfide, I+carbosulfan, I+chloropicrin, I+chlorpyrifos, I+cloethocarb, I+cytokinins, I+dazomet, I+DBCP, I+DCIP, I+diamidafos, I+dichlofenthion, I+dicliphos, I+dimethoate, I+doramectin, I+emamectin, I+emamectin benzoate, I+eprinomectin, I+ethoprophos, I+ethylene dibromide, I+fenamiphos, I+fenpyrad, I+fensulfothion, I+fosthiazate, I+fosthietan, I+furfural, I+GY-81, I+heterophos, I+iodomethane, I+isamidofos, I+isazofos, I+ivermectin, I+kinetin, I+mecarphon, I+metam, I+metam-potassium, I+metam-sodium, I+methyl bromide, I+methyl isothiocyanate, I+milbemycin oxime, I+moxidectin, I+*Myrothecium verrucaria* composition, I+NC-184, I+oxamyl, I+phorate, I+phosphamidon, I+phosphocarb, I+sebufos, I+selamectin, I+spinosad, I+terbam, I+terbufos, I+tetrachlorothiophene, I+thiafenox, I+thionazin, I+triazophos, I+triazuron, I+xylenols, I+YI-5302 and zeatin, I+fluensulfone;

Compositions comprising a synergist include I+2-(2-butoxyethoxy)ethyl piperonylate, I+(5-(1,3-benzodioxol-5-yl)-3-hexylcyclohex-2-enone, I+farnesol with nerolidol, I+MB-599, I+MGK 264, I+piperonyl butoxide, I+piprotal, I+propyl isomer, I+S421, I+sesamex, I+sesasmolin and I+sulfoxide;

Compositions comprising an animal repellent include I+anthraquinone, I+chloralose, I+copper naphthenate, I+copper oxychloride, I+diazinon, I+dicyclopentadiene, I+guazatine, I+guazatine acetates, I+methiocarb, I+pyridin-4-amine, I+thiram, I+trimethacarb, I+zinc naphthenate and I+ziram;

Further compositions include I+Brofluthrinate, I+Cycloxaprid, I+Diflovidazine, I+Flometoquin, I+Fluhexafon, I+Guadipyr, I+*Plutella xylostella* Granulosis virus, I+*Cydia pomonella* Granulosis virus, I+Harpin, I+Imicyafos, I+*Heliothis virescens* Nucleopolyhedrovirus, I+*Heliothis punctigera* Nucleopolyhedrovirus, I+*Helicoverpa armigera* Nucleopolyhedrovirus, I+*Helicoverpa zea* Nucleopolyhedrovirus, I+*Spodoptera frugiperda* Nucleopolyhedrovirus, I+*Plutella xylostella* Nucleopolyhedrovirus, I+*Pasteuria nishizawae*, I+p-cymene, I+Pyflubumide, I+Pyrafluprole, I+pyrethrum, I+QRD 420, I+QRD 452, I+QRD 460, I+Terpenoid blends, I+Terpenoids, I+Tetraniliprole, and I+α-terpinene;

Composition also include mixtures of compound of formula I and an active substance referenced by a code, such as I+code AE 1887196 (BSC-BX60309), I+code NNI-0745 GR, I+code IKI-3106, I+code JT-L001, I+code ZNQ-08056, I+code IPPA152201, I+code HNPC-A9908 (CAS: [660411-21-2]), I+code HNPC-A2005 (CAS: [860028-12-2]), I+code JS118, I+code ZJ0967, I+code ZJ2242, I+code JS7119 (CAS: [929545-74-4]), I+code SN-1172, I+code HNPC-A9835, I+code HNPC-A9955, I+code HNPC-A3061, I+code Chuanhua 89-1, I+code IPP-10, I+code ZJ3265, I+code JS9117, I+code SYP-9080, I+code ZJ3757, I+code ZJ4042, I+code ZJ4014, I+code ITM-121, I+code DPX-RAB55 (DKI-2301), I+code Me5382, I+code NC-515, I+code NA-89, I+code MIE-1209, I+code MCI-8007, I+code BCS-CL73507, I+code S-1871, I+code DPX-RDS63, and I+code AKD-1193.

The active ingredient mixture of the compounds of formula I selected from Tables 1 to 13 with active ingredients described above comprises a compound selected from Tables 1 to 13 and an active ingredient as described above preferably in a mixing ratio of from 100:1 to 1:6000, especially from 50:1 to 1:50, more especially in a ratio of from 20:1 to 1:20, even more especially from 10:1 to 1:10, very especially from 5:1 and 1:5, special preference being given to a ratio of from 2:1 to 1:2, and a ratio of from 4:1 to 2:1 being likewise preferred, above all in a ratio of 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are by weight.

The mixtures as described above can be used in a method for controlling pests, which comprises applying a composition comprising a mixture as described above to the pests or their environment, with the exception of a method for treatment of the human or animal body by surgery or therapy and diagnostic methods practised on the human or animal body.

The mixtures comprising a compound of formula I selected from Tables 1 to 13 and one or more active ingredients as described above can be applied, for example, in a single "ready-mix" form, in a combined spray mixture composed from separate formulations of the single active ingredient components, such as a "tank-mix", and in a combined use of the single active ingredients when applied in a sequential manner, i.e. one after the other with a reasonably short period, such as a few hours or days. The order of applying the compounds of formula I selected from Tables 1 to 13 and the active ingredients as described above is not essential for working the present invention.

The compositions according to the invention can also comprise further solid or liquid auxiliaries, such as stabilizers, for example unepoxidized or epoxidized vegetable oils (for example epoxidized coconut oil, rapeseed oil or soya oil), antifoams, for example silicone oil, preservatives, viscosity regulators, binders and/or tackifiers, fertilizers or other active ingredients for achieving specific effects, for example bactericides, fungicides, nematocides, plant activators, molluscicides or herbicides.

The compositions according to the invention are prepared in a manner known per se, in the absence of auxiliaries for example by grinding, screening and/or compressing a solid active ingredient and in the presence of at least one auxiliary for example by intimately mixing and/or grinding the active ingredient with the auxiliary (auxiliaries). These processes for the preparation of the compositions and the use of the compounds I for the preparation of these compositions are also a subject of the invention.

The application methods for the compositions, that is the methods of controlling pests of the abovementioned type, such as spraying, atomizing, dusting, brushing on, dressing, scattering or pouring—which are to be selected to suit the intended aims of the prevailing circumstances—and the use of the compositions for controlling pests of the abovementioned type are other subjects of the invention. Typical rates of concentration are between 0.1 and 1000 ppm, preferably between 0.1 and 500 ppm, of active ingredient. The rate of application per hectare is generally 1 to 2000 g of active ingredient per hectare, in particular 10 to 1000 g/ha, preferably 10 to 600 g/ha.

A preferred method of application in the field of crop protection is application to the foliage of the plants (foliar application), it being possible to select frequency and rate of application to match the danger of infestation with the pest in question. Alternatively, the active ingredient can reach the plants via the root system (systemic action), by drenching the locus of the plants with a liquid composition or by incorporating the active ingredient in solid form into the locus of the plants, for example into the soil, for example in the form of granules (soil application). In the case of paddy rice crops, such granules can be metered into the flooded paddy-field.

The compounds of the invention and compositions thereof are also be suitable for the protection of plant propagation material, for example seeds, such as fruit, tubers or kernels, or nursery plants, against pests of the abovementioned type. The propagation material can be treated with the compound prior to planting, for example seed can be treated prior to sowing. Alternatively, the compound can be applied to seed kernels (coating), either by soaking the kernels in a liquid composition or by applying a layer of a solid composition. It is also possible to apply the compositions when the propagation material is planted to the site of application, for example into the seed furrow during drilling. These treatment methods for plant propagation material and the plant propagation material thus treated are further subjects of the invention. Typical treatment rates would depend on the plant and pest/fungi to be controlled and are generally between 1 to 200 grams per 100 kg of seeds, preferably between 5 to 150 grams per 100 kg of seeds, such as between 10 to 100 grams per 100 kg of seeds.

The invention therefore relates to a method for the protection of plant propagation material from the attack by pests, which comprises treating the propagation material or the site, where the propagation material is planted, with a compound of formula (I) or with a composition as defined above, which comprises at least one compound of formula I or, where appropriate, a tautomer thereof, in each case in free form or in agrochemically utilizable salt form, as active ingredient and at least one auxiliary composition.

The term seed embraces seeds and plant propagules of all kinds including but not limited to true seeds, seed pieces, suckers, corns, bulbs, fruit, tubers, grains, rhizomes, cuttings, cut shoots and the like and means in a preferred embodiment true seeds.

The present invention also comprises seeds coated or treated with or containing a compound of formula I. The term "coated or treated with and/or containing" generally signifies that the active ingredient is for the most part on the surface of the seed at the time of application, although a greater or lesser part of the ingredient may penetrate into the seed material, depending on the method of application. When the said seed product is (re)planted, it may absorb the active ingredient. In an embodiment, the present invention makes available a plant propagation material adhered thereto with a compound of formula (I). Further, it is hereby made available, a composition comprising a plant propagation material treated with a compound of formula (I).

Seed treatment comprises all suitable seed treatment techniques known in the art, such as seed dressing, seed coating, seed dusting, seed soaking and seed pelleting. The seed treatment application of the compound formula (I) can be carried out by any known methods, such as spraying or by dusting the seeds before sowing or during the sowing/planting of the seeds.

BIOLOGICAL EXAMPLES

%=Percent by Weight, Unless Otherwise Specified

Example B1: *Spodoptera littoralis* (Egyptian Cotton Leaf Worm)

Cotton leaf discs were placed on agar in 24-well microtiter plates and sprayed with aqueous test solutions prepared from 10,000 ppm DMSO stock solutions. After drying, the leaf discs were infested with five L1 larvae. The samples were assessed for mortality, anti-feedant effect, and growth inhibition in comparison to untreated samples 3 days after infestation. Control of *Spodoptera littoralis* by a test sample is when at least one of mortality, anti-feedant effect, and growth inhibition is higher than the untreated sample.

The following compounds resulted in at least 80% control at an application rate of 200 ppm: P1, P2, P3, P17, P18, P19, P21, P27, P29, P31, P32, P33, P34, P35 and P36.

Example B2: *Plutella xylostella* (Diamond Back Moth)

24-well microtiter plates with artificial diet were treated with aqueous test solutions prepared from 10,000 ppm DMSO stock solutions by pipetting. After drying, the plates were infested with L2 larvae (10 to 15 per well). The samples were assessed for mortality and growth inhibition in comparison to untreated samples 5 days after infestation.

The following compounds gave an effect of at least 80% in at least one of the two categories (mortality or growth inhibition) at an application rate of 200 ppm: P1, P2, P3, P4, P12, P13, P14, P15, P17, P18, P19, P22, P29, P30, P31, P32, P33, P34, P35 and P36.

Example B3: *Diabrotica balteata* (Corn Root Worm)

Maize sprouts, placed on an agar layer in 24-well microtiter plates were treated with aqueous test solutions prepared from 10,000 ppm DMSO stock solutions by spraying. After drying, the plates were infested with L2 larvae (6 to 10 per well). The samples were assessed for mortality and growth inhibition in comparison to untreated samples 4 days after infestation.

The following compounds gave an effect of at least 80% in at least one of the two categories (mortality or growth inhibition) at an application rate of 200 ppm: P1, P2, P3, P13, P14, P15, P17, P21, P29, P35 and P36.

The invention claimed is:

1. A compound of formula I,

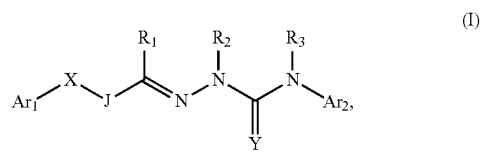

wherein,

Ar$_1$ is phenyl or phenyl substituted by one to three substituents independently selected from the group consisting of C$_1$-C$_4$alkyl, C$_2$-C$_4$alkenyl, C$_2$-C$_4$alkynyl, C$_3$-C$_6$cycloalkyl, C$_1$-C$_4$haloalkyl, C$_3$-C$_6$halocycloalkyl, C$_1$-C$_3$haloalkyl-C$_3$-C$_6$cycloalkyl, C$_3$-C$_6$cycloalkoxy, halogen, cyano, nitro, C$_1$-C$_4$alkoxy, C$_1$-C$_4$haloalkoxy, C$_1$-C$_4$alkylthio, C$_1$-C$_4$alkylsulfinyl, C$_1$-C$_4$alkylsulfonyl, C$_1$-C$_4$alkylsulfoximino, C$_2$-C$_4$alkylcarbonyl, CHO, C$_2$-C$_6$alkoxycarbonyl, or C$_2$-C$_6$haloalkoxycarbonyl;

Ar$_2$ is phenyl or phenyl substituted by one to three substituents independently selected from the group consisting of C$_1$-C$_4$alkyl, C$_2$-C$_4$alkenyl, C$_2$-C$_4$alkynyl, C$_3$-C$_6$cycloalkyl, C$_1$-C$_4$haloalkyl, C$_3$-C$_6$halocycloalkyl, C$_1$-C$_3$haloalkyl-C$_3$-

C$_6$cycloalkyl, C$_3$-C$_6$cycloalkoxy, halogen, cyano, nitro, C$_1$-C$_4$alkoxy, C$_1$-C$_4$haloalkoxy, C$_1$-C$_4$alkylthio, C$_1$-C$_4$alkylsulfinyl, C$_1$-C$_4$alkylsulfonyl, C$_1$-C$_4$alkylsulfoximino, C$_2$-C$_4$alkylcarbonyl, CHO, C$_2$-C$_6$alkoxycarbonyl, or C$_2$-C$_6$haloalkoxycarbonyl;

X is a direct bond, O, S, SO$_2$, CR$_4$R$_5$ or NR$_6$;

Y is oxygen or sulfur;

R$_1$ is hydrogen, C$_1$-C$_6$-alkyl, halo-C$_1$-C$_6$-alkyl, C$_3$-C$_6$-cycloalkyl or C$_1$-C$_3$-alkoxy;

R$_2$ and R$_3$ are independently from each other hydrogen, C$_1$-C$_6$-alkyl, C$_1$-C$_6$-haloalkyl, C$_3$-C$_6$-cycloalkyl, halo-C$_3$-C$_6$-cycloalkyl, C$_2$-C$_6$-alkenyl, C$_2$-C$_6$haloalkenyl, C$_2$-C$_6$-alkynyl, C$_2$-C$_6$haloalkynyl, C$_1$-C$_4$alkoxy-C$_1$-C$_4$alkyl, C$_1$-C$_4$haloalkylsulfinyl, C$_1$-C$_4$haloalkylsulfonyl, C$_1$-C$_4$alkylsulfinyl, C$_1$-C$_4$alkylsulfonyl, C$_2$-C$_4$alkylcarbonyl, C$_2$-C$_6$alkoxycarbonyl, C$_2$-C$_6$alkylaminocarbonyl, C$_3$-C$_6$dialkylaminocarbonyl, C$_2$-C$_6$alkoxycarbonyloxy, C$_2$-C$_6$alkylaminocarbonyloxy, C$_3$-C$_6$dialkylaminocarbonyloxy, or C$_1$-C$_4$alkoxyimino-C$_1$-C$_4$alkyl; provided that when R$_2$ and R$_3$ are different from hydrogen, R$_2$ and R$_3$ can be substituted by one to three substituents independently selected from the group consisting of C$_1$-C$_4$alkyl, C$_2$-C$_4$alkenyl, C$_2$-C$_4$alkynyl, C$_3$-C$_6$cycloalkyl, C$_1$-C$_4$haloalkyl, C$_2$-C$_4$haloalkenyl, C$_2$-C$_4$haloalkynyl, C$_3$-C$_6$halocycloalkyl, halogen, cyano, nitro, C$_1$-C$_4$alkoxy, C$_1$-C$_4$haloalkoxy, C$_1$-C$_4$alkylthio, C$_1$-C$_4$alkylsulfinyl, C$_1$-C$_4$alkylsulfonyl, C$_1$-C$_4$alkylsulfoximino, C$_1$-C$_4$alkylamino, C$_2$-C$_6$dialkylamino, C$_3$-C$_6$cycloalkylamino, C$_1$-C$_4$alkyl-C$_3$-C$_6$cycloalkylamino, C$_2$-C$_4$alkylcarbonyl, C$_2$-C$_6$alkoxycarbonyl, C$_2$-C$_6$alkylaminocarbonyl, and C$_2$-C$_8$ dialkylaminocarbonyl;

R$_4$, R$_5$ and R$_6$ are independently from each other hydrogen, C$_1$-C$_6$-alkyl, halo-C$_1$-C$_6$-alkyl, C$_3$-C$_6$-cycloalkyl or C$_1$-C$_3$-alkoxy;

J is a group selected from:

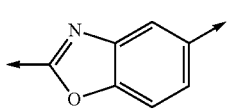
J$_1$'

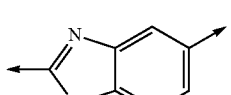
J$_2$'

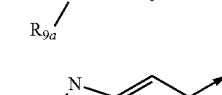
J$_3$'

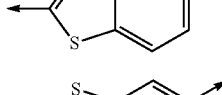
J4

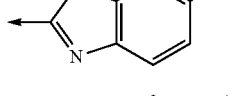
J5

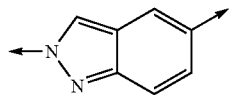
J6

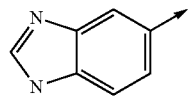
J7

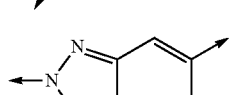
J8

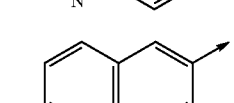
J9

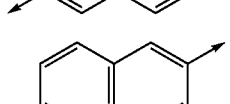
J10

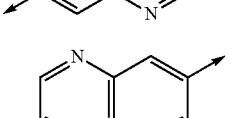
J11

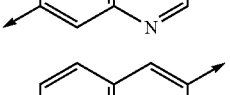
J12

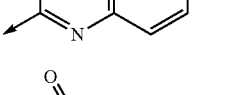
J13

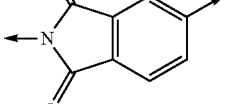
J14

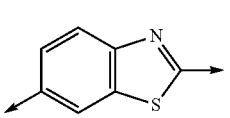
J15  or

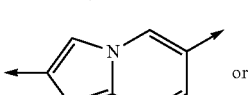
J16
;

R$_{9a}$ and R$_{7a}$ are independently selected from hydrogen, halogen, nitro, cyano, hydroxy, =O, CHO, C$_1$-C$_6$alkyl, C$_2$-C$_6$alkenyl, C$_2$-C$_6$alkynyl, C$_3$-C$_6$cycloalkyl, C$_1$-C$_6$haloalkyl, C$_2$-C$_6$haloalkenyl, C$_2$-C$_6$haloalkynyl, C$_3$-C$_6$halocycloalkyl, C$_1$-C$_4$alkoxy, C$_1$-C$_4$alkoxy-C$_1$-C$_4$alkoxy-C$_1$-C$_4$alkyl, C$_1$-C$_4$haloalkoxy, C$_1$-C$_4$alkylthio, C$_1$-C$_4$haloalkylthio, C$_1$-C$_4$haloalkylsulfinyl, C$_1$-C$_4$haloalkylsulfonyl, C$_1$-C$_4$alkylsulfinyl, C$_1$-C$_4$alkylsulfonyl, C$_1$-C$_4$alkylsulfonyl-C$_1$-C$_4$alkyl, C$_1$-C$_4$alkylsulfoximino-C$_1$-C$_4$alkyl, C$_1$-C$_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, $C_1$-$C_4$alkoxyimino-$C_1$-$C_4$alkyl-CONHSO$_2$—$C_1$-$C_6$-alkyl, —CONHSO$_2$N($C_1$-$C_6$-alkyl)$_2$, or $C_3$-$C_6$trialkylsilyl; or an agrochemically acceptable salt, stereoisomer, and N-oxide of the compounds of formula I.

2. The compound of claim 1, wherein:
Ar$_1$ is phenyl or phenyl substituted by one to three substituents independently selected from the group consisting of $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_3$-$C_6$halocycloalkyl, $C_1$-$C_3$haloalkyl-$C_3$-$C_6$cycloalkyl, $C_3$-$C_6$cycloalkoxy, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_2$-$C_4$alkylcarbonyl, CHO, $C_2$-$C_6$alkoxycarbonyl, or $C_2$-$C_6$haloalkoxycarbonyl;
Ar$_2$ is phenyl or phenyl substituted by one to three substituents independently selected from the group consisting of $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_3$-$C_6$halocycloalkyl, $C_1$-$C_3$haloalkyl-$C_3$-$C_6$cycloalkyl, $C_3$-$C_6$cycloalkoxy, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_2$-$C_4$alkylcarbonyl, CHO, $C_2$-$C_6$alkoxycarbonyl, or $C_2$-$C_6$haloalkoxycarbonyl;
X is a direct bond, O, S, SO$_2$, CR$_4$R$_5$, or NR$_6$;
Y is oxygen or sulfur;
R$_1$ is hydrogen, or $C_1$-$C_6$-alkyl, R$_2$ and R$_3$ are independently from each other hydrogen, $C_1$-$C_6$-alkyl, $C_1$-$C_6$-haloalkyl, $C_3$-$C_6$-cycloalkyl, halo-$C_3$-$C_6$-cycloalkyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, provided that when R$_2$ and R$_3$ groups are different from hydrogen, said R$_2$ and R$_3$ groups can be substituted by one to three substituents independently selected from the group consisting of $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_3$-$C_6$halocycloalkyl, halogen, cyano, nitro, $C_1$-$C_4$alkoxy, $C_1$-$C_4$haloalkoxy, and $C_1$-$C_4$alkylthio;
R$_4$, R$_5$ and R$_6$ are independently from each other hydrogen or $C_1$-$C_6$-alkyl;
J is a group selected from:

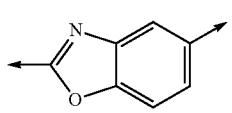

J$_1$'

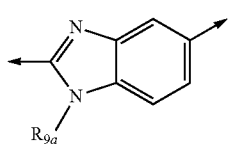

J$_2$'

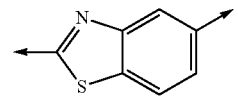

J$_3$'

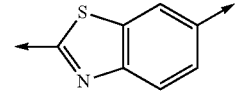

J4

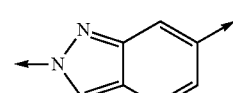

J5

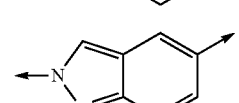

J6

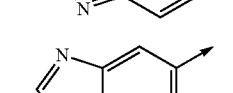

J7

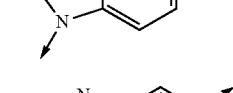

J8

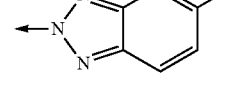

J9

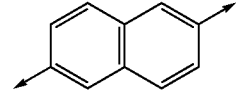

J10

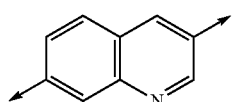

J11

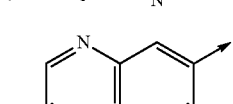

J12

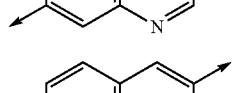

J13

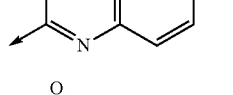

J14 or

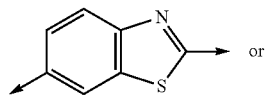

J16

;

wherein R$_{9a}$ and R$_{7a}$ are independently selected from $C_1$-$C_6$alkyl or $C_1$-$C_6$haloalkyl.

3. The compound of claim 1, wherein:
Ar₁ is phenyl or phenyl substituted by one to three substituents independently selected from the group consisting of $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_3$-$C_6$halocycloalkyl, $C_1$-$C_3$haloalkyl-$C_3$-$C_6$cycloalkyl, $C_3$-$C_6$cycloalkoxy, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_2$-$C_4$alkylcarbonyl, CHO, $C_2$-$C_6$alkoxycarbonyl, or $C_2$-$C_6$haloalkoxycarbonyl;

Ar₂ is phenyl or phenyl substituted by one to three substituents independently selected from the group consisting of $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_3$-$C_6$halocycloalkyl, $C_1$-$C_3$haloalkyl-$C_3$-$C_6$cycloalkyl, $C_3$-$C_6$cycloalkoxy, halogen, cyano, nitro, $C_1$-$C_4$alkoxy, $C_1$-$C_4$haloalkoxy, $C_1$-$C_4$alkylthio, $C_1$-$C_4$alkylsulfinyl, $C_1$-$C_4$alkylsulfonyl, $C_1$-$C_4$alkylsulfoximino, $C_2$-$C_4$alkylcarbonyl, CHO, $C_2$-$C_6$alkoxycarbonyl, or $C_2$-$C_6$haloalkoxycarbonyl;

X is a direct bond, or O;

Y is oxygen or sulfur;

R₁ is hydrogen, or $C_1$-$C_6$-alkyl, R₂ and R₃ are independently from each other hydrogen, $C_1$-$C_6$-alkyl, $C_1$-$C_6$-haloalkyl, $C_3$-$C_6$-cycloalkyl, halo-$C_3$-$C_6$-cycloalkyl, $C_2$-$C_6$alkoxycarbonyl, $C_2$-$C_6$alkylaminocarbonyl, $C_3$-$C_6$dialkylaminocarbonyl, $C_2$-$C_6$alkoxycarbonyloxy, $C_2$-$C_6$alkylaminocarbonyloxy, $C_3$-$C_6$dialkylaminocarbonyloxy, provided that when R₂ and R₃ groups are different from hydrogen, said R₂ and R₃ groups can be substituted by one to three substituents independently selected from the group consisting of $C_1$-$C_4$alkyl, $C_2$-$C_4$alkenyl, $C_2$-$C_4$alkynyl, $C_3$-$C_6$cycloalkyl, $C_1$-$C_4$haloalkyl, $C_3$-$C_6$halocycloalkyl, halogen, cyano, nitro, $C_1$-$C_4$alkoxy, $C_1$-$C_4$haloalkoxy, and $C_1$-$C_4$alkylthio;

J is a group selected from:

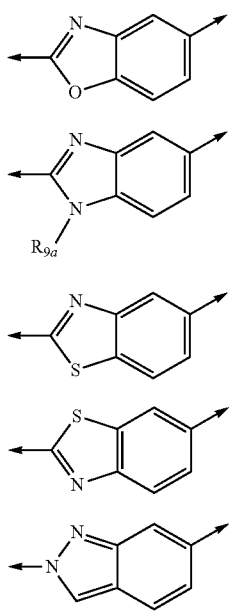

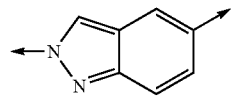
J6

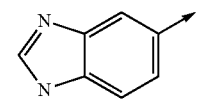
J7

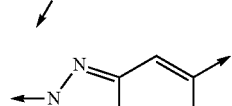
J8

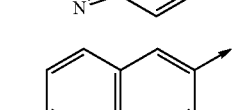
J9

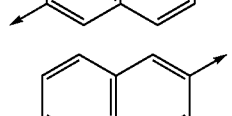
J10

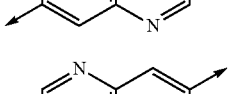
J11

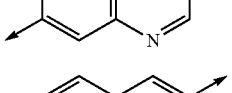
J12

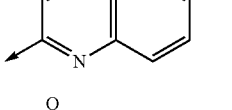
J13

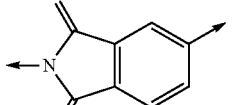
J14 or

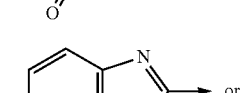
J16

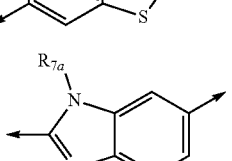

wherein R₇ₐ and R₉ₐ are independently from hydrogen, halogen, nitro, cyano, hydroxy, =O, CHO, $C_1$-$C_6$alkyl, $C_2$-$C_6$alkenyl, $C_2$-$C_6$alkynyl, $C_3$-$C_6$cycloalkyl, $C_1$-$C_6$haloalkyl, $C_2$-$C_6$haloalkenyl, $C_2$-$C_6$haloalkynyl, $C_3$-$C_6$halocycloalkyl, $C_1$-$C_4$alkoxy, $C_1$-$C_4$alkoxy-$C_1$-$C_4$alkoxy-$C_1$-$C_4$alkyl, $C_1$-$C_4$haloalkoxy, $C_1$-$C_4$alkylthio, $C_1$-$C_4$haloalkylthio, $C_1$-$C_4$haloalkylsulfinyl, $C_1$-$C_4$haloalkylsulfonyl, $C_1$-$C_4$alkylsulfinyl, $C_1$-$C_4$alkylsulfonyl, $C_1$-$C_4$alkylsulfonyl-$C_1$-$C_4$alkyl, $C_1$-$C_4$alkylsulfoximino-$C_1$-$C_4$alkyl, $C_1$-$C_4$alkylamino, $C_2$-$C_4$dialkylamino, $C_3$-$C_6$cycloalkylamino, $C_1$-$C_6$alkyl-$C_3$-$C_6$cycloalkylamino, $C_2$-$C_4$alkylcarbonyl, $C_2$-$C_6$alkoxycarbonyl, $C_2$-$C_6$alkylaminocarbonyl, C$_3$-C$_6$dialkylaminocarbonyl, C$_2$-C$_6$alkoxycarbonyloxy, C$_2$-C$_6$alkylaminocarbonyloxy, C$_3$-C$_6$dialkylaminocarbonyloxy, C$_1$-C$_4$alkoxyimino-C$_1$-C$_4$alkyl-CONHSO$_2$—C$_1$-C$_6$-alkyl, —CONHSO$_2$N(C$_1$-C$_6$-alkyl)$_2$, or C$_3$-C$_6$trialkylsilyl.

4. The compound of claim 1, wherein:

Ar$_1$ is phenyl or phenyl substituted by one to three substituents independently selected from the group consisting of C$_1$-C$_4$alkyl, C$_3$-C$_6$cycloalkyl, C$_1$-C$_4$haloalkyl, C$_3$-C$_6$halocycloalkyl, C$_1$-C$_3$haloalkyl-C$_3$-C$_6$cycloalkyl, C$_3$-C$_6$cycloalkoxy, halogen, C$_1$-C$_4$alkoxy, and C$_1$-C$_4$haloalkoxy;

Ar$_2$ is phenyl or phenyl substituted by one to three substituents independently selected from the group consisting of C$_1$-C$_4$alkyl, C$_2$-C$_4$alkenyl, C$_2$-C$_4$alkynyl, C$_3$-C$_6$cycloalkyl, C$_1$-C$_4$haloalkyl, C$_3$-C$_6$halocycloalkyl, C$_1$-C$_3$haloalkyl-C$_3$-C$_6$cycloalkyl, C$_3$-C$_6$cycloalkoxy, halogen, cyano, C$_1$-C$_4$alkoxy, C$_1$-C$_4$haloalkoxy, C$_1$-C$_4$alkylthio;

X is a direct bond, O, S, SO$_2$, CR$_4$R$_5$, or NR$_6$;

Y is oxygen or sulfur;

R$_1$ is hydrogen, C$_1$-C$_6$-alkyl, halo-C$_1$-C$_6$-alkyl, C$_3$-C$_6$-cycloalkyl or C$_1$-C$_3$-alkoxy;

R$_2$ and R$_3$ are independently from each other hydrogen, C$_1$-C$_6$-alkyl, C$_1$-C$_6$-haloalkyl, C$_3$-C$_6$-cycloalkyl, halo-C$_3$-C$_6$-cycloalkyl, C$_2$-C$_6$-alkenyl, C$_2$-C$_6$haloalkenyl, C$_2$-C$_6$-alkynyl, C$_2$-C$_6$haloalkynyl, C$_1$-C$_4$alkoxy-C$_1$-C$_4$alkyl, C$_1$-C$_4$haloalkylsulfinyl, C$_1$-C$_4$haloalkylsulfonyl, C$_1$-C$_4$alkylsulfinyl, C$_1$-C$_4$alkylsulfonyl, C$_2$-C$_4$alkylcarbonyl, C$_2$-C$_6$alkoxycarbonyl, C$_2$-C$_6$alkylaminocarbonyl, C$_3$-C$_6$dialkylaminocarbonyl, C$_2$-C$_6$alkoxycarbonyloxy, C$_2$-C$_6$alkylaminocarbonyloxy, C$_3$-C$_6$dialkylaminocarbonyloxy, or C$_1$-C$_4$alkoxyimino-C$_1$-C$_4$alkyl;

provided that when R$_2$ and R$_3$ are different from hydrogen, R$_2$ and R$_3$ can be substituted by one to three substituents independently selected from the group consisting of C$_1$-C$_4$alkyl, C$_2$-C$_4$alkenyl, C$_2$-C$_4$alkynyl, C$_3$-C$_6$cycloalkyl, C$_1$-C$_4$haloalkyl, C$_2$-C$_4$haloalkenyl, C$_2$-C$_4$haloalkynyl, C$_3$-C$_6$halocycloalkyl, halogen, cyano, nitro, C$_1$-C$_4$alkoxy, C$_1$-C$_4$haloalkoxy, C$_1$-C$_4$alkylthio, C$_1$-C$_4$alkylsulfinyl, C$_1$-C$_4$alkylsulfonyl, C$_1$-C$_4$alkylsulfoximino, C$_1$-C$_4$alkylamino, C$_2$-C$_6$dialkylamino, C$_3$-C$_6$cycloalkylamino, C$_1$-C$_4$alkyl-C$_3$-C$_6$cycloalkylamino, C$_2$-C$_4$alkylcarbonyl, C$_2$-C$_6$alkoxycarbonyl, C$_2$-C$_6$alkylaminocarbonyl, and C$_2$-C$_8$ dialkylaminocarbonyl;

R$_4$, R$_5$ and R$_6$ are independently from each other hydrogen, C$_1$-C$_6$-alkyl, halo-C$_1$-C$_6$-alkyl, C$_3$-C$_6$-cycloalkyl or C$_1$-C$_3$-alkoxy;

J is a group selected from:

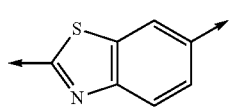

J4

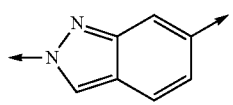

J5

5. The compound of claim 1, wherein:

Ar$_1$ is phenyl or phenyl substituted by one to three substituents independently selected from the group consisting of C$_1$-C$_4$alkyl, C$_3$-C$_6$cycloalkyl, C$_1$-C$_4$haloalkyl, C$_3$-C$_6$halocycloalkyl, C$_1$-C$_3$haloalkyl-C$_3$-C$_6$cycloalkyl, C$_3$-C$_6$cycloalkoxy, halogen, C$_1$-C$_4$alkoxy, and C$_1$-C$_4$haloalkoxy;

Ar$_2$ is phenyl or phenyl substituted by one to three substituents independently selected from the group consisting of C$_1$-C$_4$alkyl, C$_2$-C$_4$alkenyl, C$_2$-C$_4$alkynyl, C$_3$-C$_6$cycloalkyl, C$_1$-C$_4$haloalkyl, C$_3$-C$_6$halocycloalkyl, C$_1$-C$_3$haloalkyl-C$_3$-C$_6$cycloalkyl, C$_3$-C$_6$cycloalkoxy, halogen, cyano, C$_1$-C$_4$alkoxy, C$_1$-C$_4$haloalkoxy, C$_1$-C$_4$alkylthio;

X is a direct bond, O, S, SO$_2$, CR$_4$R$_5$, or NR$_6$;

Y is oxygen or sulfur;

R$_1$ is hydrogen, or C$_1$-C$_6$-alkyl;

R$_2$ and R$_3$ are independently from each other hydrogen, C$_1$-C$_6$-alkyl, C$_1$-C$_6$-haloalkyl;

R$_4$, R$_5$ and R$_6$ are independently from each other hydrogen or C$_1$-C$_6$-alkyl;

J is a group selected from:

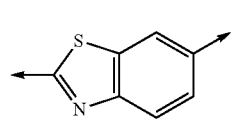

J4

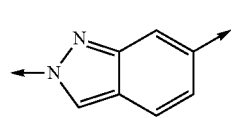

J5

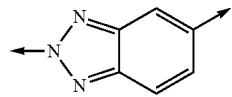

J8

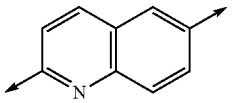

J12

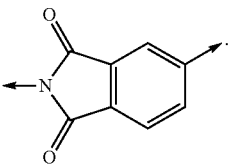

J13

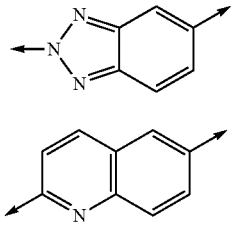

J8

J12

J13

[structure: phthalimide-like bicyclic with N and two C=O]

6. The compound of claim 1, wherein:
Ar$_1$ is phenyl substituted by one C$_1$-C$_4$haloalkoxy;
Ar$_2$ is phenyl substituted by one to three substituents independently selected from the group consisting of C$_1$-C$_4$alkyl, C$_1$-C$_4$haloalkyl, halogen, C$_1$-C$_4$alkoxy, C$_1$-C$_4$haloalkoxy;
X is a direct bond, O, S, SO$_2$, CR$_4$R$_5$, or NR$_6$;
Y is oxygen or sulfur;
R$_1$ is hydrogen, C$_1$-C$_6$-alkyl, halo-C$_1$-C$_6$-alkyl, C$_3$-C$_6$-cycloalkyl or C$_1$-C$_3$-alkoxy;
R$_2$ and R$_3$ are independently from each other hydrogen, C$_1$-C$_6$-alkyl, C$_1$-C$_6$-haloalkyl, C$_3$-C$_6$-cycloalkyl, halo-C$_3$-C$_6$-cycloalkyl, C$_2$-C$_6$-alkenyl, C$_2$-C$_6$haloalkenyl, C$_2$-C$_6$-alkynyl, C$_2$-C$_6$haloalkynyl, C$_1$-C$_4$alkoxy-C$_1$-C$_4$alkyl, C$_1$-C$_4$haloalkylsulfinyl, C$_1$-C$_4$haloalkylsulfonyl, C$_1$-C$_4$alkylsulfinyl, C$_1$-C$_4$alkylsulfonyl, C$_2$-C$_4$alkylcarbonyl, C$_2$-C$_6$alkoxycarbonyl, C$_2$-C$_6$alkylaminocarbonyl, C$_3$-C$_6$dialkylaminocarbonyl, C$_2$-C$_6$alkoxycarbonyloxy, C$_2$-C$_6$alkylaminocarbonyloxy, C$_3$-C$_6$dialkylaminocarbonyloxy, or C$_1$-C$_4$alkoxyimino-C$_1$-C$_4$alkyl;
provided that when R$_2$ and R$_3$ are different from hydrogen, R$_2$ and R$_3$ can be substituted by one to three substituents independently selected from the group consisting of C$_1$-C$_4$alkyl, C$_2$-C$_4$alkenyl, C$_2$-C$_4$alkynyl, C$_3$-C$_6$cycloalkyl, C$_1$-C$_4$haloalkyl, C$_2$-C$_4$haloalkenyl, C$_2$-C$_4$haloalkynyl, C$_3$-C$_6$halocycloalkyl, halogen, cyano, nitro, C$_1$-C$_4$alkoxy, C$_1$-C$_4$haloalkoxy, C$_1$-C$_4$alkylthio, C$_1$-C$_4$alkylsulfinyl, C$_1$-C$_4$alkylsulfonyl, C$_1$-C$_4$alkylsulfoximino, C$_1$-C$_4$alkylamino, C$_2$-C$_6$dialkylamino, C$_3$-C$_6$cycloalkylamino, C$_1$-C$_4$alkyl-C$_3$-C$_6$cycloalkylamino, C$_2$-C$_4$alkylcarbonyl, C$_2$-C$_6$alkoxycarbonyl, C$_2$-C$_6$alkylaminocarbonyl, and C$_2$-C$_8$ dialkylaminocarbonyl;
R$_4$, R$_5$ and R$_6$ are independently from each other hydrogen, C$_1$-C$_6$-alkyl, halo-C$_1$-C$_6$-alkyl, C$_3$-C$_6$-cycloalkyl or C$_1$-C$_3$-alkoxy;
J is a group selected from:

J4

[benzothiazole structure]

J5

[indazole structure]

J12

[quinoline structure]

7. The compound of claim 1, wherein:
Ar$_1$ is phenyl substituted by one C$_1$-C$_4$haloalkoxy;
Ar$_2$ is phenyl substituted by one to three substituents independently selected from the group consisting of C$_1$-C$_4$alkyl, C$_1$-C$_4$haloalkyl, halogen, C$_1$-C$_4$alkoxy, C$_1$-C$_4$haloalkoxy;
X is a direct bond or O;
Y is oxygen or sulfur;
R$_1$ is hydrogen or C$_1$-C$_6$-alkyl,
R$_2$ and R$_3$ are independently from each other hydrogen, C$_1$-C$_6$-alkyl, C$_1$-C$_6$-haloalkyl
J is a group selected from:

J4

[benzothiazole structure]

J5

[indazole structure]

J12

[quinoline structure]

8. The compound of claim 1, wherein J is selected from the group consisting of J$_9$-J$_{11}$ and J$_{12}$.

9. The compound of claim 8, wherein X is a direct bond.

10. The compound of claim 8, wherein X is O, S, SO$_2$, CR$_4$R$_5$ or NR$_6$.

11. The compound of claim 1, wherein J is selected from the group consisting of J$_1$'-J$_3$', J$_4$-J$_8$, and J$_{13}$-J$_{15}$.

12. The compound of claim 11, wherein X is a direct bond.

13. The compound of claim 11, wherein X is O, S, SO$_2$, CR$_4$R$_5$ or NR$_6$.

14. The compound of claim 13, wherein X is O.

15. The compound of claim 1, wherein X is a direct bond or O.

16. The compound of claim 15, wherein X is a direct bond.

17. A pesticidal composition, which comprises at least one compound of formula I according to claim 1 in free form or in agrochemically utilizable salt form, as active ingredient and at least one auxiliary.

18. The pesticidal composition of claim 17, further including a propagation material, wherein the composition is coating the propagation material.

19. A method for controlling pests selected from insects, acarines, mollusc, and nematode, which comprises applying a compound according to claim 1 optionally with at least one auxiliary to the pests or their environment with the proviso that methods for treating a human or animal body using surgery or therapy and/or diagnostic methods practiced on the human or animal body are excluded.

20. A method for the protection of plant propagation material from the attack by pests selected from insects, acarines, mollusc, and nematode, which comprises treating the propagation material or the site, where the propagation material is planted, with a composition according to claim 17.

21. The method of claim 19, wherein the pest are insects.

22. The method of claim 20, wherein the pest are insects.

* * * * *